US012376827B2

(12) United States Patent
Doyle et al.

(10) Patent No.: US 12,376,827 B2
(45) Date of Patent: *Aug. 5, 2025

(54) PORTABLE ULTRASOUND DEVICE

(71) Applicant: BURL Concepts, Inc., San Diego, CA (US)

(72) Inventors: Thomas Francis Doyle, San Diego, CA (US); Thilo Hoelscher, San Diego, CA (US); James Brailean, San Diego, CA (US); Maximillian Dirnbacher, San Diego, CA (US); Arne Voie, San Diego, CA (US); Mark Banham, San Diego, CA (US); Balaji Simma, San Diego, CA (US); Jeffry Tola, San Mario, CA (US)

(73) Assignee: BURL Concepts, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/474,089

(22) Filed: Sep. 25, 2023

(65) Prior Publication Data

US 2024/0016475 A1    Jan. 18, 2024

Related U.S. Application Data

(63) Continuation of application No. 17/232,050, filed on Apr. 15, 2021, now Pat. No. 11,801,036, which is a
(Continued)

(51) Int. Cl.
*A61B 8/00* (2006.01)
*A61B 8/08* (2006.01)
*A61B 8/13* (2006.01)

(52) U.S. Cl.
CPC .......... *A61B 8/4427* (2013.01); *A61B 8/0808* (2013.01); *A61B 8/4227* (2013.01);
(Continued)

(58) Field of Classification Search
CPC ... A61B 8/4427; A61B 8/0808; A61B 8/4227; A61B 8/5223; A61B 8/565; A61B 8/13;
(Continued)

(56) References Cited

U.S. PATENT DOCUMENTS 5,749,364 A    5/1998  Sliwa et al.
9,457,201 B2   10/2016 Hoelscher et al.
(Continued)

FOREIGN PATENT DOCUMENTS

AU    2013259194 B2   4/2016
CA      2428872 C     1/2013
(Continued)

OTHER PUBLICATIONS

Extended European Search Report for European Application 18771037.1, report completed Nov. 24, 2020 Mailed Dec. 3, 2020, 13 Pgs.
(Continued)

*Primary Examiner* — Peter Luong
(74) *Attorney, Agent, or Firm* — KPPB LLP

(57) ABSTRACT

Systems and methods for stroke detection in accordance with embodiments of the invention are illustrated. One embodiment includes a system for detecting strokes, including a processor, a first ultrasound transmitter located on a patient's head in communication with the processor, a first ultrasound receiver located on the patient's head in communication with the processor, a memory in communication with the processor, including a stroke diagnostics application, where the stroke diagnostics application directs the processor to transmit a first ultrasound signal from the first ultrasound transmitter across a patient's brain, the brain comprising a first and second hemisphere, receive the first ultrasound signal using the first ultrasound receiver, where the ultrasound signal is affected during transit by harmonics generated by microbubbles in the blood of the patient
(Continued)

stimulated by the first ultrasound signal, and detect that a stroke has occurred based on the harmonic effects on the first received ultrasound signal.

20 Claims, 23 Drawing Sheets

Related U.S. Application Data continuation of application No. 15/934,921, filed on Mar. 23, 2018, now Pat. No. 11,006,924.

(60) Provisional application No. 62/476,638, filed on Mar. 24, 2017.

(52) U.S. Cl.
CPC ............ *A61B 8/5223* (2013.01); *A61B 8/565* (2013.01); *A61B 8/13* (2013.01); *A61B 8/461* (2013.01); *A61B 8/481* (2013.01)

(58) Field of Classification Search
CPC ........... A61B 8/461; A61B 8/481; A61B 8/06; G16H 50/30
See application file for complete search history.

(56) References Cited

U.S. PATENT DOCUMENTS

| | | | |
|---|---|---|---|
| 9,630,028 B2* | 4/2017 | Browning | A61N 7/00 |
| 11,006,924 B2 | 5/2021 | Doyle et al. | |
| 11,801,036 B2 | 10/2023 | Doyle et al. | |
| 2006/0079773 A1 | 4/2006 | Mourad et al. | |
| 2006/0106311 A1 | 5/2006 | Lo et al. | |
| 2006/0241438 A1 | 10/2006 | Wu et al. | |
| 2007/0016041 A1 | 1/2007 | Nita | |
| 2007/0167705 A1 | 7/2007 | Chiang et al. | |
| 2009/0036780 A1 | 2/2009 | Abraham | |
| 2010/0160780 A1 | 6/2010 | Swan et al. | |
| 2012/0136240 A1 | 5/2012 | Pranevicius et al. | |
| 2014/0039320 A1 | 2/2014 | Jespersen et al. | |
| 2014/0155788 A1 | 6/2014 | Hoelscher et al. | |
| 2014/0235725 A1 | 8/2014 | Morgan | |
| 2015/0164471 A1 | 6/2015 | Morgan | |
| 2016/0030009 A1 | 2/2016 | Hoelscher et al. | |
| 2018/0279995 A1 | 10/2018 | Doyle et al. | |
| 2021/0228182 A1 | 7/2021 | Doyle et al. | |

FOREIGN PATENT DOCUMENTS

| | | |
|---|---|---|
| EP | 3600062 A1 | 2/2020 |
| IN | 201917043022 A | 12/2019 |
| JP | 2020512168 A | 4/2020 |
| JP | 2023024620 A | 2/2023 |
| JP | 7279010 B2 | 5/2023 |
| WO | 2008017998 A2 | 2/2008 |
| WO | 2008017998 A3 | 5/2008 |
| WO | 2014144171 A1 | 9/2014 |
| WO | 2018176005 A1 | 9/2018 |

OTHER PUBLICATIONS

International Preliminary Report on Patentability for International Application PCT/US2018/024204, Report issued Sep. 24, 2019, Mailed Oct. 3, 2019, 06 Pgs.
International Search Report and Written Opinion for International Application No. PCT/US2018/024204, completed Jun. 24, 2018, mailed Jul. 13, 2018, 10 pgs.
"Our new device", Burl Concepts Inc., Retrieved from: http://burlconcepts.com/ournewdevice/, Retrieved on Oct. 4, 2016, 3 pgs.
"Sonas: Prehospital Stroke Diagnosis Using Ultra sound", Burl Concepts, Inc., 1 pg.
Aaslid et al., "Noninvasive transcranial Doppler ultrasound recording of flow velocity in basal cerebral arteries", J. Neurosurg., 1982, vol. 57, pp. 769-774.
Bartels et al., "Transcranial Contrast Imaging of Cerebral Perfusion in Patients with Space-Occupying Intracranial Lesions", Journal of Ultrasound in Medicine, 2006, vol. 25, pp. 499-507.
Baumgartner et al., "Assessment of ≥50% and <50% Intracranial Stenoses by Transcranial Color-Coded Duplex Sonography", Stroke, Jan. 1999, vol. 30, pp. 87-92.
Becker et al., "Differentiation Between Ischemic and Hemorrhagic Stroke by Transcranial Color-coded Real-time Sonography", Journal of Neuroimaging, Jan. 1993, vol. 3, No. 1, pp. 41-47.
Becker et al., "Transcranial Color-Coded Real-Time Sonography of Intracranial Veins", Journal of Neuroimaging, Apr. 1995, vol. 5, No. 2, pp. 87-94.
Bogdahn et al., "Transcranial Color-Coded Real-time Sonography in Adults", Stroke, Dec. 1990, vol. 21, No. 12, pp. 1680-1688.
Droste, "Clinical Utility of Contrast-Enhanced Ultrasound in Neurosonology", European Neurology, Mar. 26, 2008, vol. 59, Suppl. 1, pp. 2-8.
Droste et al., "Clinical utility of echocontrast agents in neurosonology", Neurological Research, Oct. 2004, vol. 26, pp. 754-759.
Droste et al., "SonoVue® (BR1), a New Long-Acting Echocontrast Agent, Improved Transcranial Colour-Coded Duplex Ultrasonic Imaging", Cerebrovasc. Dis., 2002, vol. 14, pp. 27-32.
Eyding et al., "Parameters of Cerebral Perfusion in Phase-Inversion Harmonic Imaging (PIHI) Ultrasound Examinations", Ultrasound in Medicine and Biology, Oct. 1, 2003, vol. 29, No. 10, pp. 1379-1385.
Eyding et al., "Reliability of Semiquantitative Ultrasonic Perfusion Imaging of the Brain", Journal of Neuroimaging, Apr. 2004, vol. 14, pp. 143-149.
Gahn et al., "Contrast-Enhanced Transcranial Color-Coded Duplexsonography in Stroke Patients with Limited Bone Windows", Am. Journal Neuroradiol., Mar. 2000, vol. 21, pp. 509-514.
Goertler et al., "Diagnostic Impact and Prognostic Relevance of Early Contrast-Enhanced Transcranial Color-Coded Duplex Sonography in Acute Stroke", Stroke, May 1998, vol. 29, pp. 955-962.
Gramiak et al., "Echocardiography of the Aortic Root", Investigative Radiology, Sep.-Oct. 1968, No. 5, pp. 356-366.
Holscher et al., "Transcranial Ultrasound Angiography (tUSA): A New Approach for Contrast Specific Imaging of Intracranial Arteries", Ultrasound in Medicine and Biology, 2005, vol. 31, No. 8, pp. 1001-1006.
Holscher et al., "Transcranial Ultrasound Brain Perfusion Assessment with a Contrast Agent-Specific Imaging Mode", Stroke, Oct. 2005, vol. 46, pp. 2283-2285.
Holscher et al., "Transcranial Ultrasound from Diagnosis to Early Stroke Treatment", Cerebrovascular Diseases, 2008, vol. 26, pp. 659-663, published online Nov. 4, 2008.
Jungehulsing et al., "Diagnostic Transcranial Ultrasound Perfusion-Imaging at 2.5 MHZ Does Not Affect the Blood-Brain Barrier", Ultrasound in Medicine & Biology, 2008, vol. 34, No. 1, pp. 147-150.
Kaps et al., "Prognostic Value of Transcranial Sonography in Acute Stroke Patients", European Neurology, 2008, vol. 59, Suppl. 1, pp. 9-16, published online Mar. 26, 2008.
Kaps et al., "SonoVue™ in Transcranial Doppler Investigations of the Cerebral Arteries", Journal of Neuroimaging, Jul. 2001, vol. 11, pp. 261-267.
Kashif et al., "Model-Based Noninvasive Estimation of Intracranial Pressure from Cerebral Blood Flow Velocity and Arterial Pressure", Science Translation Medicine, vol. 4, No. 129, Apr. 11, 2012, 22 pgs.
Kern et al., "Ultrasound Microbubble Destruction Imaging in Acute Middle Cerebral Artery Stroke", Stroke, Jul. 2004, vol. 35, pp. 1665-1670.
Meyer-Wiethe et al., "Ultrasound Perfusion Imaging: Determination of Thresholds for the Identification of Critically Disturbed Perfusion in Acute Ischemic Stroke—A Pilot Study", Ultrasound in Medicine and Biology, Jun. 1, 2007, vol. 33, No. 6, pp. 851-856.
Pohl et al., "Stimulated Acoustic Emission Detected byb Transcranial Color Doppler Ultrasound", Stroke, Jul. 2000, vol. 31, pp. 1661-1666.

(56) References Cited

OTHER PUBLICATIONS

Postert et al., "Comparison of Transcranial Power Doppler and Contrast-Enhanced Color-Coded Sonography in the Identification of Intracranial Arteries", Journal of Ultrasound Medicine, 1998, vol. 17, pp. 91-96.
Postert et al., "Transient Response Harmonic Imaging", Stroke, Sep. 1998, vol. 29, pp. 1901-1907.
Sauerbruch et al., "Application of Transcranial Color-Coded Duplex Sonography in Stroke Diagnosis", Current Medical Imaging Reviews, 2009, vol. 5, p. 39-54 (2009), pp. 39, 44.
Schlachetzki et al., "Observation on the Integrity of the Blood-Brain Barrier After Microbubble Destruction by Diagnostic Transcranial Color-Coded Sonography", Journal of Ultrasound Medicine, 2002, vol. 21, pp. 419-429.
Schlachetzki et al., "Transcranial Ultrasound from Diagnosis to Early Stroke Treatment—Part 2: Prehospital Neurosonography in Patients with Acute Stroke—The Regensburg Stroke Mobile Project", Cerebrovascular Diseases, 2012, vol. 33, pp. 262-271, published online Jan. 19, 2012.
Schweikert et al., "Transcranial Duplex Imaging with a Sulfurhexafluoride Echocontrast Agent: Enhancement and Diagnostic Quality", Journal of Neuroimaging, Jan. 2002, vol. 12, No. 1, pp. 19-27.
Seidel et al., "Ultrasound Perfusion Imaging in Acute Middle Cerebral Artery Infarction Predicts Outcome", Stroke, May 2004, vol. 35, pp. 1107-1111.
Shen et al., "Pulse Inversion Techniques in Ultrasonic Nonlinear Imaging", Journal of Medical Ultrasound, vol. 13, No. 1, 2005, pp. 3-17.
Sidhu et al., "Diagnostic efficacy of SonoVue®, a second generation contrast agent, in the assessment of extracranial cartod or peripheral arteries using colour and spectral Doppler ultrasound: a multicentre study", The British Journal of Radiology, Jan. 2006, vol. 79, pp. 44-51.
Stroick et al., "Effects of Simultaneous Application of Ultrasound and Microbubbles on Intracerebral Hemmorhage in an Animal Model", Ultrasound in Medicine and Biology, 2006, vol. 32, No. 9, pp. 1377-1382.
Turner et al., "Intracranial Aneurysms Treated with Endovascular Coils", Stroke, Dec. 2005, vol. 36, pp. 2654-2659.
Weismann et al., "Parametric Perfusion Imaging with Contrast-Enhanced Ultrasound in Acute Ischemic Stroke", Stroke, Feb. 2004, vol. 35, pp. 508-513.

\* cited by examiner

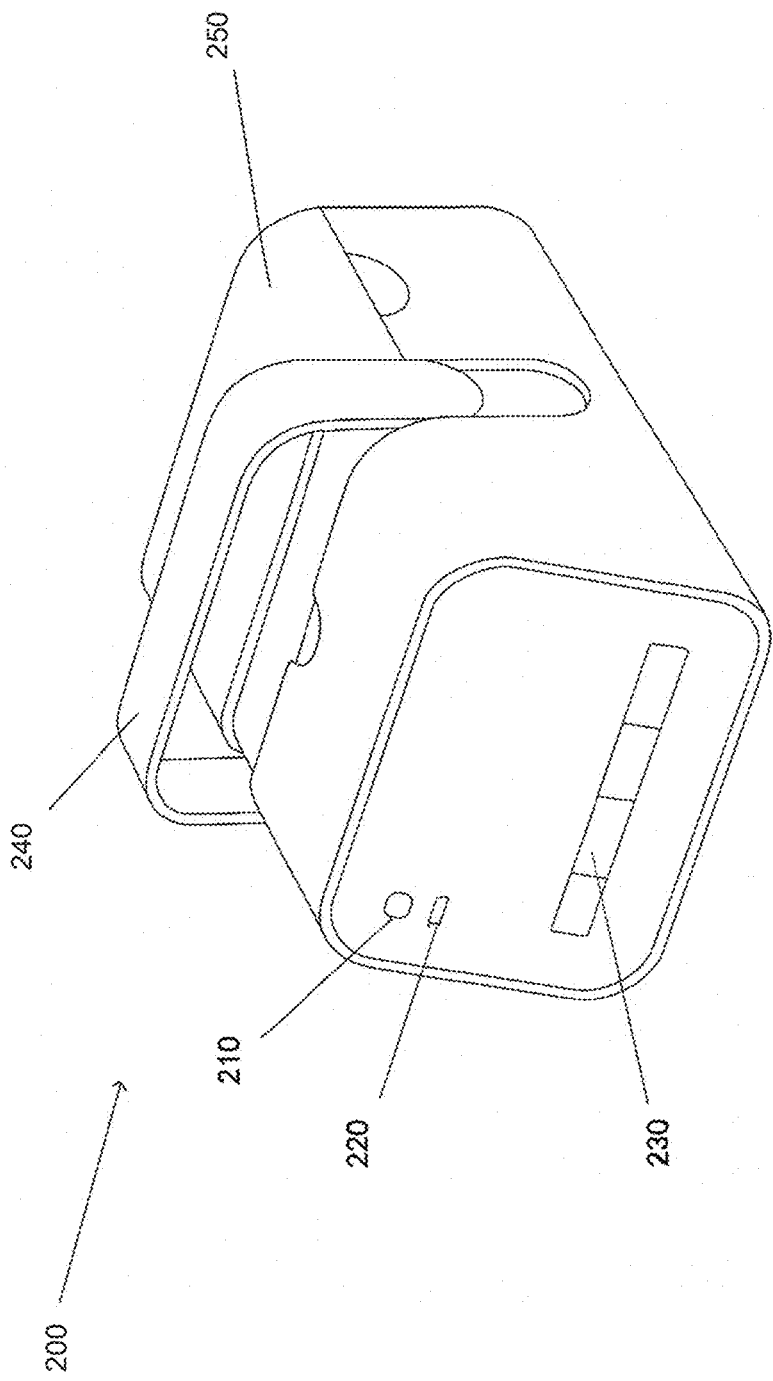

Contralateral Receiving

PORTABLE ULTRASOUND DEVICE

CROSS-REFERENCE TO RELATED APPLICATIONS

The present application is a continuation of U.S. Non-Provisional application Ser. No. 17/232,050 filed Apr. 15, 2021, which is a continuation of U.S. Non-Provisional application Ser. No. 15/934,921 filed Mar. 23, 2018, issued on May 18, 2021 as U.S. Pat. No. 11,006,924, which claims the benefit of U.S. Provisional Application No. 62/476,638 filed Mar. 24, 2017, the entirety of which is hereby incorporated by reference.

FIELD OF THE INVENTION

The present invention relates generally to ultrasound diagnostic technology, and more specifically to apparatuses and methods for detecting internal injury using ultrasound.

BACKGROUND

Ultrasound waves are often described as sound waves having frequencies greater than 20 kHz. Ultrasound has been used in the medical field to observe the interior of the human body in a non-invasive manner. The ultrasound is applied using an ultrasound transducer that typically comes into contact with the patient's skin. Ultrasound is readily absorbed in air, so gel is often used between the transducer and the skin to enhance the transmission of ultrasound. In some cases, the gel is a liquid substance. In other cases, a gel pad is used where the gel is molded into semi-solid disks.

A gel is a solid jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinking within the fluid that gives a gel its structure (hardness) and contributes to the adhesive stick (tack). In this way gels are a dispersion of molecules of a liquid within a solid in which the solid is the continuous phase and the liquid is the discontinuous phase.

Microbubbles are bubbles that have a diameter on the micrometer scale, but smaller than one millimeter. Microbubbles can be used as ultrasound contrasting agents because they can oscillate and vibrate when a sonic energy field is applied and may reflect ultrasound waves. This distinguishes the microbubbles from surrounding tissues.

Strokes are a common cause of death in the United States of America. Every year, more than 795,000 people in the United States have a stroke. Strokes can be classified into two major categories: ischemic and hemorrhagic. Ischemic strokes are caused by the interruption of the blood supply to the brain, while hemorrhagic strokes result from the rupture of a blood vessel or an abnormal vascular structure.

SUMMARY OF THE INVENTION

Systems and methods for stroke detection in accordance with embodiments of the invention are illustrated. One embodiment includes A system for detecting strokes, including a processor, a first ultrasound transmitter located on a patient's head in communication with the processor, a first ultrasound receiver located on the patient's head in communication with the processor, a memory in communication with the processor, including a stroke diagnostics application, where the stroke diagnostics application directs the processor to transmit a first ultrasound signal from the first ultrasound transmitter across a patient's brain, the brain comprising a first hemisphere and a second hemisphere, receive the first ultrasound signal using the first ultrasound receiver, where the ultrasound signal is affected during transit by harmonics generated by microbubbles in the blood of the patient stimulated by the first ultrasound signal, and detect that a stroke has occurred based on the harmonic effects on the first received ultrasound signal.

In another embodiment, the stroke diagnostics application further directs the processor to compare the portion of the received ultrasound signal corresponding to the first hemisphere of the brain to the portion of the ultrasound signal corresponding to the second hemisphere of the brain, and detect differences in microbubble signal profile between the first hemisphere and the second hemisphere based on the harmonic effects on the first received ultrasound signal.

In a further embodiment, the first ultrasound receiver is located on the patient's head ipsilaterally with respect to the first ultrasound transmitter, and wherein the stroke diagnostics application further directs the processor to transmit a second ultrasound signal from a second ultrasound transmitter across the patient's brain, where the second ultrasound transducer is in communication with the processor and is located contralaterally on the patient's head with respect to the first ultrasound transmitter, and receive the second ultrasound signal using a second ultrasound receiver, where the second ultrasound receiver is located ipsilaterally on the patient's head with respect to the second ultrasound transmitter, where the second ultrasound receiver is in communication with the processor, and where the second ultrasound signal is affected during transit by harmonics generated by microbubbles in the blood of the patient stimulated by the second ultrasound signal.

In still another embodiment, the stroke diagnostics application further directs the processor to determine the transmit time of ultrasound across the patient's head, time-box the first received ultrasound signal such that the first time-boxed signal corresponds to the signal received during a time period of half of the determined transmit time so that the first time-boxed signal describes the first hemisphere of the brain, time-box the second received ultrasound signal such that the second time-boxed signal corresponds to the signal received during a time period of half of the determined transmit time so that the second time-boxed signal describes the second hemisphere of the brain, and compare the first time-boxed signal and the second time-boxed signal for differences in harmonic responses.

In a still further embodiment, the first ultrasound is located contralaterally on the patient's head with respect to the first ultrasound transmitter, and wherein the stroke diagnostics application further directs the processor to transmit a second ultrasound signal from the second ultrasound transmitter across the patient's brain, where the second ultrasound transmitter is located contralaterally on the patient's head with respect to the first ultrasound transmitter, and receive the second ultrasound signal using a second ultrasound receiver, where the second ultrasound receiver is located contralaterally on the patient's head with respect to the first ultrasound transmitter, where the second ultrasound receiver is in communication with the processor, and where the second ultrasound signal is affected during transit by harmonics generated by microbubbles in the blood of the patient stimulated by the second ultrasound signal.

In yet another embodiment, the stroke diagnostics application further directs the processor to locate the position of the detected stroke within the brain.

In a yet further embodiment, the stroke diagnostics application further directs the processor to time-box the received ultrasound signal to reflect spatial segments of the brain, and determine which spatial segment contains harmonic effects indicating injury.

In another additional embodiment, the stroke diagnostics application further directs the processor to analyze a first segment of the received ultrasound signal corresponding to the distance from the first ultrasound transmitter to a predetermined segment distance from the first ultrasound transmitter, and analyze a set of subsequent segments, where each subsequent segment in the set of subsequent segments sequentially describes the received ultrasound signal from the first ultrasound transmitter to a distance that is one more predetermined segment distance away from the first ultrasound transmitter than the previous segment.

In a further additional embodiment, the stroke diagnostics application further directs the processor to analyze a first segment of the received ultrasound signal corresponding to the distance from the first ultrasound transmitter to a predetermined segment distance from the of the first ultrasound transmitter, and analyze a set of subsequent segments, where each subsequent segment in the set of subsequent segments sequentially describes the received ultrasound signal from the previous segment to a distance that is one more predetermined segment distance away from the first ultrasound transmitter than the previous segment.

In another embodiment again, the stroke diagnostics application further directs the processor to determine whether the stroke is an ischemic stroke or a hemorrhagic stroke based on the received ultrasound signal.

In a further embodiment again, the stroke diagnostics application further directs the processor to match the harmonic effects to a known set of harmonic effects stored in the memory.

In still yet another embodiment, the stroke diagnostics application further directs the processor to identify blood pooling by locating harmonic effects representing microbubbles pooling in a region of the brain for an extended period.

In a still yet further embodiment, the stroke diagnostics application further directs the processor to identify areas where no harmonic effects representing microbubbles are present.

In still another additional embodiment, the microbubbles generate different harmonic frequencies depending on the pressure that the microbubbles are subject to, and wherein the stroke diagnostics application further directs the processor to measure the frequencies associated with the microbubble harmonic effects, and calculate an intracranial pressure of the patient based on the measured frequencies, determine a type of stroke based on the intracranial pressure.

In a still further additional embodiment, the received first ultrasound signal is further affected by unwanted harmonic noise, and the stroke detection application further directs the processor to reduce unwanted harmonic noise by transmitting a second ultrasound signal using the first ultrasound transmitter, where the second ultrasound signal is 180 degrees out of phase with the first transmitted ultrasound signal, and filter the first ultrasound signal to remove unwanted harmonic noise, where the unwanted harmonic noise is correlated to phase.

In still another embodiment again, the received first ultrasound signal includes a first peak and a second peak, where the received first ultrasound signal's first peak and second peak correspond to harmonic effects, and wherein the stroke detection application further directs the processor to locate the first received ultrasound signal's first peak by finding a first inflection point in the received first ultrasound signal, locate the first received ultrasound signal's second peak by finding a second inflection point in the received first ultrasound signal, and match the pattern of the peaks in the first received ultrasound signal to predetermined patterns of peaks representing brains suffering from stroke.

In a still further embodiment again, the stroke detection application further directs the processor to transmit a second ultrasound signal using a second ultrasound transmitter, where the second ultrasound transmitter is located on the patient's head contralaterally with respect to the first ultrasound transmitter, and where the second ultrasound transmitter is in communication with the processor, receive the second ultrasound signal using at least one of the first ultrasound receiver and a second ultrasound receiver, where the second ultrasound receiver is located on the patient's head contralaterally with respect to the first ultrasound receiver, where the second received ultrasound signal comprises a first peak and a second peak, and where the second ultrasound signal's first peak and second peak correspond to harmonic effects, locate the second received ultrasound signal's first peak by finding a first inflection point in the received first ultrasound signal, locate the second received ultrasound signal's second peak by finding a second inflection point in the received first ultrasound signal, calculate the differences between the first received ultrasound signal's peaks with the second received ultrasound signal's peaks, and detect if a stroke has occurred based on the calculated differences.

In yet another additional embodiment, a first ultrasound transducer assembly comprises the first ultrasound transmitter and the first ultrasound receiver.

In a yet further additional embodiment, the first ultrasound transducer assembly comprises a coaxial dual element ultrasound transducer.

In yet another embodiment again, a method for detecting strokes includes transmitting a first ultrasound signal from a first ultrasound transmitter across a patient's brain, where the brain comprises a first hemisphere and a second hemisphere, and receiving the first ultrasound signal using a first ultrasound receiver, where the ultrasound signal is affected during transit by harmonics generated by microbubbles in the blood of the patient stimulated by the first ultrasound signal, and detecting that a stroke has occurred based on the harmonic effects on the first received ultrasound signal.

In a yet further embodiment again, detecting if a stroke has occurred further includes comparing the portion of the received ultrasound signal corresponding to the first hemisphere of the brain to the portion of the ultrasound signal corresponding to the second hemisphere of the brain, and detecting differences in microbubble signal profile between the first hemisphere and the second hemisphere based on the harmonic effects on the first received ultrasound signal.

In another additional embodiment again, the first ultrasound receiver is located on the patient's head ipsilaterally with respect to the first ultrasound transmitter, and further includes transmitting a second ultrasound signal using a second ultrasound transmitter across the patient's brain, where the second ultrasound transmitter is located on the patient's head contralaterally with respect to the first ultrasound transmitter, and receiving the second ultrasound signal using a second ultrasound receiver, where the second ultrasound receiver is located on the patient's head contralaterally with respect to the first ultrasound transmitter, and where the second ultrasound signal is affected during transit by harmonics generated by microbubbles in the blood of the patient stimulated by the second ultrasound signal, and detecting if a stroke has occurred is further based on the harmonic effects on the second received ultrasound signal.

In a further additional embodiment again, the method further includes determining the transit time of ultrasound across the patient's head, time-boxing the first received ultrasound signal such that the first time-boxed signal corresponds to the signal received during a time period of half of the determined transmit time so that the first time-boxed signal describes the first hemisphere of the brain, time-boxing the second received ultrasound signal such that the second time-boxed signal corresponds to the signal received during a time period of half of the determined transmit time so that the second time-boxed signal describes the second hemisphere of the brain, and comparing the first time-boxed signal and the second time-boxed signal for differences in harmonic responses.

In still yet another additional embodiment, the first ultrasound receiver is located on the patient's head contralaterally with respect to the first ultrasound transmitter, and the method further includes transmitting a second ultrasound signal from a second ultrasound transmitter across the patient's brain, where the second ultrasound transmitter is located on the patient's head contralaterally with respect to the first ultrasound transmitter, receiving the second ultrasound signal using a second ultrasound receiver, where the second ultrasound receiver is located on the patient's head ipsilaterally with respect to the first ultrasound transmitter, and where the second ultrasound signal is affected during transit by harmonics generated by microbubbles in the blood of the patient stimulated by the second ultrasound signal, and detecting if a stroke has occurred is further based on the harmonic effects on the second received ultrasound signal.

In another embodiment, the method further includes locating the position of the detected stroke within the brain.

In a further embodiment, locating the position of the detected stroke within the brain includes time-boxing the received ultrasound signal to reflect spatial segments of the brain, and determining which spatial segment contains harmonic effects indicating injury.

In still another embodiment, time-boxing the received ultrasound signal includes analyzing a first segment of the received ultrasound signal corresponding to the distance from the first ultrasound transducer assembly to a predetermined segment distance from the of the first ultrasound transmitter, and analyzing a set of subsequent segments, where each subsequent segment in the set of subsequent segments sequentially describes the received ultrasound signal from the first ultrasound transducer assembly to a distance that is one more predetermined segment distance away from the first ultrasound transducer assembly than the previous segment.

In a still further embodiment, time-boxing the received ultrasound signal includes analyzing a first segment of the received ultrasound signal corresponding to the distance from the first ultrasound transmitter to a predetermined segment distance from the of the first ultrasound transmitter, and analyzing a set of subsequent segments, where each subsequent segment in the set of subsequent segments sequentially describes the received ultrasound signal from the previous segment to a distance that is one more predetermined segment distance away from the first ultrasound transmitter than the previous segment.

In yet another embodiment, the method further includes determining whether the stroke is an ischemic stroke or a hemorrhagic stroke based on the received ultrasound signal.

In a yet further embodiment, determining whether the stroke is an ischemic stroke or a hemorrhagic stroke includes matching the harmonic effects to a known set of harmonic effects.

In another additional embodiment, determining whether the stroke is a hemorrhagic stroke includes identifying blood pooling by locating harmonic effects representing microbubbles pooling in a region of the brain for an extended period.

In a further additional embodiment, determining whether the stroke is an ischemic stroke includes identifying areas where no harmonic effects representing microbubbles are present.

In another embodiment again, the microbubbles generate different harmonic frequencies depending on the pressure that the microbubbles are subject to, and wherein determining whether the stroke is a hemorrhagic stroke or an ischemic stroke includes measuring the frequencies associated with the microbubble harmonic effects, calculating an intracranial pressure of the patient based on the measured frequencies, and determining a type of stroke based on the intracranial pressure.

In a further embodiment again, the received first ultrasound signal is further affected by unwanted harmonic noise, and reducing unwanted harmonic noise includes transmitting a second ultrasound signal using the first ultrasound transmitter assembly, where the second ultrasound signal is 180 degrees out of phase with the first transmitted ultrasound signal, and filtering the first ultrasound signal to remove unwanted harmonic noise, where the unwanted harmonic noise is correlated to phase.

In still yet another embodiment, the received first ultrasound signal includes a first peak and a second peak, where the received first ultrasound signal's first peak and second peak correspond to harmonic effects, and wherein detecting if a stroke has occurred includes locating the first received ultrasound signal's first peak by finding a first inflection point in the received first ultrasound signal, locating the first received ultrasound signal's second peak by finding a second inflection point in the received first ultrasound signal, and matching the pattern of the peaks in the first received ultrasound signal to predetermined patterns of peaks representing brains suffering from stroke.

In a still yet further embodiment, the method further includes transmitting a second ultrasound signal using a second ultrasound transmitter, receiving the second ultrasound signal using at least one of the first ultrasound receiver and a second ultrasound receiver, where the second received ultrasound signal includes a first peak and a second peak, where the second ultrasound signal's first peak and second peak correspond to harmonic effects, locating the second received ultrasound signal's first peak by finding a first inflection point in the received first ultrasound signal, locating the second received ultrasound signal's second peak by finding a second inflection point in the received first ultrasound signal, calculating the differences between the first received ultrasound signal's peaks with the second received ultrasound signal's peaks, and detecting whether a stroke has occurred based on the calculated differences.

In still another additional embodiment, the method further includes calculating an appropriate attenuation sufficient for detecting strokes, and displaying an indicator representing if the attenuation is sufficient for diagnostic testing based on the difference between a current attenuation and the calculated attenuation.

In a still further additional embodiment, a system for detecting strokes includes a processor, an ultrasound transmitter element in communication with the processor, an ultrasound receiver element in communication with the processor, and a memory in communication with the processor, the memory including a stroke diagnostics application, where the stroke diagnostics application directs the processor to transmit an ultrasound signal across a patient's brain using the ultrasound transmitter element, where the blood in the patient's brain contains microbubbles, receive the ultrasound signal using the ultrasound receiver element, calculate the differences in the received ultrasound signal from the transmitted ultrasound signal based on microbubble harmonic resonance, and determine whether or not a stroke has occurred based on the microbubble harmonic resonance.

In still another embodiment again, a method for placing ultrasound transducer assemblies on a patient for stroke detection using a portable ultrasound device includes placing a first ultrasound transducer assembly at a first location on a patient's head, placing a second ultrasound transducer assembly at a second location on a patient's head, transmitting an ultrasound signal from the first ultrasound transducer assembly across the patient's head, receiving the ultrasound signal using the second ultrasound transducer assembly, calculating the expected amplitude of the ultrasound signal if the first and second ultrasound transducers were properly aligned, calculating the difference between the calculated expected and a measured amplitude of the received ultrasound signal, and providing an indicator representing if the alignment of the is sufficient for diagnostic testing based on the calculated difference.

In a still further embodiment again, the method further includes calculating an appropriate attenuation sufficient for detecting strokes using a portable ultrasound device on the patient, and displaying an indicator representing if the attenuation is sufficient for diagnostic testing based on the difference between a current attenuation and the calculated attenuation.

In yet another additional embodiment, the indicator is visually provided using a display.

In a yet further additional embodiment, the indicator is audibly provided using a speaker.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

FIG. 2 is a rendering of a portable ultrasound device in accordance with an embodiment of the invention.

DETAILED DESCRIPTION

Figure 1:
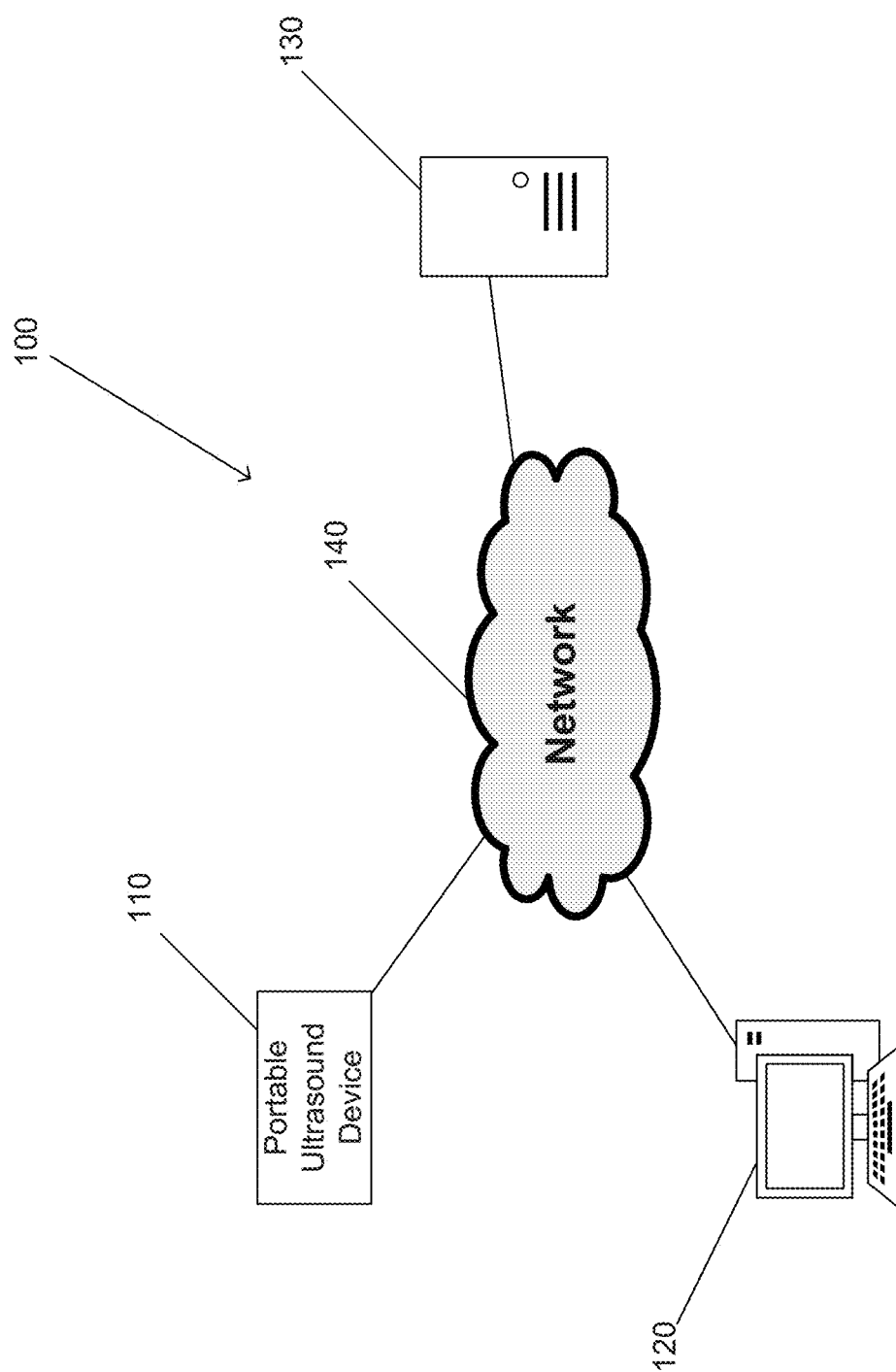
FIG. 1 is a conceptual illustration of a portable ultrasound device in communication with a variety of medical systems in accordance with an embodiment of the invention.

Turning now to the drawings, portable ultrasound devices, and methods of using portable ultrasound devices are illustrated. Strokes are a leading cause of death and serious long-term disability in the United States. When a patient in the field suffers a stroke, emergency medical technicians (EMTs) are often dispatched in an ambulance to bring the person to a hospital for treatment. For brain related injuries such as a stroke, the longer a patient goes without treatment, the higher the risk of long term brain damage or death. Rapid diagnosis of stroke can quicken the application of treatment, potentially saving the patient pain and suffering.

While in the field, it is difficult for EMTs to quickly and/or accurately diagnose a stroke. It is particularly difficult to determine the type of stroke and where in the brain the damage has occurred. Portable ultrasound devices can be small enough to be transported in an ambulance and/or be carried by hand. In numerous embodiments, portable ultrasound devices are used to diagnose strokes and other brain injuries. Portable ultrasound devices can be used in the field to quickly suggest diagnoses without requiring large laboratory equipment such as MRI machines or CT Scanners. Portable ultrasound devices can instead use self-contained diagnostic equipment to suggest diagnoses. Self-contained diagnostic equipment can include, but is not limited to, transducer assemblies, positioning bands, calibration tools, and/or any other piece of diagnostic equipment appropriate to the requirements of given applications.

In numerous embodiments, portable ultrasound devices are used to determine whether or not a patient is having a stroke or has just had a stroke. Portable ultrasound devices can be utilized in conjunction with positioning bands which are used to attach transducer assemblies to the patient's head. In many embodiments, positioning bands are in the form of a headband with sockets for transducer assemblies and ultrasound gel pads. In numerous embodiments, two transducer assemblies are attached to the patient's head. In a variety of embodiments, the two transducer assemblies are placed on either side of the patient's head above the ears. In many embodiments, two transducer assemblies are positioned on the temporal bones of the patient's head. However, the transducer assemblies can be placed in any orientation in accordance with the requirements of a given application. Positioning bands can be designed to apply sufficient pressure between the transducer assemblies and the head of the patient in order to reduce the amount of time it takes for the shape of the ultrasound gel pads and the surrounding environment (e.g. hair, skin, etc.) to settle. Ultrasound can be transmitted and received by the transducer assemblies. Microbubbles can be administered to the patient as an ultrasound acoustic markers. When microbubbles are in an acoustic field, they can be excited and reflect ultrasound in a characteristic and recognizable way. In this way, the pattern of received ultrasound at a transducer assembly can be used to generate diagnostic support data describing, in part or in whole, a suggested diagnosis of what type of brain injury the patient is suffering from. For example, in numerous embodiments, diagnostic support data describes a likelihood of whether or not a stroke has occurred and/or the type of stroke that may have occurred. In many embodiments, diagnostic support data describes any number of metrics and/or characteristics obtained by the portable ultrasound device.

In several embodiments, portable ultrasound devices can have tissue protective applications. Tissue protective applications of the portable ultrasound device can be achieved in non-emergent situations where cerebral blood flow improvement may have benefits, such as, but not limited to, geriatric cognitive acuity, improved hearing via improved cochlear blood flow, or any other tissue protective applications of ultrasound and/or microbubbles as appropriate to the requirements of given applications. Various ultrasound devices and techniques for using ultrasound for diagnostic and therapeutic purposes in accordance with embodiments of the invention are discussed below.

Network Connected Portable Ultrasound Devices

In many embodiments, portable ultrasound devices can be connected to a variety of other computing devices via various networks. This allows the portable ultrasound device to transmit data to other systems, such as, but not limited to, server systems and/or computers including (but not limited to) mobile phones, personal computers, and tablet computing devices. Information collected by a portable ultrasound device can be used to prepare additional diagnoses and treatment options for when the patient arrives at a medical facility.

Turning now to FIG. 1, a portable ultrasound device is shown communicating with various other computing devices in accordance with an embodiment of the invention. The system 100 can be made of one or more portable ultrasound devices 110 that communicate with one or more computers 120 and/or server systems 130 via one or more networks 140. In many embodiments, ultrasound medical device 110 is connected to network 140 via a wireless signal. In numerous embodiments, a cellular phone can be used as an intermediary between the ultrasound medical device 110 and network 140. In a variety of embodiments, ultrasound medical device 110 has a network interface which allows for connections to the network 140. The network interface can permit communications over a wired connection, and/or a wireless connection. In some embodiments, the network interface uses the Bluetooth wireless connectivity standard. However, any type of wired or wireless communication method can be used as appropriate to the requirements of given applications.

Diagnostic information can include, but is not limited to, data collected by the ultrasound medical device 110, data input by the user of the portable ultrasound device 110, or any other type of information as appropriate to the requirements of given applications. In many embodiments, data input by the user of the portable ultrasound device includes audio recordings captured by a microphone connected to the portable ultrasound device. In some embodiments, data input by the user can be text data. In numerous embodiments, data input by the user can be audio and/or image data. Data transmitted by the portable ultrasound device can be identified by a serial number associated with the portable ultrasound device and/or a time stamp corresponding to the time of use.

In certain embodiments, data is transmitted in a real time stream to an adjacent and/or remote computing device. In several embodiments, a portable ultrasound device communicates collected data in a batch upload process. Server system 130 can process diagnostic information and provide information to computer 120 and/or can transmit information back to ultrasound device 110. In some embodiments, the portable ultrasound device 110 transmits unprocessed collected ultrasound data to server system 130, where the server system 130 processes the collected ultrasound data and provides diagnostic support data. In numerous embodiments, the ultrasound medical device 110 is capable of providing diagnostic support data without connectivity to another computing device.

In many embodiments, a trusted certificate system can be used to ensure the veracity of transmitted data. In a number of embodiments, public/private key systems can be used to encrypt the transmitted data. In several embodiments, users must provide key data to the portable ultrasound device in order to use the device. In numerous embodiments, portable ultrasound devices transmit data to a server system that stores data. Server systems can analyze obtained ultrasound device data. In some embodiments, server systems are configured to analyze data perform at least one of: improving the analytic sensitivity of the system, correlating patient outcomes with diagnostic support data, predicting medical events, correlating diagnostic support data with medical history, risk profiles, and/or vital signs, correlating diagnostic support data with imaging methods, performing epidemiological analysis, performing cost analytics, and/or any other analysis as appropriate to the requirements of a given application. Although a specific architecture for a system for communication between a portable ultrasound device and various other devices is shown in FIG. 1, any number of system architectures could be used in accordance with the requirements of given applications.

Portable Ultrasound Devices

Ultrasound devices in accordance with several embodiments of the invention can be made in a portable form. Housings for portable ultrasound devices can have different form factors. Portable ultrasound devices can be small enough and light enough that they can be stored in an ambulance or other medical vehicle. In numerous embodiments, portable ultrasound devices have compartments which store self-contained diagnostic equipment. Portable ultrasound devices in accordance with a number of embodiments of the invention can be light enough to be carried by an EMT.

Turning now to FIG. 2, a portable ultrasound device in accordance with an embodiment of the invention is illustrated. Portable ultrasound device 200 can have a housing containing circuitry used to perform ultrasound based diagnoses. The outside of the housing can have numerous modifications. The portable ultrasound device 200 can have a power button 210. In several embodiments, the power button 210 is a toggle, a switch, or any other input device as appropriate to the requirements of given applications. The portable ultrasound device 200 can also have one or more input/output ports 220. Input/output ports can be universal serial bus (USB) ports, firewire ports, Ethernet ports, SD card ports, wireless connectors such as Bluetooth or WLAN antennas, and/or any other input/output port as appropriate to the requirements of given applications. In many embodiments, the portable ultrasound device 200 has a control panel 230. In some embodiments, the control panel 230 can be removed to allow access to internal components. A separate panel can also be included in a portable ultrasound device to allow access to internal components. The control panel 230 can have numerous buttons, switches, toggles, and/or a touch-screen interface to allow a user to operate the portable ultrasound device 200. In several embodiments, control panel 230 allows the user to choose the type of test to be performed, to input test parameters, to download/upload data, and to begin/end tests. However, control panel 230 can allow any type of user input as appropriate to the requirements of given applications.

Portable ultrasound device 200 can have a handle 240 to assist in moving the portable ultrasound device 200. In many embodiments, handle 240 is retractable and can be made to lie flush with the portable ultrasound device. In this way, the handle 240 can be made in such a way that it will not interfere with the usage or storage of the device. In a variety of embodiments, the portable ultrasound device 200 has a compartment 250. The compartment 250 can contain ultrasound diagnostic tools such as, but not limited to, transducer assemblies, positioning bands, ultrasound gel pads, and/or any other diagnostic tool and/or medical equipment as appropriate to the requirements of a given application.

In many embodiments, the portable ultrasound device 200 stores at least one transducer assembly. The transducer assembly(s) can be stored in compartment 250. Transducer assemblies can also be stored in holders on the exterior of the portable ultrasound device 200. In numerous embodiments, transducer assemblies include an ultrasound transmitter element, and an ultrasound receiver element. In a variety of embodiments, a coaxial dual-element ultrasound transducer can be used that is capable of performing the functions of both an ultrasound transmitter element and an ultrasound receiver element. In many embodiments, transducer assemblies are single element transducers. The portable ultrasound device can have a test material or pad to serve as a transmission reference media. In numerous embodiments, the test material is stored between the transducer assemblies in such a way that the faces of the transducer assemblies are pressed against the test material. In this way, calibration steps can be performed with a reference media and in a standardized environment.

Portable ultrasound device 200 can have one or more display devices. A display device can be lit. In numerous embodiments, multiple back lights can be used. In some embodiments, a high power backlight and a low power backlight can be used. The low power backlight can be used to indicate that user interaction is needed, and the high power display can be turned off or dimmed. A user can touch the display device to turn the high power backlight to a higher power so the user can more easily view the display. In some embodiments, the user presses a button or uses a toggle to increase the power. In a variety of embodiments, the one or more display devices are LCD screens. In some embodiments, LED screens are used. However, any number of display devices can be used as appropriate to the requirements of a given application. In many embodiments, portable ultrasound devices have one or more speakers to provide audio feedback. As can readily be appreciated, the specific user interface provided by a portable ultrasound device and/or via a portable computer (e.g. a mobile phone) communicating by a portable ultrasound device are largely dictated by the requirements of a given application.

As one can readily appreciate, the dimensions and arrangements of specific components of portable ultrasound device 200 as illustrated in FIG. 2 are by way of example, and the dimensions and arrangement for a portable ultrasound device is not limited by the single embodiment illustrated in FIG. 2. The operation of various portable ultrasound devices in accordance with a number of embodiments of the invention is discussed further below.

Using Portable Ultrasound Devices

In many embodiments, the portable ultrasound device utilizes positioning bands that can house transducer assemblies in a manner that allows for consistent and reliable placement of the transducer assemblies on a patient within a tolerable range. Consistent transducer assembly placement on a patient's body can enable accurate diagnostics.

Figure 3A:
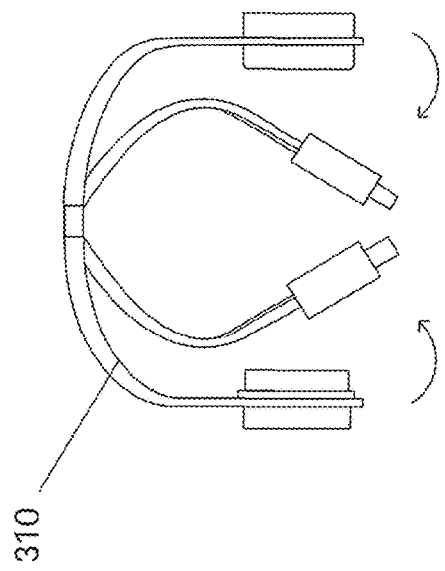
FIGS. 3A-D are renderings of a sequence of operations performed when preparing a portable ultrasound device for use on a patient in accordance with an embodiment of the invention.

Turning now to FIG. 3A, a positioning band configured to be stored within a compartment of a portable ultrasound device is illustrated in accordance with an embodiment of the invention. Positioning band 310 can be stored in compartment 300. In some embodiments, more than one positioning band can be stored in compartment 300. In numerous embodiments, compartment 300 houses transducer assemblies and/or ultrasound gel pads in addition to the positioning band.

Figure 3B:
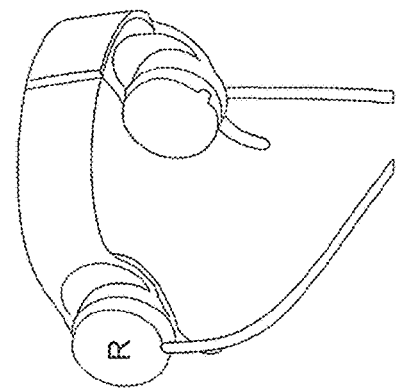
Figure 3C:
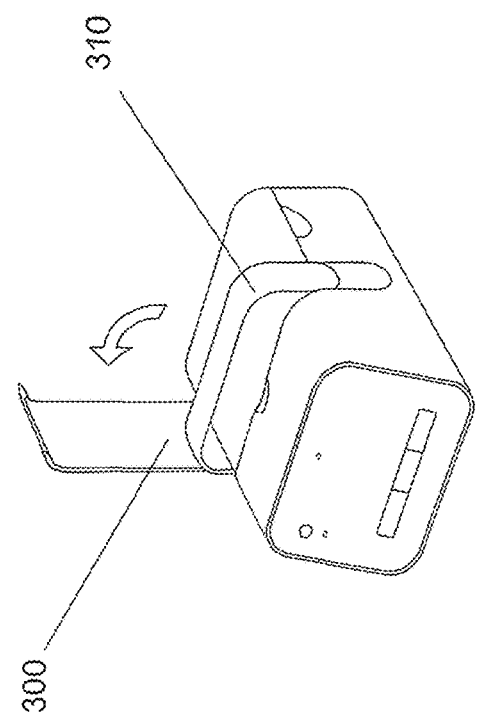
Figure 3D:
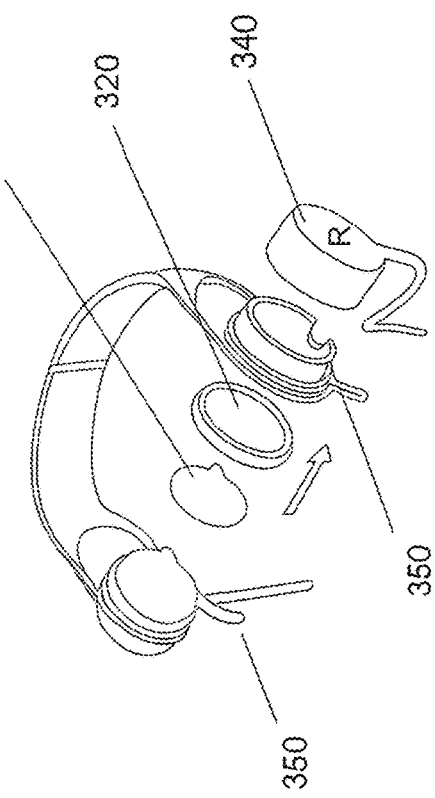

FIGS. 3B-D illustrate the preparation of a positioning band for use in accordance with an embodiment of the invention. Positioning band 310 can be stored in compartment 300 in a more compact, folded form. Positioning band 310 can be unfolded to create a headband shape. Positioning band 310 can be manufactured in such a way that the band will telescope in order to accommodate a variety of patient head sizes. In numerous embodiments, positioning band 310 has transducer assembly holders into which transducer assemblies can be socketed. In many embodiments, positioning band 310 is disposable. Positioning band 310 can be sanitized and/or reused. In a variety of embodiments, a new positioning band 310 can be used for each patient. Transducer assemblies 340 can be categorized into a right side transducer assembly and a left side transducer assembly. In some embodiments, portable ultrasound device has two transducer assemblies, where one is labeled as a right transducer assembly and the other is labeled as a left transducer assembly. Positioning band 310 can also hold ultrasound gel pads 320. In numerous embodiments, ultrasound gel pads 320 have removable covers 330. In a variety of embodiments, ultrasound gel pads similar to those described in U.S. Provisional Patent Application No. 62/452,253 can be utilized. The relevant disclosure from U.S. Provisional Patent Application No. 62/452,253 is hereby incorporated by reference herein in its entirety. Positioning band 310 can have one or more positioning guides 350 to help correctly position the positioning band 310 on the patient. In multiple embodiments, positioning guides 350 are designed to interface with a patient's ear. In numerous embodiments, proper placement of transducer assemblies is at the cranial temporal window of the skull. Positioning guides 350 can increase the likelihood that proper placement is achieved by making incorrect placement uncomfortable and/or inoperable. FIG. 3D is a rendering of a positioning band fitted with transducer assemblies.

Figure 4B:
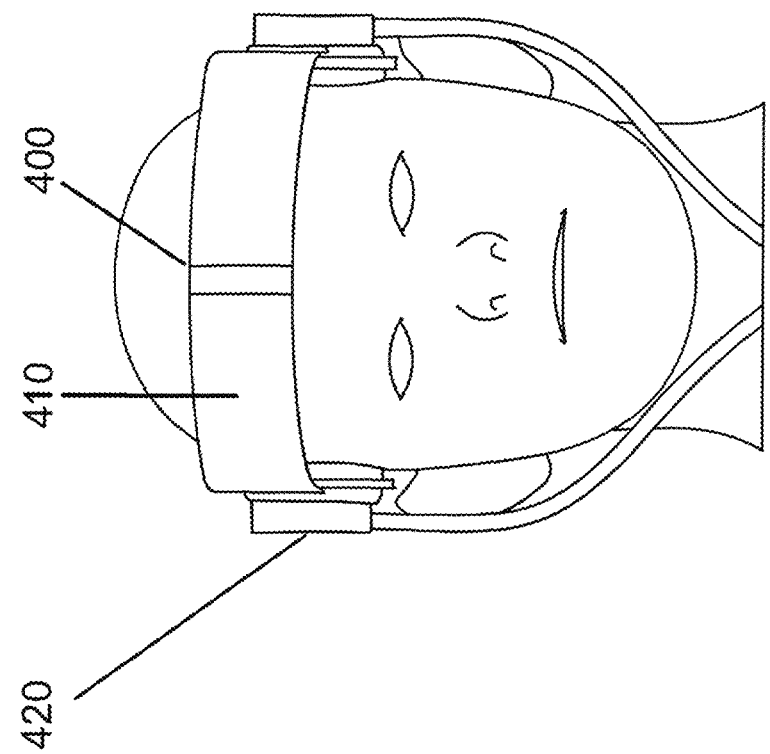
FIGS. 4A-B are rendering of a portable ultrasound device being used on a patient in accordance with an embodiment of the invention.
Figure 4A:
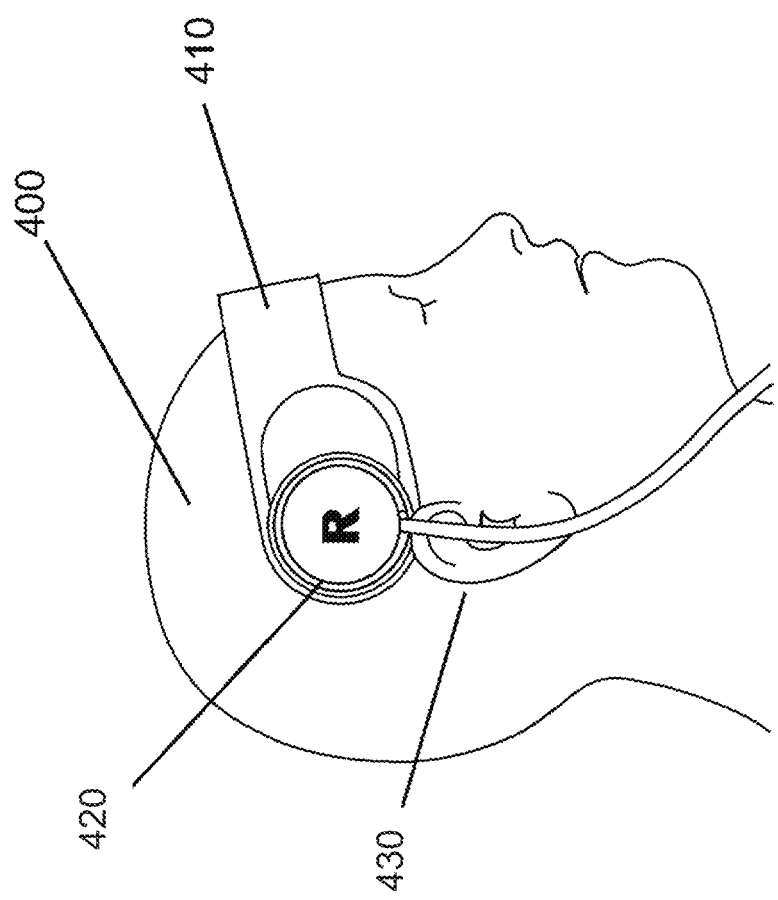

Turning now to FIGS. 4A-B, a positioning band fitted to a patient's head in accordance with an embodiment of the invention is illustrated. In many embodiments, positioning band 410 is placed on patient's head 400 in such a way that the transducer assemblies 420 lie above the patient's ears and the positioning guides 430 do not interfere with placement. In this way, the portable ultrasound device can perform tests based on a known position of the transducer assemblies 420. In a variety of embodiments, positioning band 410 is manufactured in such a way that the portable ultrasound device will not operate when the positioning band is reversed by having features that normally protrude into a gap formed between the band and a patient's head, but if reversed, will lay over the patient's ears and hold the transducer assemblies away from the head. In many embodiments, positioning band 410 is considered reversed when a designated right side of the positioning band 410 is positioned on the left side of the patient's head, and/or a designated left side of the positioning band 410 is positioned on the right side of the patient's head.

While positioning bands have been illustrated in the above figures, positioning bands are not essential for the use of portable ultrasound devices. In many embodiments, transducer assemblies can be placed on a patient without the use of positioning bands. In a variety of embodiments, positioning bands can have different form factors from the form factors illustrated in FIGS. 3A-D, and 4A-B, such as, but not limited to, a cap, a circlet, or any other form factor that aids in the positioning of transducer assemblies as appropriate to the requirements of given applications. In numerous embodiments, two or more transducer assemblies can be held by positioning bands. In numerous embodiments, two pairs of transducer assemblies can be aligned approximately with the centerline of the head, where a first transducer assembly of each pair is on the anterior side of the face, and a second transducer assembly of each pair is on the posterior side of the face, each pair primarily covering a different hemisphere. In a variety of embodiments, ultrasound transducers can be placed on the forehead and the temples of a head. While positioning bands have been illustrated in the above figures as holding two transducer assemblies in specific locations, any number of transducers and any number of locations can be used, including, but not limited to, at least one transducer assembly on the forehead, the back of the head, and/or any other arrangement and number of transducer assemblies as appropriate to the requirements of a given application.

Ultrasound Device Circuitry

Ultrasound device circuitry in accordance with many embodiments of the invention can allow a portable ultrasound device to transmit and receive ultrasound and to translate the received ultrasound signals into medical data. In many embodiments, the ultrasound device circuitry can help determine whether the transducer assemblies are placed correctly. In numerous embodiments, the ultrasound device circuitry can localize the stroke to a specific area of the brain and/or identify the class of stroke that the patient has suffered.

Figure 21:
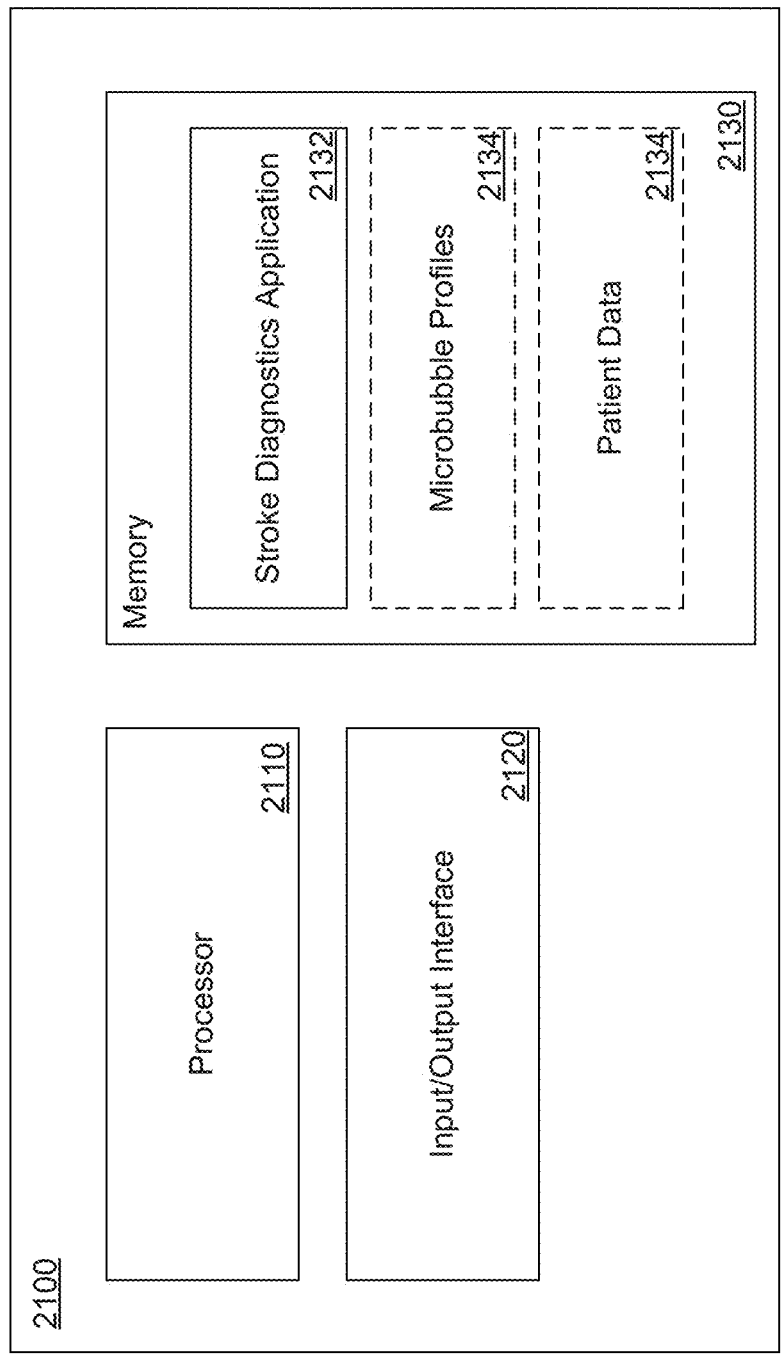
FIG. 21 is a conceptual diagram illustrating a portable diagnostic device in accordance with an embodiment of the invention.

Turning now to FIG. 21, a conceptual diagram for a portable ultrasound device is illustrated in accordance with an embodiment of the invention. Portable ultrasound device 2100 includes a processor 2110. Processors can be any logic unit capable of processing data such as, but not limited to, central processing units, graphical processing units, microprocessors, parallel processing engines, or any other type of processor as appropriate to the requirements of specific applications of embodiments of the invention. Portable ultrasound device 2100 further includes an input/output interface. In numerous embodiments, input/output interfaces are capable of interfacing with other portable ultrasound device circuitry including, but not limited to, displays, ultrasound transducer assemblies, or any other circuitry used by portable ultrasound devices as appropriate to the requirements of specific applications of embodiments of the invention.

Portable ultrasound device further includes a memory 2130. Memory can be implemented using any combination of volatile and/or non-volatile memory, including, but not limited to, random access memory, read-only memory, hard disk drives, solid-state drives, flash memory, or any other memory format as appropriate to the requirements of specific applications of embodiments of the invention. Memory 2130 contains a stroke diagnostics application 2132. Stroke diagnostics applications can direct the processor and any relevant portable ultrasound device circuitry to perform ultrasound diagnostic processes such as, but not limited to, those described below. Memory 2130 can further include microbubble profiles 2134 that describe the harmonic responses of different types of microbubble compositions, and/or patient data 2134 describing clinically relevant information about the patient.

Figure 5:
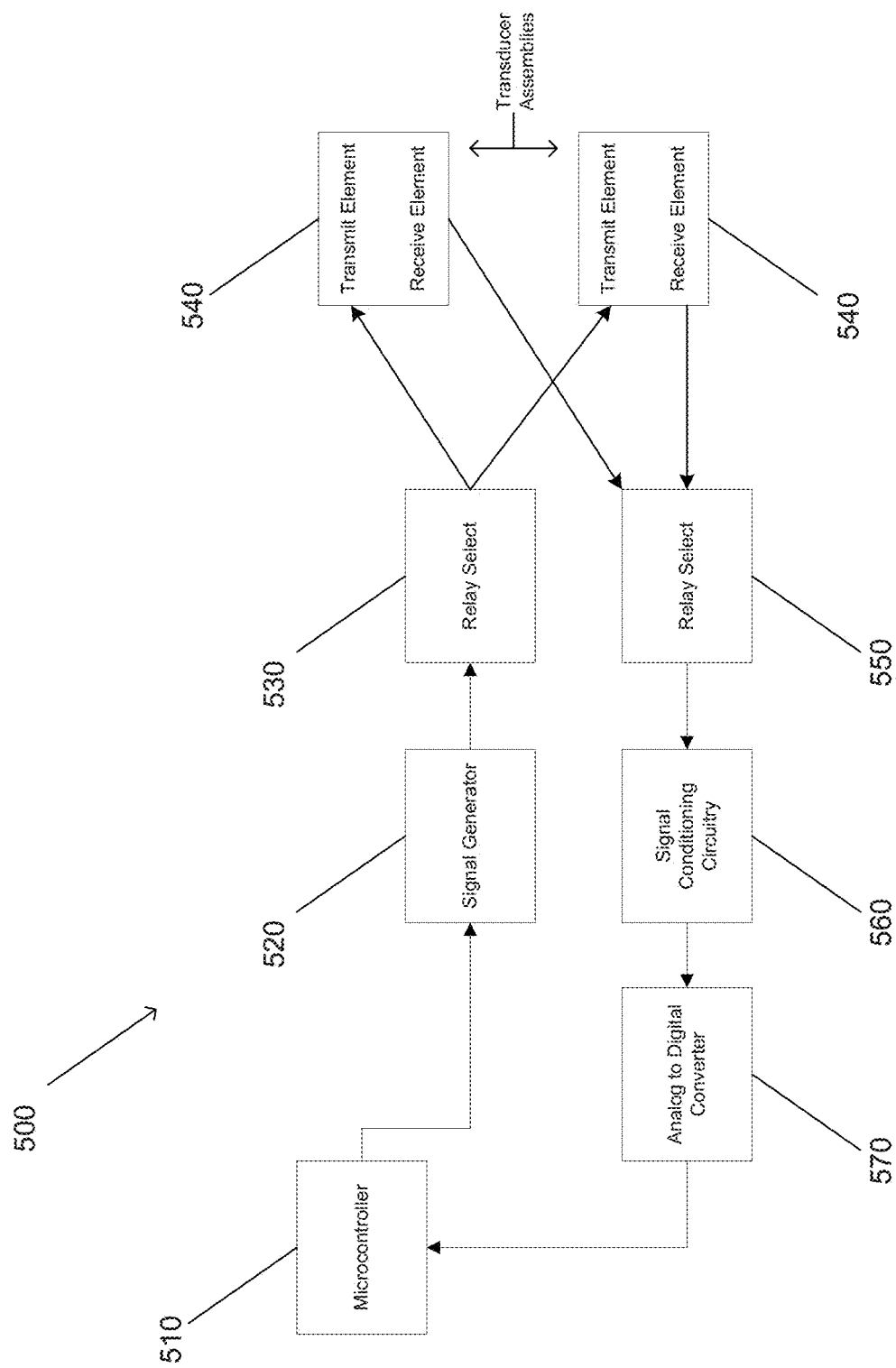
FIG. 5 is a block diagram illustrating the system architecture of a portable ultrasound device in accordance with an embodiment of the invention.

While a conceptual diagram for portable ultrasound devices is discussed above with respect to FIG. 21, portable ultrasound devices can include different configurations of analog and/or digital components to enable the collection of ultrasound data. Turning now to FIG. 5, a block diagram for the circuitry of a portable ultrasound device is illustrated in accordance with an embodiment of the invention. Circuitry 500 includes a microcontroller 510 connected to a signal generator 520. In certain embodiments, the signal generator 520 can generate a sinusoidal signal capable of driving a transducer assembly. In a variety of embodiments, the signal generator 520 can generate a non-sinusoidal signal capable of driving a transducer assembly. In several embodiments, the signal generator 520 is capable of modifying the signal strength and resulting transmitted signal power. In a number of embodiments, the signal generated by the signal generator is dynamically modified based on commands received from the microcontroller to control the output power of the transducer assemblies 540. In certain embodiments, the signal generated by signal generator 520 is conveyed to the transmit element of at least one of a set of transducer assemblies 540 via relays 530. In several embodiments, the relays 530 pass the signal to one of two transducer assemblies 540. Microcontroller 510 can direct the relays 530 to pass the signal to the transmit element of a specified transducer assembly 540.

A second relay 550 can be configured by microcontroller 510 to pass a signal from at least one receive element of transducer assemblies 540. In numerous embodiments, the second relay 550 pass a signal from only one receive element at a time. The signal received by second relay 550 can be passed to signal conditioning circuitry 560. Signal conditioning circuitry can be configured in such a way that the signal can be modified to filter out DC components of the signals. In a variety of embodiments, signal conditioning circuitry 560 amplifies the signal. In numerous embodiments, the signal conditioning circuitry 560 down mixes the received signal to a frequency band that simplifies subsequent signal processing operations. The specific range can be a range at which an analog to digital converter can sample the band limited down sampled signal at a rate equaling or exceeding the Nyquist rate of the down sampled signal (e.g. a rate greater than or equal to twice the highest frequency component of the band limited signal). While the signal conditioning circuitry 560 can filter the signal, additional filtering can occur in the digital domain.

In numerous embodiments, transducer assemblies include at least one ultrasound transducer. In many embodiments, transducer assemblies include a first ultrasound transducer and a second ultrasound transducer. The first and second ultrasound transducers can be mounted in a controlled orientation within the transducer assembly. In a variety of embodiments, the first and second ultrasound transducer are aligned co-axially and co-planar. The first ultrasound transducer can be tuned for receiving ultrasound at a specific transmitting frequency, and the second ultrasound transducer can be tuned for transmitting ultrasound at specific transmitting frequency. In a variety of embodiments, the receiving frequency is 1,100 kHz, and the transmitting frequency range is 220 kHz. However, any number of frequencies, including ranges of frequencies can be used in accordance with the requirements of a given application.

In many embodiments, ultrasound transducers designated for receiving and ultrasound transducers designated for transmitting are separated into different transducer assemblies. Further, the ultrasound transducers can operate bidirectionally, and are not limited to only receiving or transmitting.

The signal conditioning circuitry 560 outputs a signal that is provided to an analog to digital converter 570, which converts the signal from an analog signal to a digital signal. In many embodiments, once the signal is digitized, additional digital filtering can be performed by the microcontroller 510. As one can readily appreciate, a variety of specific circuits can be used to perform the functions described above as appropriate to the requirements of a given application. While any number of circuit configurations can be used as appropriate to the requirements of a given application, a specific example of a portable ultrasound device circuitry is discussed below.

Example Portable Ultrasound Device Circuitry

Figure 6A:
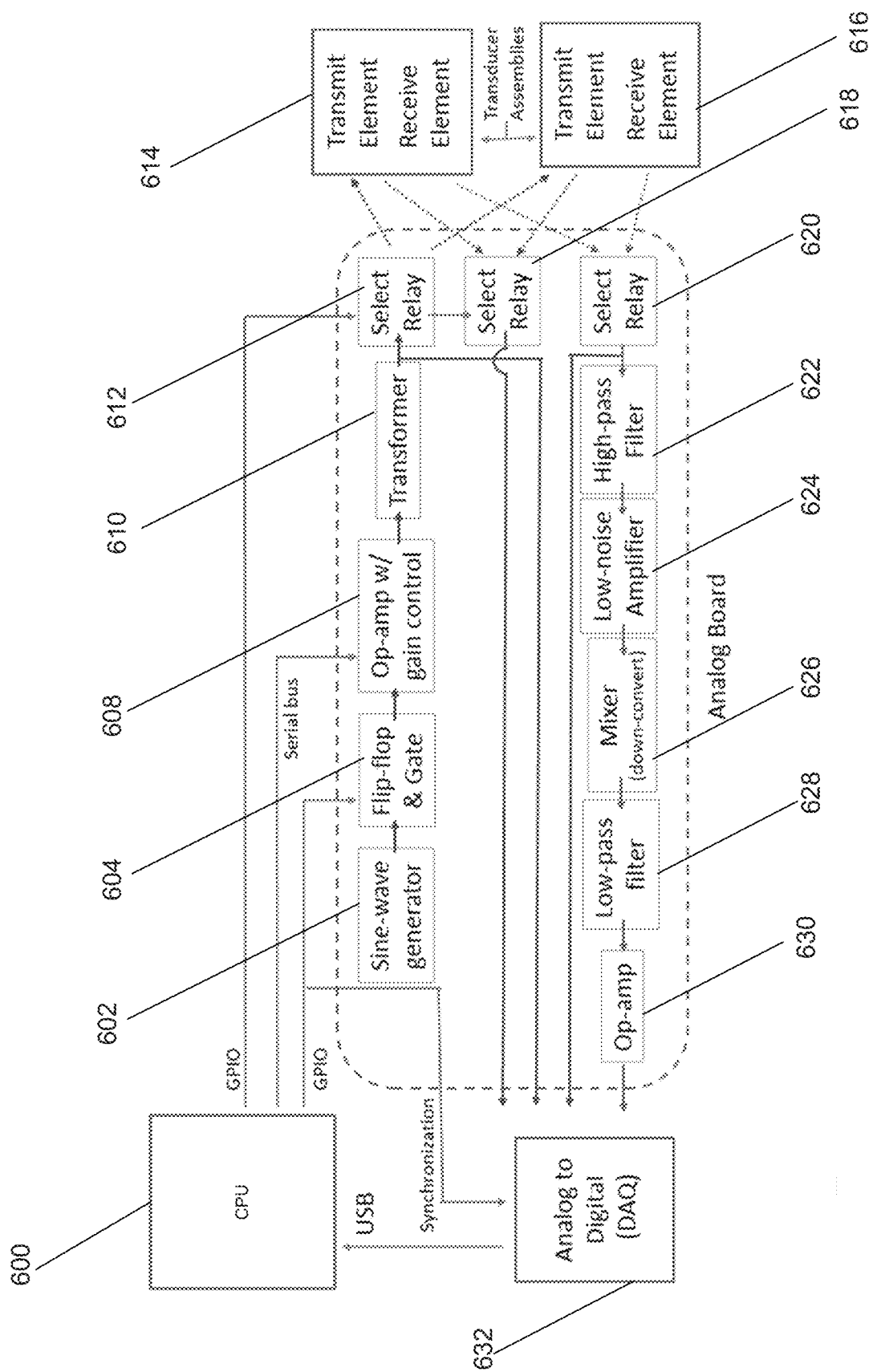
FIG. 6A is a block diagram illustrating a first system architecture of a portable ultrasound device in accordance with an embodiment of the invention.

Turning now to FIG. 6A, example specific circuitry for a portable ultrasound device is illustrated in accordance with an embodiment of the invention. In the illustrated embodiment, the signal generator includes a sine-wave generator 602 and a flip-flop connected to an AND gate 604. As noted above, the combination of the flip-flop connected to an AND gate 604 and the sine-wave generator 602 can serve to control the timing of the transmission of pulses generated by the sine-wave generator 602 so that pulses commence and end at zero-crossings of the signal generated by the sine-wave generator 602. In many embodiments, a microcontroller can select whether the transmission starts with a rising zero-crossing or a falling zero-crossing in order to transmit pulses that are 180 degrees out of phase. A CPU 600 can initiate transmission of a pulse of ultrasound via the AND gate by causing the flip-flop to pass a signal from the sine-wave generator to an operational amplifier 608. In the illustrated embodiment, the operational amplifier includes a gain control mechanism. The CPU 600 can utilize the gain control mechanism to control the output power of the transmitted signal. In numerous embodiments, the signal is passed through a transformer 610 to provide impedance matching with transducer assemblies which will transmit the signal. The CPU 600 can direct which transmit element will transmit the signal using a first select relay 612. Transmit elements can be components of transducer assemblies. The first select relay 612 can chose between a first transducer assembly 614 and a second transducer assembly 616. A second select relay 618 can be utilized by the CPU 600 to receive a signal from one of the transducer assemblies to monitor the transmission of the signal.

Figure 6B:
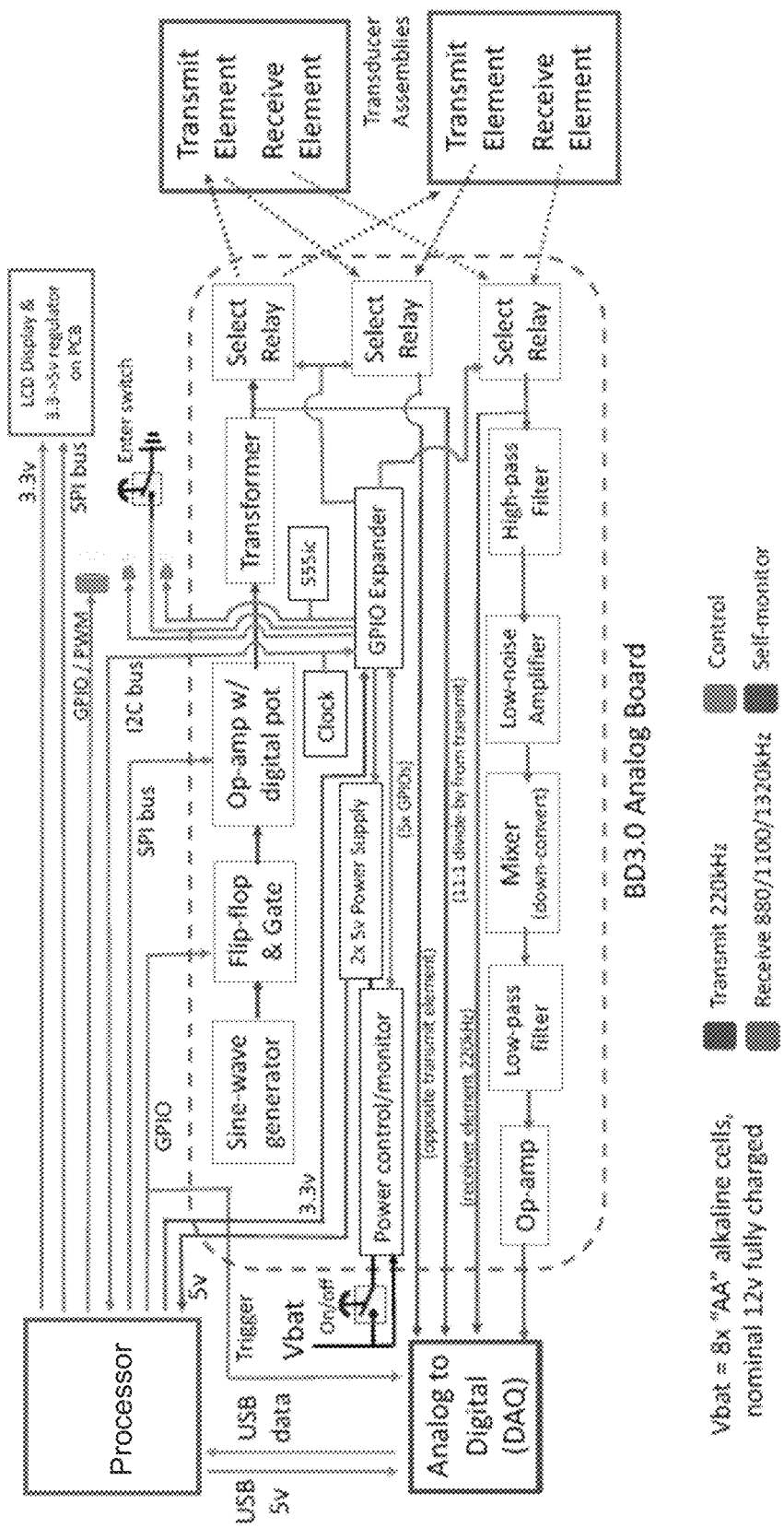
FIG. 6B is a block diagram illustrating a second system architecture of a portable ultrasound device in accordance with an embodiment of the invention.
Figure 6C:
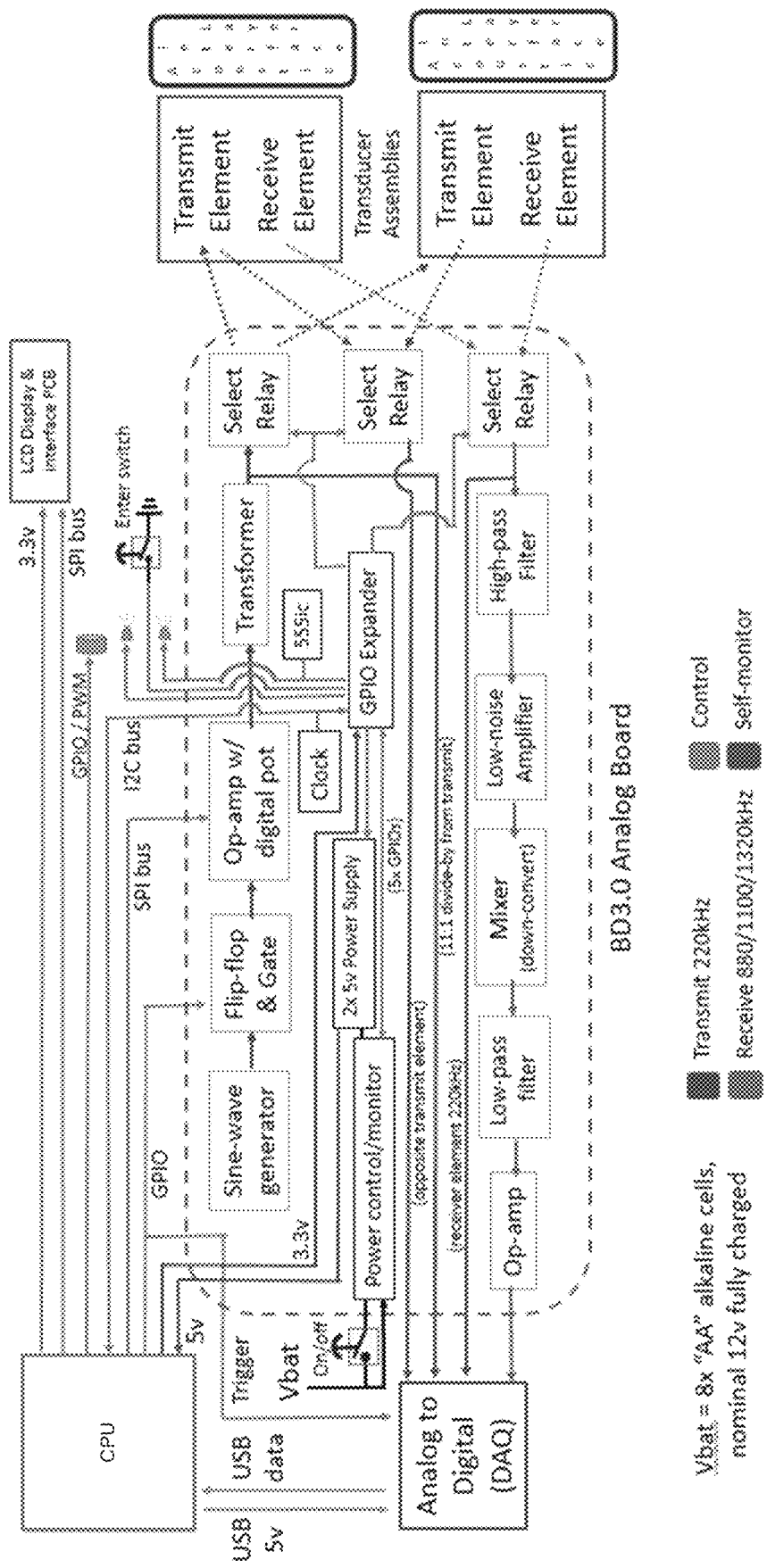
FIG. 6C is a block diagram illustrating a third system architecture of a portable ultrasound device in accordance with an embodiment of the invention.

A third select relay 620 can be used to receive a signal from at least one of the transducer assemblies. As can readily be appreciated, a single relay, multiple relays, and/or a variety of relays can be used as appropriate to the requirements of given applications. The third select relay 620 can transfer the received signal to a high-pass filter 622 in order to remove any low frequency components of the signal. In numerous embodiments, a capacitor inlined to remove DC bias. The high-passed signal can be provided to a low-noise amplifier 624 in order to boost the signal without introducing significant amounts of additional noise. The amplified signal can be down-converted using a mixer module 626, and provided to a low-pass filter 628 to band limit the signal eliminating high frequency noise prior to digitization. The signal can be provided as an input to an operational amplifier 630 before being provided as an input to an analog to digital converter 632. The digital form of the signal can be stored in a memory by the CPU 600 for additional digital processing. Although specific circuits are described above with respect to FIGS. 5, 6A, 6B, and 6C for generating and processing signals in an ultrasound device, any number of specific circuit configurations can be used in an ultrasound device as appropriate to the requirements of given applications in accordance with various embodiments of the invention. In many embodiments, single components can perform the tasks that can be done by multiple components. Not all components are necessary for the usage of portable ultrasound devices. For example, additional implantations using specific circuits are illustrated in FIGS. 6B and 6C. Portable ultrasound devices can have circuitry that enables the output of the transducer assemblies to be regulated.

Regulating Transducer Assembly Output

Components of portable ultrasound devices can be used to control the start of ultrasound transmission in such a way that there is low and predictable latency between the "start" signal and the actual beginning of the transmission signal. In numerous embodiments, receiving elements are triggered to begin receiving ultrasound by the "start" signal. Low and predictable latency can enable ultrasound transmission that is highly synchronized for time/spatial precision. It can be important to know the precise start of a transmitted signal as well as the frequency and amplitude.

Analog systems often cannot immediately transmit a target frequency and amplitude without time to stabilize. This period is called the "ring up" period. Similarly, a "ring down" period can occur when a transmission is turned off. When the beginning and end of a transmitted signal is at the zero voltage (crossover) point in the waveform, the transient disturbance of the circuit can be minimized, and the circuit can rapidly move to a desired amplitude with increased frequency conformance. In a variety of embodiments, the ultrasound device circuitry allows for the start of transmission to occur randomly at any phase angle, and the first cycle of the transmission has frequency content that is variable depending on the phase angle at the start. In several embodiments, however, phase angle is controlled to create ultrasound device circuitry in which the ring up and ring down characteristics of the transmitted signal are repeated from one transmission to the next. In certain embodiments, phase angle is controlled using a flip-flop inline between an oscillating source and the amplification section of the transmit circuit. The flip-flop can act to allow the sinusoidal signal generated by the oscillator circuit through only at a zero crossing. In this way, the signal that is amplified and transmitted to the transducer assembly can always start at a zero crossing of the phase angle, providing predictable ring up and ring down behavior. Ring up and ring down periods can be experienced by microbubbles as they are exposed to and removed from ultrasound stimulation, respectively. As is discussed further below, the ability to predict the ring up and ring down period can provide significant benefits with respect to the use of signal timing in functions including (but not limited to) stroke localization. Portable ultrasound devices can be used for a variety of medical purposes, such as, but not limited to, stroke detection and localization are described below.

Methods for Operating Portable Ultrasound Devices

Portable ultrasound devices can perform a variety of operations to allow for accurate data generation. In many embodiments, portable ultrasound devices automatically perform a variety of operations prior to generating diagnostic support data.

Figure 7:
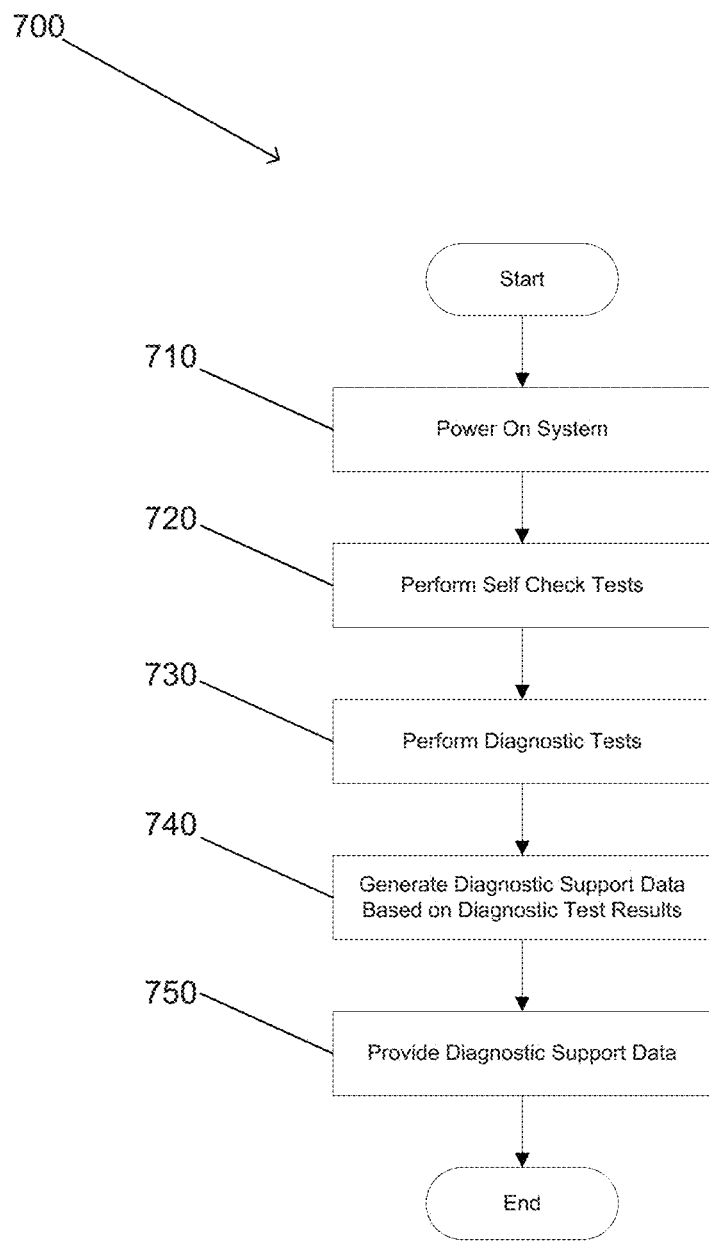
FIG. 7 is a flow chart illustrating a process for using a portable ultrasound device in accordance with an embodiment of the invention.

Turning now to FIG. 7, a process for using a portable ultrasound device is illustrated. The process 700 for using a portable ultrasound device includes powering (710) the system. Powering (710) on a portable ultrasound device can be achieved by pressing a switch, a button, or any form of power toggle as appropriate to the requirements of given applications. In many embodiments, the portable ultrasound device performs (720) self-check tests to verify that the device is in working condition and is safe to use. The portable ultrasound device can further perform (730) diagnostic tests and generate (740) diagnostic support data based on diagnostic test results. The diagnostic support data can be provided (750) in any number of ways including (but not limited to) display via a user interface and/or audio output. In numerous embodiments, the diagnostic support data is transferred to a computer and/or server system. In many embodiments, the diagnostic support data can be output to a storage device similar to those described in FIG. 1 via the input/output port.

While a method for using portable ultrasound devices has been outlined above, one of ordinary skill in the art would recognize that portable ultrasound devices have numerous applications which may require reordering of steps, removal of steps, and/or addition of steps as appropriate to the requirements of given applications. The following sections will generally discuss processes for generating suggested diagnoses and performing diagnostic tests based on microbubble harmonic responses. The diagnostic processes then serve as a backdrop for discussing the importance of various self-check tests, calibration steps, and additional diagnostic processes that can be performed by portable ultrasound devices in accordance with various embodiments of the invention.

Using Microbubbles as Acoustic Markers

Microbubbles can be used with portable ultrasound devices as acoustic markers. When microbubbles are exposed to ultrasound, they can resonate and generate harmonic signal responses. Microbubble harmonic responses can be detected by portable ultrasound devices, and portable ultrasound devices can determine the position of microbubbles based on the detected harmonic responses. In some embodiments, microbubbles are administered as a bolus. In many embodiments, microbubbles are administered gradually using an IV. In a variety of embodiments, microbubbles are administered orally. In some embodiments, microbubbles are administered as an inhalant Microbubbles can be administered to the patient multiple times while the portable ultrasound device is in use. The portable ultrasound device can alert the user that it is ready for microbubbles to be administered to the patient. The alert can be visual using a display or a light, and/or auditory using a speaker. In numerous embodiments, medical grade microbubbles are used for the diagnostic process. Microbubbles can have characteristic signal responses per unit of applied acoustic pressure and a characteristic latency for the signal response. Because microbubbles are carried by the blood, the microbubble harmonic responses can be used to measure blood movement in the brain.

In numerous embodiments, a portable ultrasound device monitors whether microbubbles have been introduced too early during "baseline" measurements. Early administration of microbubbles can be detected by checking for at least one frequency and/or amplitude marker that is a reliable indicator of the presence of microbubbles (e.g. a harmonic of the ultrasound frequency that is typically detected in the presence of microbubbles). In some embodiments, the portable ultrasound device checks whether or not microbubbles have been introduced properly during a test measurement by checking for characteristic microbubble harmonic responses and/or amplitude marker that is known to be consistently present when microbubbles are present. In a variety of embodiments, the formulation of the microbubbles introduced can be derived by measuring their characteristic microbubble responses.

Bolus injection of microbubbles is typically characterized by a rapid rise in microbubble concentration in the bloodstream and tissue for several seconds, and then receding from the bloodstream relatively quickly. The entry and rise of concentration of microbubbles is called a "wash-in," whereas the process of receding is called a "wash-out." Wash-in typically can begin within a few seconds of injection, and can reach a peak within 5 and 10 seconds. However, depending on the rate of blood flow, it can be a longer or shorter period of time. Wash out occurs over a longer period than wash-in to get the majority of microbubbles out of the patient's system, but can be longer or shorter depending on the rate of blood flow and condition. While not all microbubbles might not be washed out after this period, the portable ultrasound system can count the microbubbles as receded once the measured concentration has been reduced past a certain threshold. In some embodiments, the threshold is 70% of a peak harmonic amplitude observed during and/or following wash-in, however any threshold can be used as appropriate to the requirements of a given application. However, a wide variety of thresholds can be used as appropriate to the requirements of specific embodiments of the invention. The amount of reduction in observed harmonics within a received signal associated with the presence of microbubbles can be obtained by comparing the peak of the detected microbubble wash-in with the baseline acoustic measurements. Further, because the wash-in, wash-out period is relatively short, the portable ultrasound device can detect the commencement of a wash-in event. In this way, the portable ultrasound device need not rely on a user input to determine when an injection of microbubbles is administered.

By measuring patterns of blood flow, a diagnosis can be calculated. Wash in/wash out rates for each hemisphere can be compared to each other. In many embodiments, comparison between hemispheres can be used instead of default threshold measurements. Methods for generating diagnostic support data are discussed below.

Generating Diagnostic Support Data Using Portable Ultrasound Devices

Portable ultrasound devices can generate diagnostic support data based on diagnostic test results. The processor of the portable ultrasound device can be configured by an ultrasound diagnostic application to acquire diagnostic test data from diagnostic tests and process said diagnostic test data to produce diagnostic support data. The processor can transmit the diagnostic test data to a computer or server system to be processed to produce diagnostic support data. Diagnostic support data can include a calculated diagnosis. Calculated diagnoses can be generated based on recognizable patterns associated with known injuries. Patterns can be recognized by measuring microbubble harmonic responses within the patient's blood. Several methods for pattern recognition are discussed further below.

When a large bleed occurs the ambient pressure in the hemisphere often rapidly elevates above normal and initially there can be excessive blood flowing into a cavity of the hemisphere without flowing properly into the surrounding tissue. Later, the average pressure can elevate even more substantially and the excessive blood flow into the cavity subsides and drops below normal due to the elevated pressure. In this scenario, the blood in the cavity tends to stay "trapped" for a long time. Microbubbles can be injected into the blood supply early in the bleed, causing a large concentration of microbubbles to flow into the cavity and be trapped there while surrounding tissue has a lower concentration. As pressure builds, the microbubble amplitudes can be reduced compared to the expected normal amplitudes based on concentration. As concentration increases, the signal response is typically highest for the region of trapped blood compared to other regions in that hemisphere.

Microbubbles can also be injected into the blood supply late in the bleed. In a late bleed, less blood is likely to flow into the cavity and the microbubble concentration can drop to a level comparable to or slightly higher than the surrounding tissue. Therefore, the microbubble signal responses across the hemisphere are expected to be more uniform, but at a lower concentration due to the impairment of blood supply based on elevated pressure. The described signatures can be used to diagnose a brain hemorrhage, and can be used to diagnose the stage of the bleed. In some embodiments, a portable ultrasound device will attempt to determine if there is a bleed before checking if there is a blockage.

In many embodiments, the diagnostic support data includes a classification of the type of stroke detected. An ischemic stroke can be signified by a relatively normal response pattern on one side of the brain, and a blockage pattern in the opposite hemisphere. Hemorrhagic strokes can be signified by a lack of blockage patterns, but detection of some high volumes of blood and some lower volumes of blood in different regions of the hemispheres can indicate a bleed.

In many embodiments, the portable ultrasound device can detect when microbubbles are destroyed in the acoustic field. If microbubbles are destroyed in the acoustic field, then replenishment time can indicate that there is a hemorrhage. Since blood is not being replenished quickly in the high-pressure volume outside the bleed, then after microbubbles in the volume are destroyed, microbubble signatures ramp up more slowly in the area of high-pressure. Further, replenishment time can be an indicator of perfusion condition, and can be measured by varying the ultrasound pulse repetition time to determine the necessary time for microbubbles to repopulate the sonicated volume. In some embodiments, replenishment analysis can be performed without destroying microbubbles. A second bolus of microbubbles can be introduced after wash-out of the first bolus in order to mimic the replenishment effect described above.

Figure 16A:
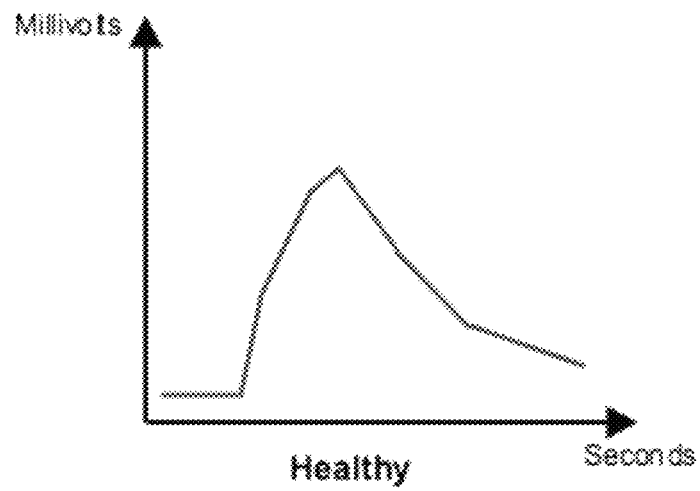
FIG. 16A is a chart illustrating acoustic response signals from a healthy hemisphere in accordance with an embodiment of the invention.
Figure 16B:
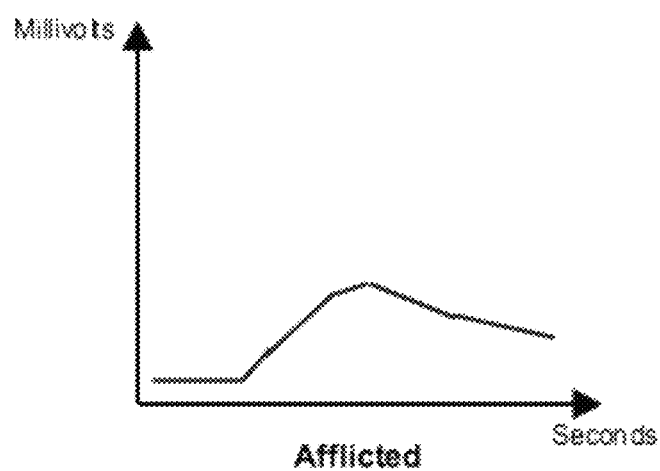
FIG. 16B is a chart illustrating acoustic response signals from an afflicted hemisphere in accordance with an embodiment of the invention.
Figure 16C:
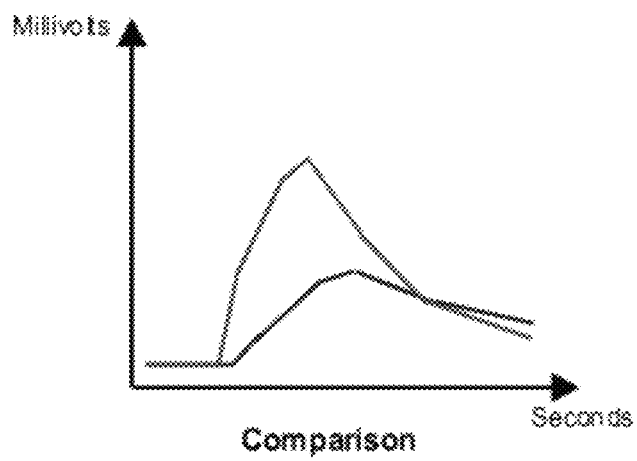
FIG. 16C is a chart illustrating acoustic response signals from an afflicted hemisphere and a healthy hemisphere compared to each other in accordance with an embodiment of the invention.

While several injury patterns are described above, portable ultrasound devices can be used to associate any number of injury patterns to specific injuries as appropriate to the requirements of given applications. Many injury patterns can be detected with appropriate configuration of a portable ultrasound device in accordance with various embodiments of the invention based on the patterns of blood flow resulting from the injuries. By way of example, a comparison of an idealized standard healthy brain pattern vs. an injured brain pattern is illustrated in FIGS. 16A-C in accordance with an embodiment of the invention. FIG. 16A illustrates a harmonic response signal over time from a healthy hemisphere. FIG. 16B illustrates a harmonic response signal from an afflicted/injured hemisphere in accordance with an embodiment of the invention. FIG. 16C illustrates a comparison of the harmonic response signals of FIGS. 16A and 16B.

Figure 11:
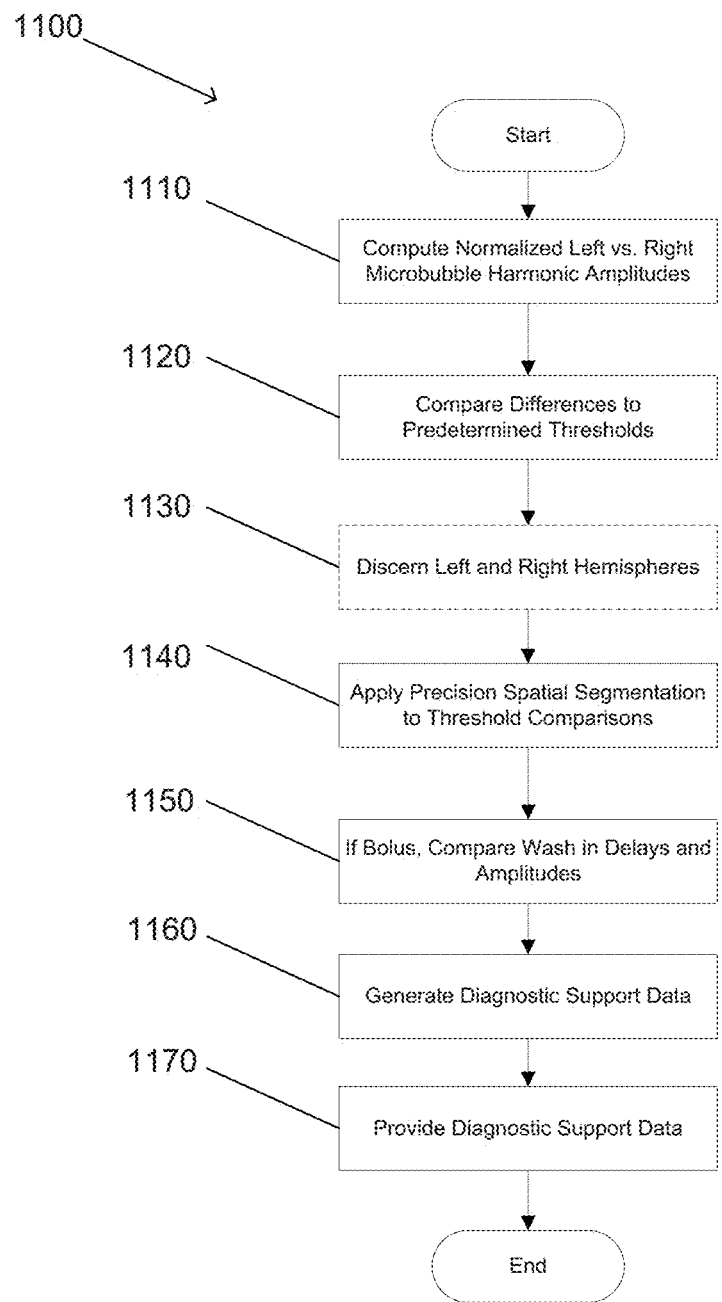
FIG. 11 is a flow chart illustrating a process for generating and providing diagnostic support data using a portable ultrasound device in accordance with an embodiment of the invention.

Turning now to FIG. 11, a process for generating diagnostic support data based on diagnostic test data is illustrated in accordance with an embodiment of the invention. Process 1100 includes computing (1110) normalized left vs. right microbubble harmonic amplitudes. Normalized microbubble harmonic amplitudes can be compared (1120) to predetermined thresholds, and in some embodiments, left and right hemispheres of the brain are discerned (1130). Precision spatial segmentation can be applied (1140) to the threshold comparisons in order to localize injuries. If microbubbles were administered as a bolus, then the wash in delays and amplitudes can be compared (1150). Generating (1160) diagnostic support data including a suggested diagnosis based on the results of the processed diagnostic tests. Portable ultrasound devices can provide (1170) diagnostic support data generated based on the diagnostic tests. Portable ultrasound devices can provide diagnostic support data. In some embodiments, the suggested diagnosis is provided via a display. However, the diagnostic support data can be provided in a variety of methods, including, but not limited to, storing data on a non-transient machine readable medium, uploading data to a computer, uploading data to a server system, uploading data to a mobile phone, and/or communicating data via any other information transfer protocol as appropriate to the requirements of a given application.

While a specific process for generating diagnostic support data is described above, one of ordinary skill in the art would recognize that there are numerous ways to generate diagnostic support data from diagnostic tests and analysis in accordance with the requirements of given applications. Examples of processes for generating diagnostic support data from different diagnostic tests are described below.

Generating Diagnostic Support Data from Contralateral Receiving Diagnostic Tests Different diagnostic tests can produce different types of data. Contralateral describes a configuration in which two objects are on the opposite side of the body from each other. For example, if an ultrasound transmitter element is placed on the right side of a patient's head, and an ultrasound receiver element is placed on the left side of the patient's head, the transmitter and receiver would be contralaterally oriented. In contrast, if both the transmitter and receiver elements were on the right side of the patient's head, they would be ipsilaterally oriented. Diagnostic tests can be performed using contralateral, ipsilateral, or any other type of configuration, such as, but not limited to, multi-point arrangements including transmitters on the center-line of the body, as appropriate to the requirements of specific applications of embodiments of the invention. However, regardless of the type of diagnostic test performed, microbubble harmonic signals will be dominated by the signal generated by microbubbles on the hemisphere of the brain closest to the transmitting transducer assembly when the focal point of peak negative pressure is designed to be at or near the interface of the transducer assembly. In numerous embodiments, this is caused by the high energy focal area of the transducer assembly overlapping large blood vessels closest to the transducer assembly. This phenomenon is referred to as "transmit side bias" of the microbubble signal profile. Transmit side bias can be achieved by inducing a beam shape and placing transducer assemblies on the head to approximately align with large blood vessels. Transmit side bias can be utilized in generating diagnostic support data. A diagnostic test contralateral receiving approach uses a transmitting transducer assembly and a separate receiving transducer assembly. Methods for performing the contralateral receiving approach are described in a below section.

Figure 17A:
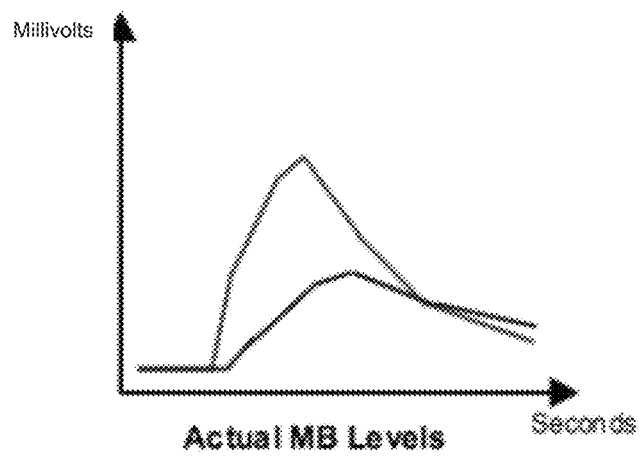
FIG. 17A is a chart illustrating acoustic response signals in accordance with an embodiment of the invention.
Figure 17B:
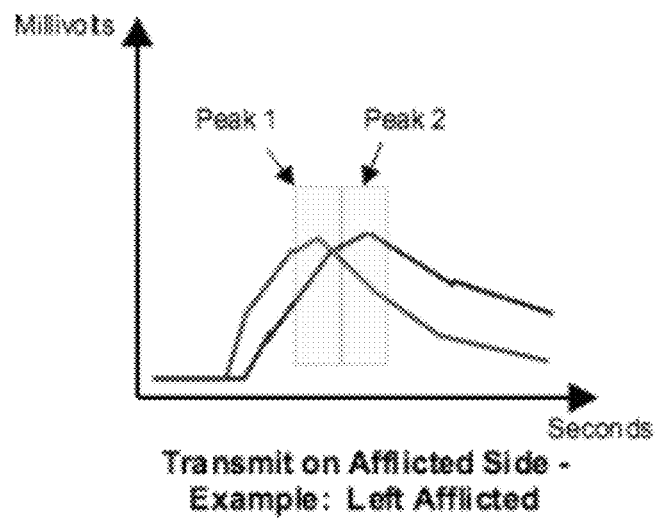
FIG. 17B is a chart illustrating exemplary acoustic response signals from an afflicted hemisphere and a healthy hemisphere using a contralateral receiving approach in accordance with an embodiment of the invention.
Figure 17C:
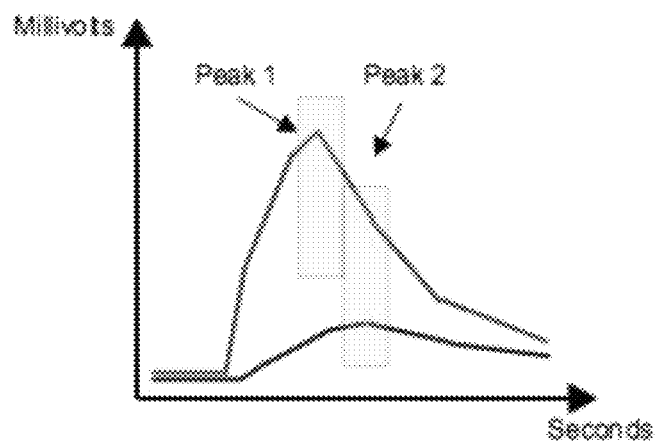
FIG. 17C is a chart illustrating exemplary acoustic response signals from an afflicted hemisphere and a healthy hemisphere using a contralateral receiving approach in accordance with an embodiment of the invention.

Turning now to FIG. 17A, actual microbubble levels in an exemplary brain with an afflicted left hemisphere and a healthy right hemisphere are illustrated in accordance with an embodiment of the invention. In comparison to FIG. 17A, FIG. 17B illustrates received harmonic response signals received when transmitting on the healthy side of the brain in accordance with an embodiment of the invention. FIG. 17C illustrates received harmonic response signals when transmitting on the afflicted side of the brain in accordance with an embodiment of the invention.

In the example illustrated in FIG. 17B, due to transmit side bias, when transmitting on the afflicted side, the signal levels from the afflicted hemisphere will be raised, and the signal levels from the healthy hemisphere will be lowered from their actual levels. Similarly, in the example illustrated in FIG. 17C, when transmitting on the health side, the signal levels from the healthy hemisphere will be raised, and the signal levels from the afflicted hemisphere will be lowered compared to their actual levels. The net signal received by a transducer assembly is a combination of what is illustrated in FIGS. 17B and 17C. Of note is the "double peak" profile which is expected to occur at minimum when transmitting on the afflicted side. Presence of a double peak can indicate a stroke because of the delayed wash-in on one side of the brain. However, in addition to the knowledge of the double peak, the two graphs in FIGS. 17B and 17C can be compared with respect to amplitude in order to refine and confirm results. The increase in amplitude of peak one when transmitting on the right (healthy) side indicates that it is the healthy hemisphere, whereas the decrease in amplitude of peak two indicates that it is the afflicted hemisphere. Further, by averaging the graphs from transmitting on both sides, a graph similar to the actual microbubble signal as illustrated in FIG. 17A can be generated.

In cases where the second peak is difficult to identify, the search space can be refined by looking for an "elongated" peak time-shifted from the first peak. The elongated peak can be further identified by a more gradual decline in the slope of the curve following the second peak. Further, the width of the curve is generally wider as compared to the height of the peak when transmitting from the side of the afflicted hemisphere. A boundary can be identified between the peaks as the point where the amplitude neither rises nor falls. This neutral point can represent the boundary between the part of the curve that is dominated by the healthy hemisphere responses and the part of the curve that is dominated by the afflicted side responses.

In numerous embodiments, when the second peak is difficult to identify, once the first, temporally earlier peak has been identified, the rolling average of the continuous slope of the curve moving forward can be analyzed for the presence of the second, temporally later peak using "shoulder detection." In a variety of embodiments, shoulder detection involves identifying potential changes in the slope after the first peak consistent with the potential presence of a second peak. Once such a location has been identified, the portion of the curve after the location that is the same length as the distance from the first peak to the identified location can be analyzed for the presence of any other potential second peaks. In numerous embodiments, if there is no second peak within that distance, it can be assumed that the second peak has been located. However, any distance to the right of the located second peak can be analyzed as needed. In numerous embodiments, when transmitting on the afflicted slide, the second peak will be higher, the slope between the two identified peaks will be shallower, and the slope to the right of the second peak will be more negative than when compared to a transmission on the unaffiliated side.

In cases where the afflicted side has so little perfusion that the signal is effectively undetectable, a case can occur where only "healthy" curves are observable. This does not prevent the ability to detect and localize a stroke. If the increase in signal when switching from left transmitting to right transmitting is too large to be explained by side-to-side tolerance ranges, then the portable ultrasound device can conclude that the signals are only being generated from one side.

While specific methods for generating diagnostic support data using a contralateral receiving approach are discussed above with respect to a specific example, the contralateral receiving approach can be utilized with any number of brain afflictions in accordance with the requirements of a given application. Portable ultrasound devices are not restricted to only using one approach. A method of generating diagnostic support data using an ipsilateral receiving approach is discussed below.

Generating Diagnostic Support Data from Ipsilateral Receiving Diagnostic Tests

The ipsilateral receiving approach involves using a single transducer assembly to both transmit and receive per hemisphere. The ipsilateral receiving approach in combination with time-boxing of received signals enables the portable ultrasound device to analyze only certain regions of the brain. In numerous embodiments, time-boxed signals are portions of a signal that occur between two points in the time-domain of the signal. In numerous embodiments, the two points correspond to the time at which the signal describes a region of interest. However, unwanted harmonics are generally generated at the boundary of the flesh and skull as ultrasound begins to propagate. These harmonics introduce noise at a point very close to the transmitting transducer assembly. Because the transmitting transducer assembly is also the receiving transducer assembly in the ipsilateral receiving approach, received signals can be noisy with unwanted harmonics from the skull boundary.

Figure 18A:
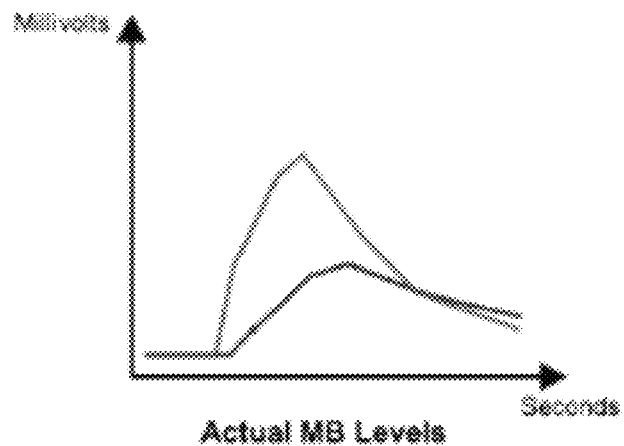
FIG. 18A is a chart illustrating acoustic response signals in accordance with an embodiment of the invention.
Figure 18B:
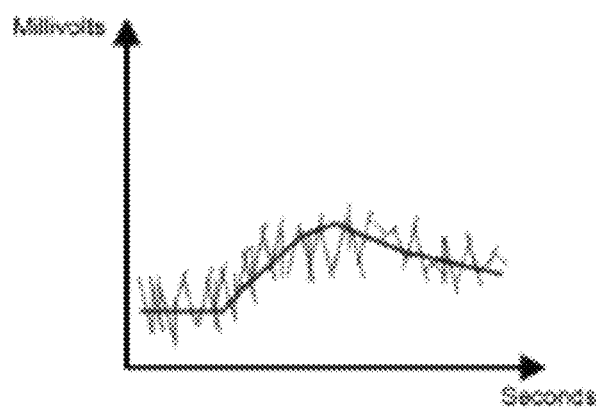
FIG. 18B is a chart illustrating exemplary acoustic response signals from an afflicted hemisphere using an ipsilateral receiving approach in accordance with an embodiment of the invention.
Figure 18C:
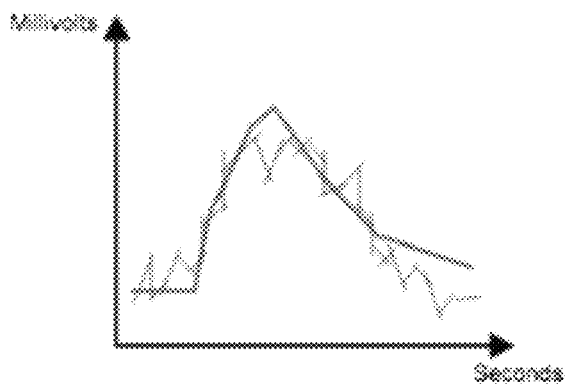
FIG. 18C is a chart illustrating exemplary acoustic response signals from a healthy hemisphere using an ipsilateral receiving approach in accordance with an embodiment of the invention.

Turning now to FIG. 18A, actual microbubble levels in an exemplary brain with an afflicted left hemisphere and a healthy right hemisphere are illustrated in accordance with an embodiment of the invention. FIG. 18B illustrates the signal received from only the left hemisphere when transmitting on the left side using time-boxing in accordance with an embodiment of the invention. The ipsilateral signal is distorted by unwanted harmonic noise. Similarly, FIG. 18C illustrates the signal received from only the right hemisphere when transmitting on the right side using time-boxing in accordance with an embodiment of the invention. Again, the ipsilateral signal is distorted by unwanted harmonics.

Unwanted harmonics can be mitigated to an extent by using techniques described below. In addition, a combined ipsilateral/contralateral receiving approach can be utilized in order to mitigate weaknesses of both approaches.

Combined Ipsilateral/Contralateral Receiving Approach

Figure 19A:
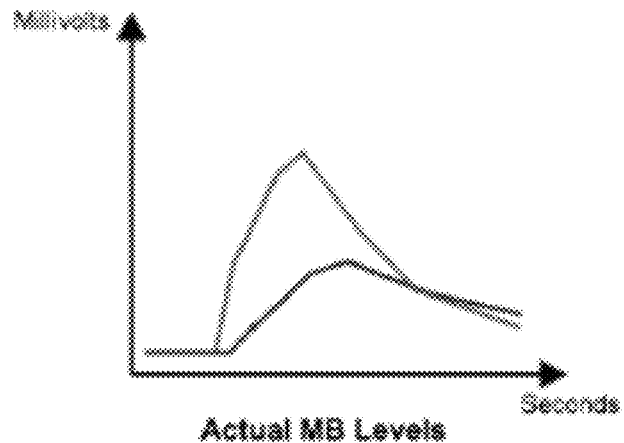
FIG. 19A is a chart illustrating acoustic response signals in accordance with an embodiment of the invention.

Turning now to FIG. 19A, actual microbubble levels in an exemplary brain with an afflicted left hemisphere and a healthy right hemisphere are illustrated in accordance with an embodiment of the invention. In order to obtain an estimate of the actual blood flow, both the ipsilateral and contralateral receiving approaches can be used in tandem. In many embodiments, sets of interleaved measurements are obtained by transmitting and receiving signals both ipsilaterally and contralaterally. In numerous embodiments, the periodicity of the measurements are sufficiently fast so that the plots over time can be generated for transmissions on both the right and left transducer assemblies with both ipsilateral and contralateral measurements. Portable ultrasound devices can generate these plots with resolution no worse than one measurement per second for each plot. The contralateral measurements can be analyzed for the presence of double peaks. As noted above, the presence of double peaks indicates a stroke condition somewhere in the brain. Using techniques similar to those described above with respect to the contralateral approach, an afflicted hemisphere can be identified.

Figure 19B:
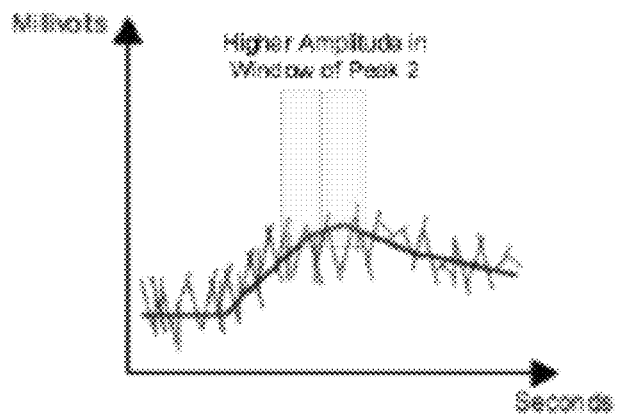
FIG. 19B is a chart illustrating exemplary acoustic response signals from an afflicted hemisphere using a combined ipsilateral/contralateral receiving approach in accordance with an embodiment of the invention.
Figure 19C:
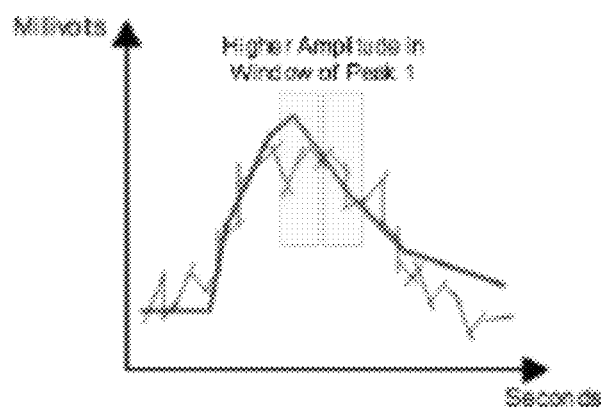
FIG. 19C is a chart illustrating exemplary acoustic response signals from a healthy hemisphere using a combined ipsilateral/contralateral receiving approach in accordance with an embodiment of the invention.

From the contralateral data, the time-box for each peak can be identified. These time-boxes can be overlaid onto ipsilateral data plots. FIG. 19B illustrates an exemplary ipsilateral plot for an afflicted hemisphere with overlaid time-boxes generated from contralateral data in accordance with an embodiment of the invention, and FIG. 19C illustrates an exemplary ipsilateral plot for a healthy hemisphere overlaid with time-boxes generate from contralateral data in accordance with an embodiment of the invention. In numerous embodiments, it is difficult to locate peaks using ipsilateral data alone due to unwanted harmonics. By comparing the amplitudes of the signal within the time-boxes for each of the right side and left side ipsilateral plots, further confirmation of which hemisphere is afflicted can be generated. In many embodiments, for each ipsilateral plot, the time-box containing a peak will show an average amplitude higher than the average amplitude of the time-box not containing a peak despite any distortion or inaccuracy created by unwanted harmonics because the unwanted harmonics tend to be relatively stable for short periods of time such as the time between time-boxes of the peaks.

In certain situations, ipsilateral data on one side can have a very low amplitude resulting in a signal that is indistinguishable from the noise of the unwanted harmonics. This can be caused by a severe stroke condition. Under severe stroke conditions, the contralateral plots may not show a double peak because the signal levels on the afflicted side are too low. As a result, contralateral plots can appear to reflect a healthy brain. However, the ipsilateral plot would show a stroke condition based on amplitude comparisons, but the analysis may not have sufficient confidence. In order to resolve the disparity, several steps can be taken. In many embodiments, based on the amplitude of the contralateral data and the healthy side ipsilateral data plus the maximum expected tolerances between the two sides, the minimum signal level of the side with a low signal is calculated as if the side with the low signal level were healthy. The minimum expected signal level can be compared to the levels of noise to determine if the minimum signal level can be completely masked under the noise floor. In numerous embodiments, if the minimum signal level is still expected to appear above the noise floor, but it does not, then a likely stroke on that side is determined. In a variety of embodiments, if the minimum healthy signal level is expected to be masked by the noise floor, then the outcome is ambiguous, and a repeat test can be recommended.

While certain processes for generating diagnostic support data have been discussed above, any number of different methods, including, but not limited to, performing the above processes with different ordering can be used in accordance with the requirements of a given application. As noted above, not only can diagnostic support data indicate which hemisphere is afflicted, but portable ultrasound devices can determine the type of stroke a patient is afflicted by. Methods for determining the type of stroke a patient is afflicted by are described below.

Differentiating Hemorrhagic Versus Ischemic Strokes

There are two main different types of strokes. Hemorrhagic strokes occur when there is a bleed occurring in the brain, often due to a bursting of a vein or artery. Ischemic strokes occur when there is a blockage in an artery or vein resulting in a region of the brain suffering from inadequate blood supply. In numerous embodiments, portable ultrasound devices can determine when there is a bleed vs a blockage using many different methods.

In many embodiments, discrimination between a bleed and a blockage can be achieved using time-pattern analysis. In general, bleeds can present as a brief drop in vascular pressure and flow of blood into cranial space as blood flows out of the arterial vessel and pools in the interstitial space. As excess blood flows, intracranial pressure rises. The rise in pressure impedes the blood flow into the cranial space after pressure is above normal levels. This pressure level is generally achieved within minutes of onset, but can vary with bleed amount. The volume of blood in the cranial space and the corresponding rise in pressure continues for a long period of time. In many cases, this can be hours. Based on this sequence of events, it is expected that the blood supply into the cranial space in the afflicted hemisphere will briefly be higher than normal, then will pass through a normal range, and then become lower than normal.

Throughout the process, the perfusion to the tissue is reduced and blood flow out of the hemisphere is correspondingly reduced. Because the bleed creates a pooled blood volume in the cranial space, blood containing microbubbles post bolus injection mixes with pooled blood from the hemorrhage event prior to flowing out. As a result the pooled blood will accumulate a partial concentration of microbubbles for a significant period of time. As such, the wash-out pattern of a hemorrhage will be significantly longer than a healthy brain.

Figure 20:
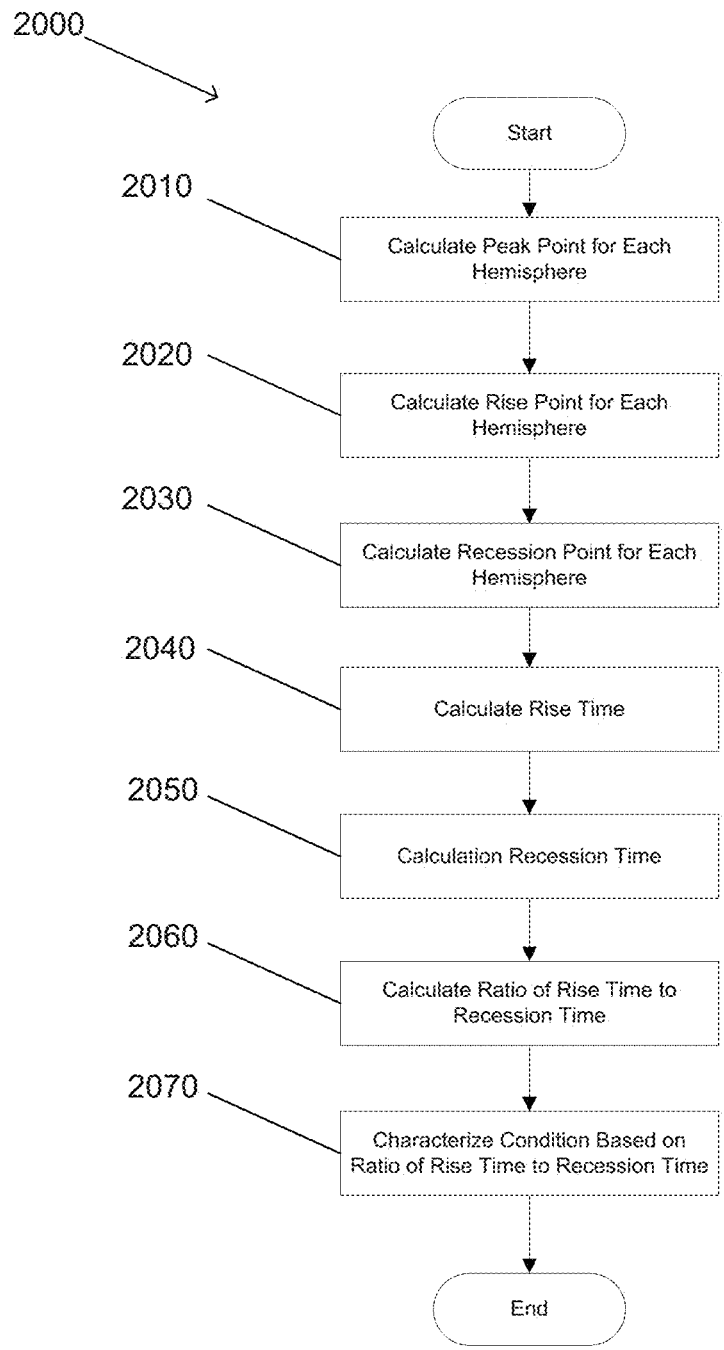
FIG. 20 is a flow chart illustrating a process for differentiating a bleed from a blockage in accordance with an embodiment of the invention.

Turning now to FIG. 20, a process for performing a time-pattern analysis for determining a bleed vs. a blockage is illustrated in accordance with an embodiment of the invention. Process 2000 includes, for the wash-in/wash-out pattern of each hemisphere, calculating (2010) the peak point, calculating (2020) the rise point, and calculating (2030) the recession point for each hemisphere. The peak point is the point on the wash-in/wash-out curve (harmonic response measurements) at which the harmonic response peaks. The rise point can be defined as an arbitrary point along the rising edge of the wash-in/wash-out curve before the peak point. In many embodiments, the rise point can be arbitrarily set at 50% of the peak. However, any arbitrary rise point can be chosen in accordance with the requirements of a given application. The recession point can be defined as an arbitrary point along the falling edge of the wash-in/wash-out curve after the peak point. In numerous embodiments, the recession point can be arbitrarily set at 50% of the peak. However, any arbitrary recession point can be chosen in accordance with the requirements of a given application.

Process 2000 further includes calculating (2040) rise time as the difference from the rise point to the peak point, and calculating (2050) recession time as the difference from the peak point to the recession point. In many embodiments, the value of the rise time plus the value of the recession time is called the half peak full width parameter. In numerous embodiments, higher pressures are indicated by a smaller half peak full width parameter. A ratio between the rise time and the recession time can be calculated (2060). The rise/recession ratio can be used to characterize (2070) the brain condition. In many embodiments, the recession time will be longer during a bleed, meaning the rise/recession ratio will be lower than for a blockage or a healthy condition. In the event of a blockage, the rise time can be elongated. In numerous embodiments, a predetermined threshold ratios can be used to determine which type of stroke has occurred. In numerous embodiments, the predetermined threshold can be changed via an input to the portable ultrasound device.

In addition to time-pattern analysis, cranial pressure can be used to determine whether a bleed or a blockage has occurred. Microbubbles can have acoustic responses that are dependent upon pressure. In many embodiments, pressure influenced acoustic responses change depending on the type of microbubble. In many embodiments, subharmonics and/or superharmonics are influenced by pressure. However, in numerous embodiments, normal harmonic frequencies are influenced by pressure. By measuring changes in harmonic response known to be caused by pressure changes, bleeds and blockages can be differentiated. As noted above, bleeds result in changes in intracranial pressure, whereas blockages can have their own distinct patterns of pressure when compared to healthy hemispheres.

In many embodiments, the changes in harmonics can be used to determine cerebral perfusion pressure (difference between the mean arterial pressure and the intracranial pressure). In numerous embodiments, the cerebral perfusion pressure is inversely correlated with mean transit time (i.e. the time it takes for the microbubbles to wash-in/wash-out). In a variety of embodiments, low cerebral perfusion pressure indicates a bleed. Mean transit time can also be correlated to the half peak full width parameter described above. Higher pressures can cause smaller half peak full width values. By way of example, if an arbitrary healthy brain is assigned a half peak full width parameter of 100 units, if one hemisphere has a value of 100 and the other has a value of 40, the affected side has elevated pressure indicating a bleed. If one hemisphere has a value of 100 and the other has a value of 140, the affected side has reduced pressure indicating a blockage. In numerous embodiments, general blood pressure measurements from a blood pressure cuff can be incorporated into calculations Further, spatial patterns can be used to differentiate between bleeds and blockages. Harmonic responses across spatial slices of each hemisphere can be determined, and the resulting slices from each side can be compared. Methods for performing spatial segmentation can be found below. If there is a known pattern for a healthy brain for each slice is known, then a blockages and bleeds can be differentiated. When a blockage occurs, there can be a reduction in signal for each slice in a hemisphere consistent across each slice in that hemisphere because blockages tend to impact blood flow across an entire hemisphere. In the event of a bleed, a certain region can have significantly more variability as blood pools in different locations in the hemisphere. The difference between consistency and variability as contrasted to a healthy pattern can be used to distinguish a bleed versus a blockage.

While numerous methods of differentiated bleeds and blockage, any number of methods, including a combination of any of the above methods can be used in accordance with the requirements of a given application. Further, as noted above, higher quality diagnostic support data can be generated in the absence of unwanted harmonics. Methods for reducing unwanted harmonics are discussed below.

Reducing Unwanted Harmonics

There are numerous ways portable ultrasound devices can be used that reduce the amount of unwanted harmonics. In many embodiments, pulse inversion is utilized to measure and detect unwanted harmonic signals in order to filter them out. Under a pulse inversion scheme, a first pulse of ultrasound can be transmitted, and then shortly after, a second pulse can be transmitted such that the second pulse is 180 degrees out of phase with the first pulse. As a result, unwanted harmonics from the first pulse will be 180 degrees out of phase with the unwanted harmonics from the second pulse. Microbubble harmonics will not be cancelled out because microbubble harmonics do not have high correlation between their phase angle and the transmission phase. In some embodiments, microbubble composition is chosen based on their harmonic properties to further reduce the correlation. Using this technique, unwanted harmonics can be identified and filtered out of the return signals. In many embodiments, odd harmonics are fully cancelled out, where even harmonics are doubled in amplitude when the signals are added together. However, by comparing the signals before and after the application of pulse inversion, the doubled even harmonics can be filtered out. In numerous embodiments, the fundamental signal being transmitted by the transducer assembly is at 220 kHz. In this situation, odd harmonics such as 1,100 kHz (the fifth harmonic) is cancelled out, whereas the 880 kHz (the fourth harmonic) and 1,320 kHz (the sixth harmonic) harmonics are doubled. In a variety of embodiments, specific circuitry that enables transmission of ultrasound at a specific phase can be incorporated into to portable ultrasound devices to enable pulse inversion. In many embodiments, the phase angle can be modified in order to reduce unwanted harmonics and to increase the amount of energy that penetrates the skull.

A system that approximates pulse inversion using signal processing can also be utilized. In many embodiments, the portable ultrasound device is configured to determine the amplitudes of the unwanted harmonics independent of the microbubble harmonics after every individual pulse. In many embodiments, each pulse is approximately 50 microseconds, and the data being received is a time series lasting approximately 160 microseconds. In numerous embodiments, the data being received is a time series lasting a time approximately equal to the addition of the pulse transmit time, the time for the signal to cross the entire brain, and the ring up period of the microbubbles. However, any length of pulse and time series can be used as appropriate to the requirements of a given application. Amplitudes can be determined by measuring the reflected fundamental frequency which is correlated to the amplitudes of the received unwanted harmonics. Phase angles of the unwanted harmonics can be measured by analyzing time-boxed slices of data at the beginning of the time series prior to the microbubble harmonics being received. Under a 50/150 microsecond scheme, this period is approximately the first 20 microseconds. If data collected during this period is inaccurate, the phase angle relationship can be determined by using the phase angle of the reflected fundamental frequency as a proxy. Phase angle can further be determined by transmitting at random phase angles and averaging the responses to achieve consistency in unwanted harmonics. Using the amplitudes and phase angles of the unwanted harmonics, the unwanted harmonics can be filtered out of the total received signal to reflect only the microbubble harmonics of interest.

In many embodiments, transducer assembly positioning can be used to reduce unwanted harmonics. Transducer assemblies can be arranged in such a way that the transmit and receive transducers are separated in a configuration where the spatial orientation of the transmit field and receive field are known. In numerous embodiments, transmitted ultrasound is mostly contained in a directional field. A receiving transducer assembly can be positioned in such a way that it is not directly in, or not in, the transmitting transducer assembly's ultrasound field. Harmonic responses generated by microbubbles are generally emitted in random directions. As such, the receiving transducer assembly will still receive the desired harmonic responses, while reducing unwanted harmonics that are directional, such as harmonics reflected from the skull boundary. In many embodiments, receiving transducer assemblies can be arranged in such a way that they detect harmonics primarily from one hemisphere, while remaining outside or on the periphery of the transmitted ultrasound field.

Portable ultrasound devices can use time-boxing to reduce unwanted harmonics. In many embodiments, specific segments of received ultrasound signals have reduced unwanted harmonics due to the different parts of the head that the ultrasound is traversing. For example, for the first 40 microseconds after transmission of ultrasound by a transmitting transducer assembly, no ultrasound may have reached the receiving transducer assembly. Approximately the next 10 microseconds can contain unwanted harmonics originating from the skull boundary. The next 40 microseconds can contain mixed signals from microbubble harmonics and unwanted harmonics from various sources. The following 60 microseconds can contain predominantly microbubble harmonic signals. While specific times have been discussed in the above example, any number of microseconds or range of microseconds may constitute an appropriate estimate of different signal responses depending on the patient, environmental factors, and equipment used. In many embodiments, portable ultrasound devices can estimate appropriate time-boxing points based on test signals.

Time-boxing can be used to clean up signals and/or speed up analysis by processing only valuable signal data. In numerous embodiments, the skull boundary harmonic responses extracted from the appropriate time-box can be used to demix the signal of the next time-box containing mixed signals. In this way, the signal in the mixed time-box can be cleaned. Further, by time-boxing received signals, unwanted harmonics generated from the interface between the transducer assembly and the patient (for example air bubbles trapped in the gel) can be ignored or otherwise utilized to indicate that there are problems at the interface.

While pulse inversion and signal processing techniques are discussed above with specific reference to an ipsilateral approach, pulse inversion can be used in any number of receiving approaches, including, but not limited to contralateral receiving approaches, or combined ipsilateral/contralateral receiving approaches. Accuracy of microbubble harmonic response analysis can be greatly increased by determining a normalized microbubble harmonic amplitude. Methods for normalizing microbubble harmonic amplitudes are described below.

Normalizing Microbubble Harmonic Amplitudes

A baseline harmonic amplitude can be calculated by a portable ultrasound device. Because each patient can have a different cranial thickness, different brain morphology, different brain density, or a number of other biometric idiosyncrasies, harmonic amplitudes may be different across different patients. In many embodiments, calculating baseline harmonic amplitudes allows the portable ultrasound device to detect abnormal brain morphologies. In numerous embodiments, the portable ultrasound device can compensate for abnormal brain morphologies.

Normalized microbubble harmonic amplitudes can be compared to predetermined thresholds, including, but not limited to, baseline thresholds. Establishing predetermined thresholds can be difficult, and there are multiple ways to determine the thresholds. One method can include performing measurement tests on cadavers to determine how closely values measured differ between the two hemispheres of the brain when both sides are perfused with solutions of similar microbubble concentrations. By performing this test on a statistically significant sample size, statistical calculations can determine the amount of margin necessary in order to be highly confident that nearly all heads would fall into the resulting range. However, there are many ways that these threshold values can be determined in accordance with the requirements of given applications.

In many embodiments, the portable ultrasound device maintains data describing at least one baseline harmonic response. By comparing acquired diagnostic support data describing the location of microbubble responses across the brain of the patient to the baseline harmonic responses acquired in the absence of microbubbles, normalized microbubble harmonic amplitudes can be identified.

The portable ultrasound device can store one or more profiles of microbubble characteristics which correspond to microbubbles administered to the patient. Profiles of microbubble characteristics can include, but are not limited to, signal responses per unit of applied pressure, latency for the signal response, predetermined thresholds, or any other microbubble characteristic as appropriate to the requirements of given applications. In a variety of embodiments, the user can input which microbubbles are being administered. Although several methods for normalizing microbubble harmonic amplitudes have been described above, one of ordinary skill in the art would recognize that there are numerous ways to normalize microbubble harmonic amplitudes in accordance with the requirements of given applications.

Localizing Brain Injury

In order to classify a left and right hemisphere, knowing the total width of the brain can be useful. Head size can be calculated by the portable ultrasound device. In a variety of embodiments, a first transducer assembly can send a test ping across the patient's skull. Based on the time the test ping was received by the second transducer assembly placed on the opposite side of the skull, the distance between the transducer assemblies can be calculated. The distance between the transducer assemblies can provide an estimate of the size of the patient's skull. In some embodiments, a single transducer assembly can send a test ping using a transmit element across the patient's skull and measure the time for the reflection of the ping to be picked up by the receive element of the single transducer assembly. The time between the transmission of the test ping and receiving the reflection of the test ping can allow the portable ultrasound device to calculate the size of the patient's skull.

In many embodiments, a portable ultrasound device can discern between the right and left hemispheres of a brain based on the travel time of ultrasound signals. In some embodiments, hemisphere responses can be assigned based on the determination of a center line. The center line can be determined as the point at which a signal from one transducer assembly has traveled half the distance to a contralateral transducer assembly. In numerous embodiments, a sawtooth wave, or any other wave with a smooth ramp can be used to discern the right and left hemispheres. Waves with smooth ramps and defined peaks can allow for accurate measurements of propagation time (e.g. time from transmission of a signal peak to a peak detection at a receiver).

In a variety of embodiments, the peak amplitude focal distance of the transmit element of a transducer assembly can be used to distinguish between signals from the different hemispheres. In many embodiments, the portable ultrasound device smoothly ramps up the peak voltage and monitors for the first indication of microbubble signals. The first occurrence of microbubble signals is located approximately at the focal distance of the transducer assembly. In a variety of embodiments, the focal distance is approximately 40 mm. However, the focal distance of a transducer assembly can be modified to be any distance from the face of the transducer assembly. At the focal length of the transducer assembly, the beam of ultrasound will be at a higher intensity. The tolerance around the distance measurement can be a function of how "sharp" the shape of the peak is at the focal distance, how repeatable the voltage threshold is for microbubble excitation, and/or how repeatable the focal distance is from transducer assembly to transducer assembly. In this way, portable ultrasound devices can discern between the left and right hemisphere.

In many embodiments, precise measurement of the time for signals to breach the center line of the patient's head in ipsilateral configuration is determined by transmitting ultrasound across the head. The portable ultrasound device can calculate head symmetry based on the travel time of the ultrasound pulse across the head. In numerous embodiments, the travel time of the ultrasound pulse across the head is identical to the round-trip travel time to the centerline for the ipsilateral approach. In a variety of embodiments, the measurements can be taken in the presence of microbubbles which allows the portable ultrasound device to calculate the time necessary for microbubble excitation and algorithmic detection.

Further, subharmonic microbubble responses and/or superharmonic microbubble responses can be used to localize brain injury. The difference in harmonics across hemispheres can be utilized to estimate intracranial pressure. In numerous embodiments, superharmonics and/or subharmonics can be normalized based on received normal harmonic responses.

While specific methods of discerning hemispheres have been described above, any number of methods can be used to assign a left and right hemisphere using a portable ultrasound device in accordance with the requirements of given applications. By determining left and right hemispheres, brain injuries can be localized to a specific side of the brain. However, to further localize brain injuries, precision spatial segmentation can be performed. Methods for performing precision spatial segmentation are discussed below.

Performing Precision Spatial Segmentation

Portable ultrasound devices can apply precision spatial segmentation to the threshold comparisons. The frequency of return signals using a portable ultrasound device can have a spatial resolution on the order of 1 mm. Frequencies on this order can allow for segmentation of each hemisphere of the brain into subregions, and each subregion can be compared to its mirror subregion in the opposite hemisphere. In many embodiments, a suggested diagnosis can be determined for each subregion. In this way, localized injuries such as blockages or bleeds of small arteries can be detected. Further, because middle cerebral artery (MCA) blockages impact nearly the entire hemisphere, and other afflictions such as bleed or blockage of smaller arteries have a degree of localization, MCA blockage can be determined at the exclusion of bleed and/or blockage of a smaller artery.

In numerous embodiments, precision spatial segmentation can be performed using a synchronized transmit/receive method. In order to calculate where in the tissue a return signal originates from, the travel time of the signal can be used. The more precisely the travel time can be determined, the more precisely the location of the signal can be calculated. Precision and/or accuracy of measurements such as travel time can be achieved using calibration processes and self-check tests. Processes for improving precision and/or accuracy are discussed further below.

In order to measure the travel time, various methods can be used. In many embodiments, the method includes recording an accurate timestamp when the start of transmission of ultrasound occurs, and recording accurate timestamps in conjunction with each data point recorded for the return signal. In a variety of embodiments, the method includes capturing the transmitted signal in the same data acquisition channel that has an "enable" line for the start of data acquisition. The control line that is used to start the transmission can be connected to the enable line of the start of data acquisition. In numerous embodiments, at least the first data sample will still not have a voltage consistent with a received signal, but when the receive signal is acquired and is detected, the time between the start of the received signal and the first data point (at the start of transmission) can be accurately calculated.

In many embodiments, calculated travel time is used to time-box the received signal into slices. Slices are portions of the signal that correspond to the harmonic responses between two points in the brain. Slices can describe harmonic responses of any region from the spatial resolution of the transducer assembly to the size of the brain. In many embodiments, slices are standardized to 1 cm. However, in numerous embodiments, while the first slice (i.e. from the face of the transducer assembly to 1 cm away) is 1 cm, each subsequent slice may be 1 cm larger in such a way that the start point is always the face of the transducer assembly. In this way, slices of increasing size can be analyzed until an abnormality is detected, and the last centimeter added can be assumed to be the location of the injury within the brain. Further, in a variety of embodiments, each slice can be masked by the previous slice in order to observe only the harmonic responses present at that location.

While several methods for precision spatial segmentation have been described above, one of skill in the art would appreciate that there are a variety of ways to perform precision spatial segmentation using a portable ultrasound device in accordance with the requirements of given embodiments. Further, while several methods of generating diagnostic support data have been described above, the diagnostic tests that the diagnostic support data can be based on are numerous. Processes for performing many diagnostic tests using a portable ultrasound device are described below.
Performing Diagnostic Tests Using Portable Ultrasound Devices Portable ultrasound devices in accordance with many embodiments of the invention can be used to perform diagnostic tests on patients. In many cases, it is difficult to detect and classify strokes, and to localize the stroke event to a particular area of the brain. It is common for medical professionals to use magnetic resonance imaging (MRI) or an x-ray computed tomography (CT) scan to detect and localize strokes. Portable ultrasound devices can use microbubbles as an acoustic markers to track blood flow in conjunction with at least one transducer assembly to effectively detect, classify, and localize strokes in a patient.

Figure 9:
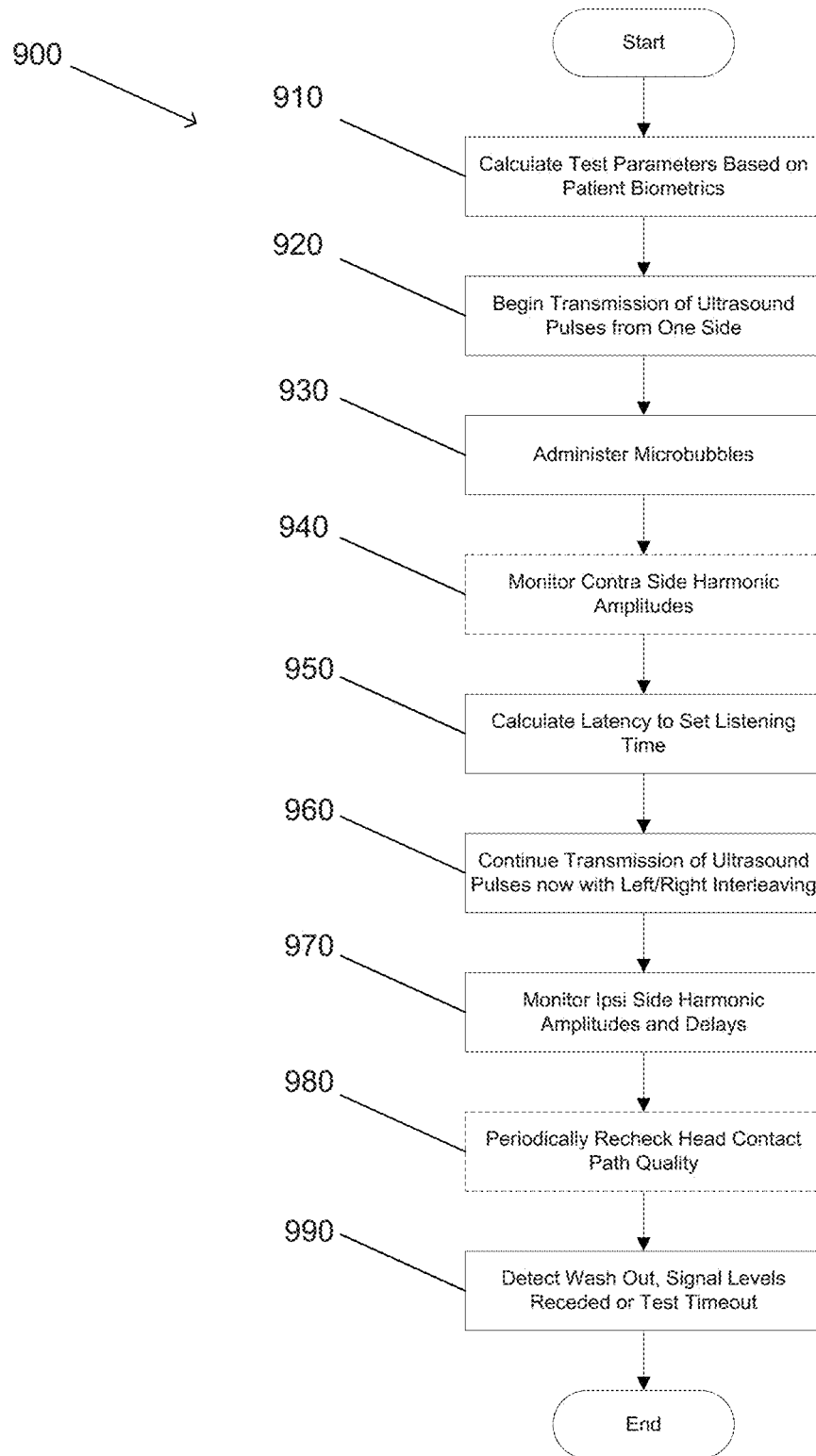
FIG. 9 is a flow chart illustrating a process for performing diagnostic tests using a portable ultrasound device in accordance with an embodiment of the invention.

Turning now to FIG. 9, a method for performing a diagnostic test on a patient using a portable ultrasound device is illustrated in accordance with an embodiment of the invention. Process 900 includes calculating (910) test parameters based on the patient's biometrics. Biometrics can include, but are not limited to, head size, cranial thickness, head shape, brain shape, baseline acoustic measurements, and/or any other biometric measurement as appropriate to requirements of given applications. Once test parameters have been established, transmission of ultrasound pulses from one of the transducer assemblies can begin (920). In many embodiments, one transducer assembly transmits, and one receives. In many embodiments, one transducer assembly transmits, and both receive. In numerous embodiments, both transducer assemblies transmit, and both or one transducer assembly receives. In various embodiments, the portable ultrasound device alternates which transducer assembly transmits.

Microbubbles can be administered (930) to the patient, and contra side harmonic amplitudes can be monitored (940). In this way, the portable ultrasound device can have backup readings. However, monitoring contra side harmonic amplitudes is not required. The portable ultrasound device can calculate (950) latency to set the listening time. In many embodiments, a test ping can be sent from at least one transducer assembly. A second transducer assembly on the opposite side of the skull can pick up the ping, and the travel time can be recorded. In many embodiments, the transducer assembly that sent the test ping can receive the reflection of the test ping from the opposite side of the skull, which can be used to calculate latency. Further, a test pulse can be transmitted between two contralateral transducer assemblies while microbubbles are in the patient. The difference in the transmit time of a baseline test pulse without microbubbles and the transmit time at the same frequency with microbubbles can indicate the microbubble latency. As one can appreciate, there are numerous ways to calculate latency depending on the number of transducer assemblies used as appropriate to the requirements of a given application. The portable ultrasound device can continue transmitting (960) ultrasound pulses with right/left interleaving, while monitoring (970) ipsilateral side harmonic amplitudes and delays. Monitored ipsilateral side harmonic amplitudes and delays can be used by portable ultrasound devices to distinguish microbubble harmonic response patterns in order to generate diagnostic support data using methods described above. Recorded data can be stored by the portable ultrasound device on a machine readable medium such as random access memory, a hard disk drive, a solid state drive, a flash drive, or any other form of machine readable medium. Ultrasound pulses can be transmitted over a range of voltages and/or frequencies. The portable ultrasound device can detect (990) wash-out of microbubbles by determining that signal levels have receded. In many embodiments, diagnostic tests performed by the portable ultrasound device are on a predetermined timer. If the timer hits a predetermined amount of time, the test will terminate.

While a specific method for performing a diagnostic test on a patient using a portable ultrasound device is discussed above with respect to FIG. 9, there are numerous approaches to performing a diagnostic test in accordance with the requirements of a given application. In many embodiments, diagnostic tests can be performed using a contralateral receiving approach. In numerous embodiments, diagnostic tests can be performed using an ipsilateral receiving approach. Methods for performing diagnostic tests using contralateral and ipsilateral receiving approaches are described below.

Contralateral Receiving Approach

Figure 12:
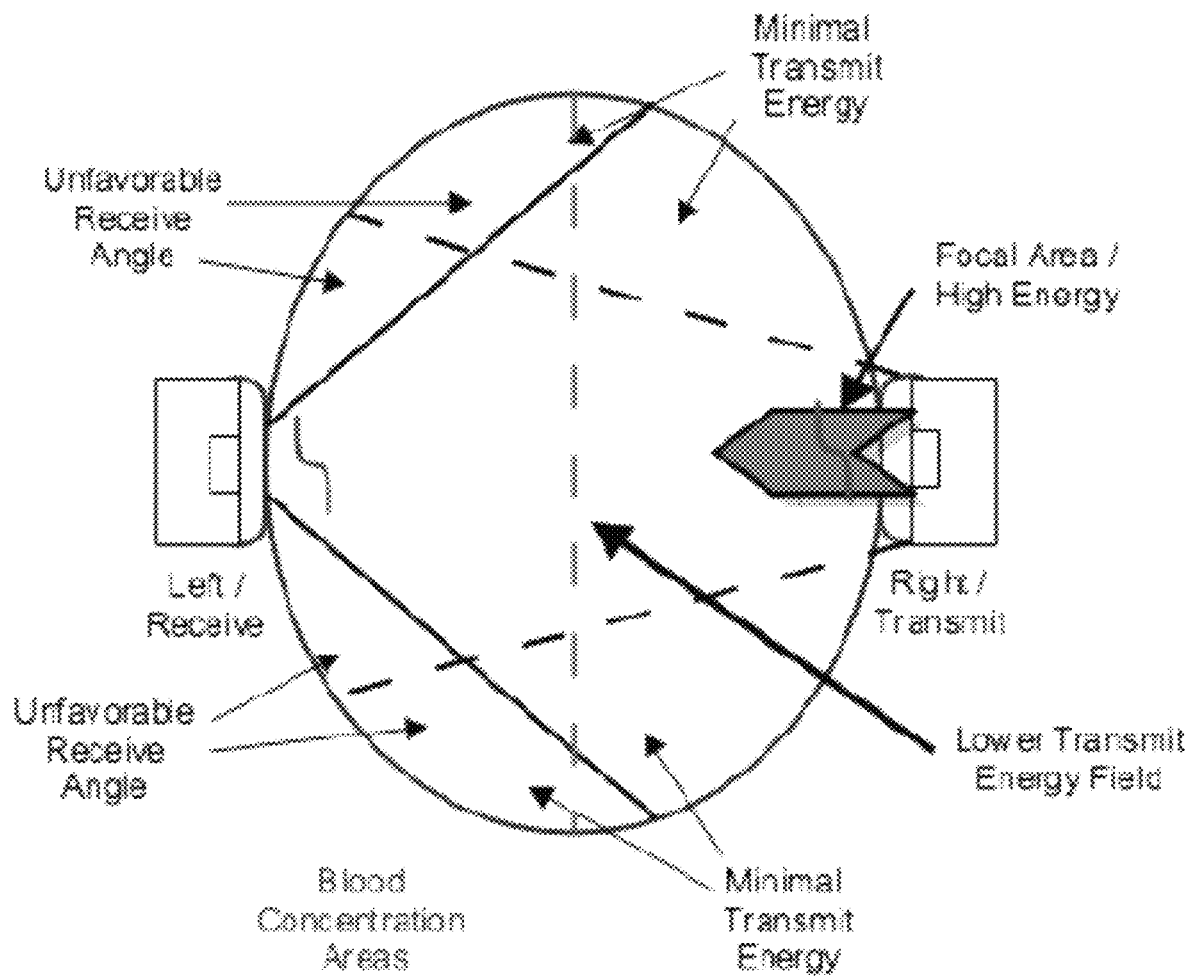
FIG. 12 is a diagram conceptually illustrating a contralateral receiving approach to generating diagnostic support data in accordance with an embodiment of the invention.
Figure 13:
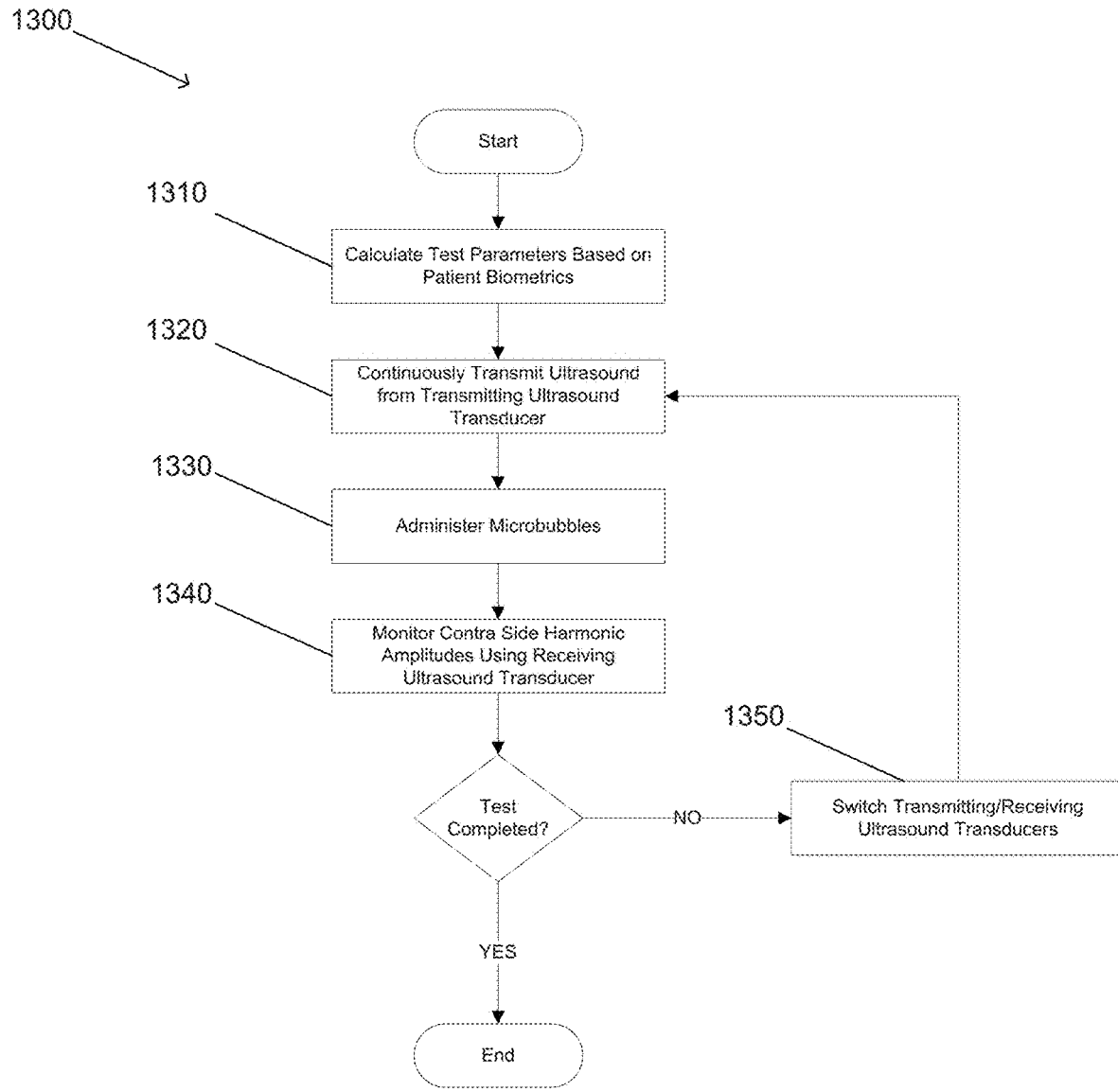
FIG. 13 is a flow chart illustrating a process for performing a contralateral receiving approach to generating diagnostic support data in accordance with an embodiment of the invention.

Contralateral receiving approaches involves transmitting ultrasound using a first transducer assembly and receiving the ultrasound using a second transducer assembly on the opposite side of the head from the first transducer assembly (the "contra" position). Turning now to FIG. 12, a conceptual diagram illustrating a contralateral receiving approach in accordance with an embodiment of the invention is illustrated. A process for performing a contralateral receiving approach is illustrated in FIG. 13.

Process 1300 includes calculating (1310) test parameters based on patient biometrics. In many embodiments, calculating test parameters is performed using methods described below. Process 1300 also includes continuously transmitting (1320) ultrasound from a transmitting transducer assembly. Microbubbles can be administered (1330) using methods similar to those described above. In many embodiments, microbubbles are administrated prior to beginning continuous ultrasound transmission. Contra side harmonic amplitudes can be monitored (1340) using the receiving transducer assembly. If the diagnostic test has not been finished, the transmitting and receiving transducer assemblies can switch (1350) roles. That is, the transmitting transducer assembly can become the receiving transducer assembly and vice versa. If the test is completed, the process can be terminated. In numerous embodiments, steps 1510-1540 can be repeated multiple times prior to switching the transducer assemblies. The contralateral receiving approach uses at least two transducer assemblies at the same time. However, the ipsilateral receiving approach can be performed using a single transducer assembly. A discussion of an ipsilateral receiving approach can be found below.

Ipsilateral Receiving Approach

Figure 14:
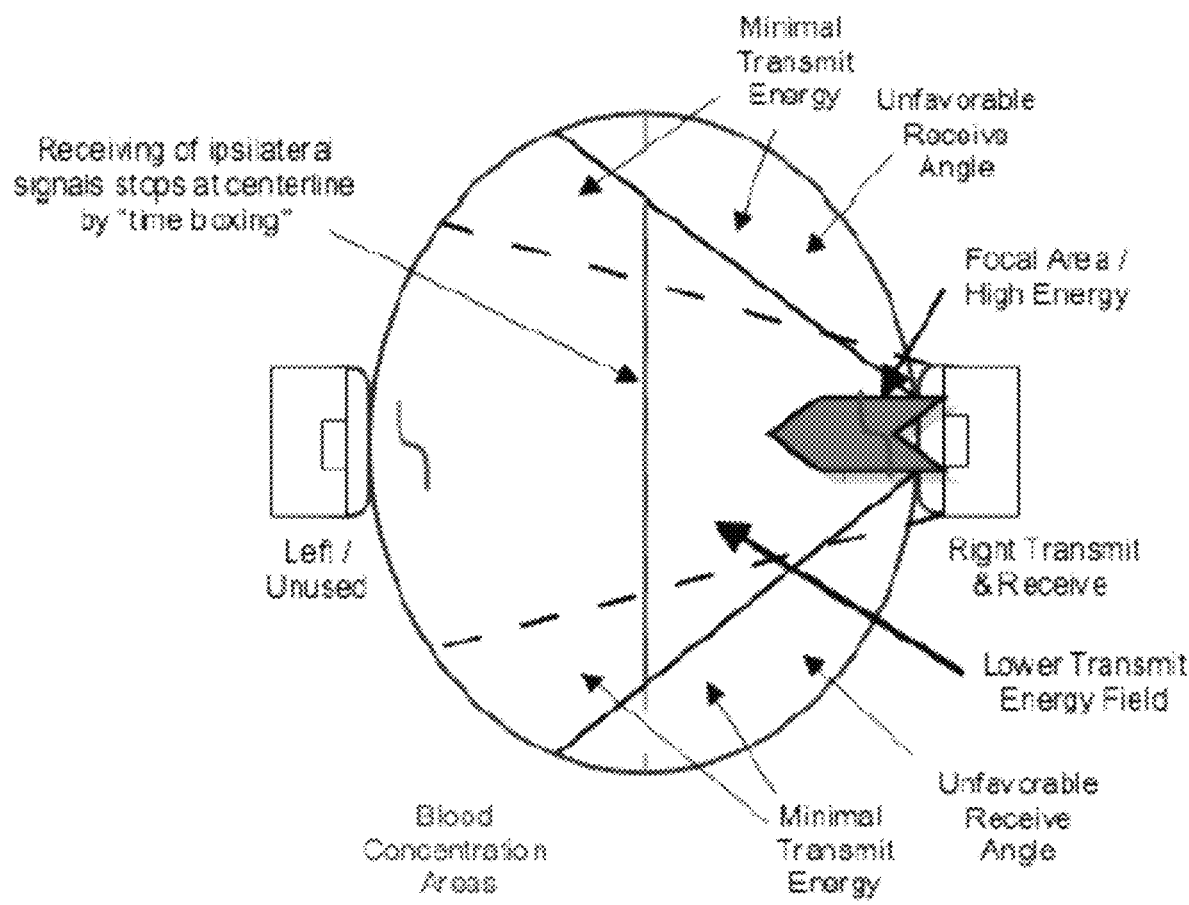
FIG. 14 is a diagram conceptually illustrating an ipsilateral receiving approach to generating diagnostic support data in accordance with an embodiment of the invention.

The ipsilateral receiving approach involves using a transducer assembly to both transmit and receive ultrasound signals. As discussed above, signals received can be time-boxed in order to better isolate harmonics generated in the hemisphere of the brain closest to the ultrasound transceiver. A conceptual diagram illustrating a contralateral receiving approach in accordance with an embodiment of the invention is illustrated in FIG. 14.

Figure 15:
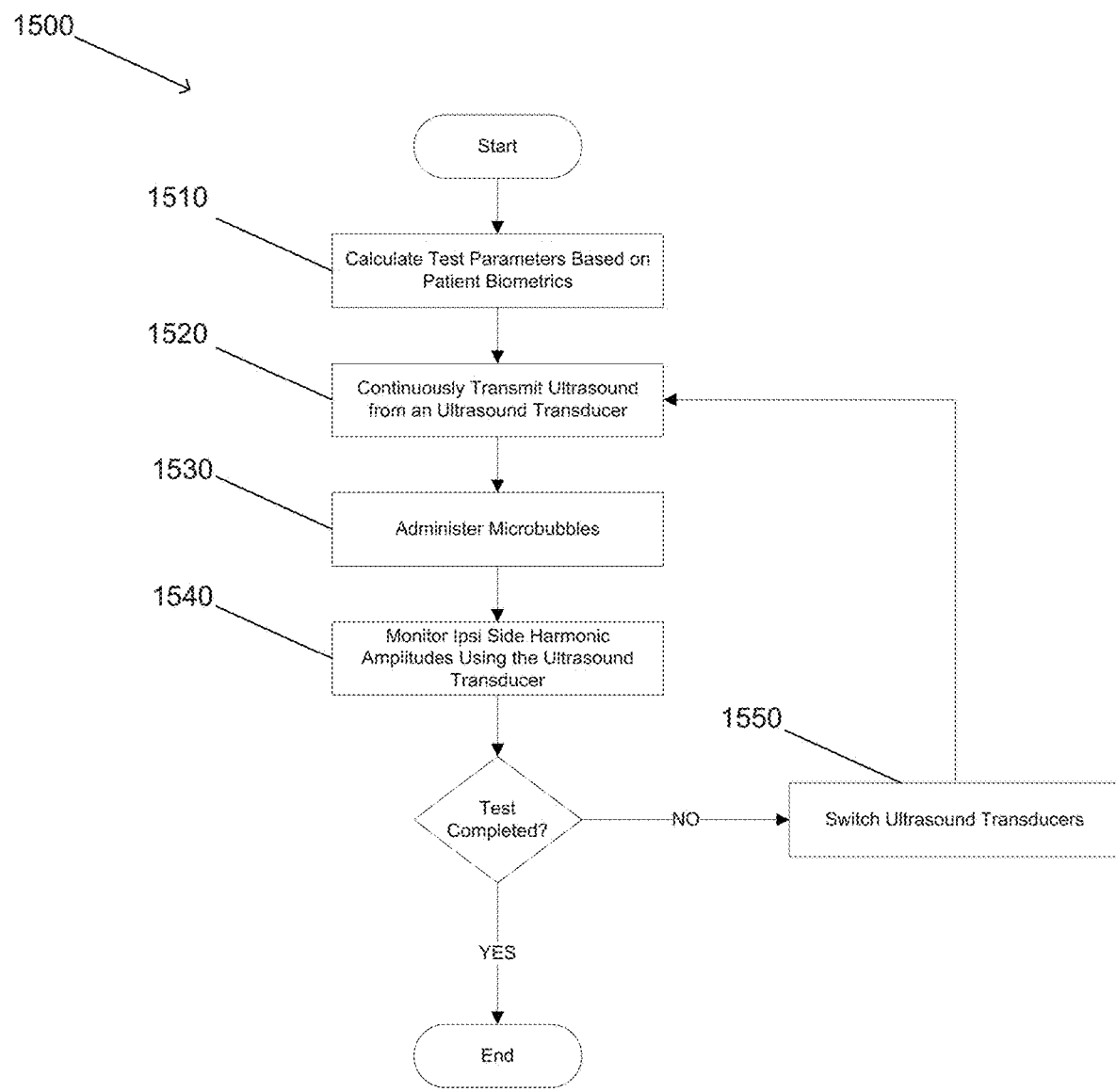
FIG. 15 is a flow chart illustrating a process for performing an ipsilateral receiving approach to generating diagnostic support data in accordance with an embodiment of the invention.

Turning now to FIG. 15, a process for performing an ipsilateral receiving approach is illustrated in accordance with an embodiment of the invention. Process 1500 includes calculating (1510) test parameters based on patient biometrics. In many embodiments, calculating test parameters is performed using methods described below. Process 1500 also includes continuously transmitting (1520) ultrasound from a transducer assembly. Microbubbles can be administered (1530) using methods similar to those described above. In many embodiments, microbubbles are administrated prior to beginning continuous ultrasound transmission. Ipsi-side harmonic amplitudes can be monitored (1540) using the transducer assembly used for transmitting. If the diagnostic test has not been finished, a second transducer assembly placed on the opposite side of the patient's head can be used to measure the opposite hemisphere of the brain. If the test is completed, the process can be terminated.

While processes for performing diagnostic tests in accordance with an embodiment of the invention is described above, a person of ordinary skill in the art would recognize that there are any number of ways that portable ultrasound devices can perform diagnostic tests in accordance with the requirements of given applications. Different processes could include, but are not limited to, using different test parameters, using different ordering and/or number of tests, using different tests, and/or using different numbers of transducer assemblies. Diagnostic tests can be tailored to specific patients and/or specific scenarios using test parameters. Methods for generating test parameters are described below.

Generating Test Parameters Using Portable Ultrasound Devices

Prior to performing diagnostic tests using a portable ultrasound device, test parameters can be determined to direct the test. Proper calculation of test parameters can enable more accurate results and diagnoses. In numerous embodiments, test parameters are determined using calibration tests. In many embodiments, a test-pad can be included on the portable ultrasound device. The test-pad can be used during self-checks and self-validation to provide a standardized testing environment. Users can be prompted to hold at least one transducer assembly against the test-pad. In many embodiments, the test pad has a holder for at least one transducer assembly to further standardize the testing environment. The test-pad can include a variety of sensors, or cover a variety of sensors used to perform self-checks. In numerous embodiments, self-checks occur in the air, on the patient, or using a different medium as appropriate to the requirements of given applications.

Figure 10:
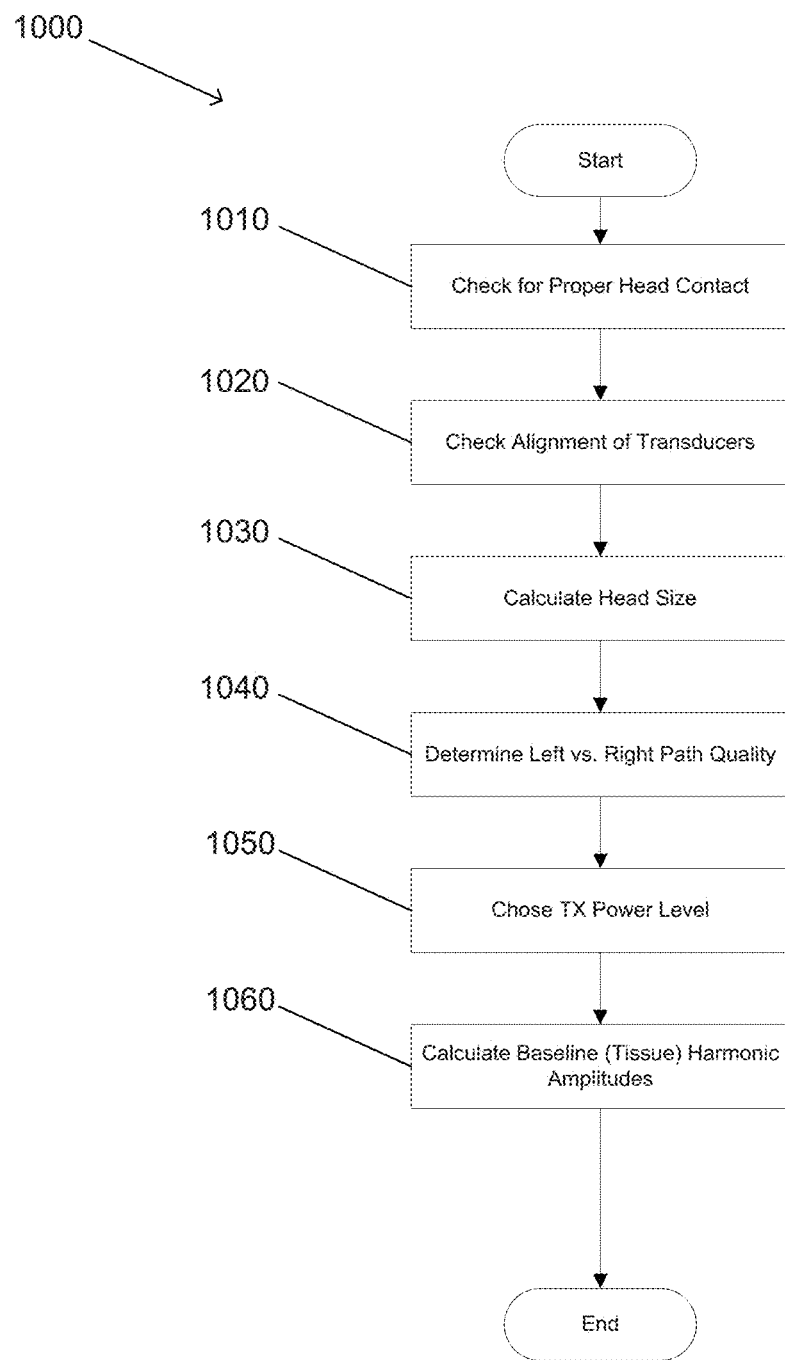
FIG. 10 is a flow chart illustrating a process for calculating various test parameters using a portable ultrasound device in accordance with an embodiment of the invention.

Turning now to FIG. 10, a process for calculating various test parameters using a portable ultrasound device in accordance with an embodiment of the invention is illustrated. Process 1000 includes checking (1010) for proper head contact between at least one transducer assembly and the patient's head, and checking (1020) the alignment of the at least one transducer assembly. Head size can be calculated (1030), and left vs. right path quality can be determined (1040). Transmission power level can be chosen (1050). In many embodiments, a series of at least one test ping at multiple, predetermined power levels can be transmitted in order to choose the power level at which signal clarity is best. Portable ultrasound devices can calculate (1060) baseline (tissue) harmonic amplitudes. The processes for determining test parameters referenced in FIG. 10 are described in further detail below, however, any number of specific steps can be used to determine test parameters in accordance with given applications Confirming Transducer Assembly Alignment In many embodiments, there are two transducer assemblies that are placed in proper contact with the patient's head. In numerous embodiments, the transducer assemblies are placed on opposite sides of the patient's head above the ears over the temporal bone in a contralateral fashion. In a variety of embodiments, the portable ultrasound device detects whether the transducer assembly is in contact with the body by monitoring impedance. Impedance monitoring can occur periodically to confirm that there is no loss of contact during operation of the portable ultrasound device.

The alignment of the transducer assemblies can be checked. Alignment can be checked by transmitting test pings across the patient's skull. Depending on how the ultrasound test pings are received, the portable ultrasound device can determine whether or not the transducer assemblies are properly placed. In many embodiments, the portable ultrasound device can detect whether a transducer assembly is placed properly and whether skull thickness is acceptable by monitoring signal level received by a contralateral transducer assembly. In a variety of embodiments, proper transducer assembly placement and acceptable skull thickness are detected using a single transducer assembly on one side of the skull by transmitting a signal and monitoring for the return signal after a prescribed time delay. This can indicate that the signal has propagated past the skull, into the brain tissue, and returned through the skull again. In numerous embodiments, the degree of signal symmetry between a left transducer assembly and right transducer assembly can be monitored to determine proper contact and/or placement of the transducer assemblies. If the tissue and/or microbubble resonance peaks are in the same locations between a left to right and right to left signal transmission, it is likely that the transducer assemblies are placed symmetrically. In some embodiments, only signals with frequencies that are known to not be affected by microbubbles are checked.

Alignment can also be checked by comparing right/left signal travel times. A first transducer assembly can transmit while a second transducer assembly receives. Appropriate time-boxing can be done to help ensure that there are no echoes being considered. After the direct transmission traveling once across the head has been measured, then the second transducer assembly transmits and the first transducer assembly receives. The travel time should be the same assuming only one direct path across. If one transmission took less time than the other, then it can suggest that the longer time involved echoes rather than a direct path which would occur due to a lack of alignment. Correction of the alignment can be indicated until the travel times are essentially the same. Once travel times are the same, then signal strengths can be compared. Since each signal is traveling the same path, the signal strengths should be effectively identical assuming similar transducer assembly performance and assuming co-axial alignment. Assuming that the transducer assemblies are verified to be working properly and calibrated to be performing as expected, then the primary contributor to signal difference can be assumed to be lack of alignment. If the signal received by one transducer assembly is lower than the other, then the opposite transducer assembly might not be pointed co-axially. However, there are a variety of ways that alignment can be determined, including, but not limited to, those described above, manual checks, positioning bands, or any other alignment method as appropriate to the requirements of a given application.

The user of the portable ultrasound device can be alerted that the transducer assemblies are properly and/or improperly placed via an auditory and/or visual cue. In numerous embodiments, audio feedback in near real-time can be generated in order to help the user to place the transducer assemblies. Iterative measurements can be taken by transmitting a positioning test ultrasound signal and listening to the echo return can be performed similar to a path quality measurement check in such a way that an audio output speaker is configured to emit a sound with pitch proportional to the returned signal amplitude so that the user can locate the optimum placement of the transducer assemblies. In many embodiments, optimum placement is determined by measuring the amount of signal received form a test pulse. Amount of signal can be measured by comparing the voltage used to generate the test pulse with the voltage received from the test pulse, measuring the amplitude of the signal received compared to the signal transmitted, calculating acoustic pressure, or any other measurement as appropriate to the requirements of a given application. In numerous embodiments, a visual feedback is given to the user in order to assist with finding optimal placement of the transducer assemblies. Portable ultrasound devices can use a signal level indicator on a display in order to give visual feedback. However, any number of visual and/or audio feedback methods can be used in order to assist the user with proper transducer assembly placement. In many embodiments, the positioning signal is transmitted at 220 kHz. In other embodiments, any of a variety of signals and/or frequencies can be utilized as appropriate to the requirements of a given application. Alignment checks can be performed a single time, or multiple times during the use of a portable ultrasound device on a patient in order to confirm that there is no loss of proper placement during operation.

Checking Path Quality

Portable ultrasound devices can check path quality in any of a variety of ways. Checking path quality can verify accurate data recording during tests performed by portable ultrasound devices. Portable ultrasound devices can check path quality prior to performing diagnostic tests. In many embodiments, portable ultrasound devices periodically check path quality. In numerous embodiments, portable ultrasound devices continuously check path quality.

Portable ultrasound devices can initiate at least one test ping from each of a left transducer assembly and a right transducer assembly. Based on the quality of the reception of each signal, signal quality can be determined using a left transducer assembly to transmit and using a right transducer assembly to transmit. A check of path quality can be similar to a check of alignment as described above. In many embodiments, path quality is measured based upon tissue noise signals that are detected during a baseline test. Tissue can create scattered signals even without the presence of microbubbles. Accordingly, significant harmonics in the absence of microbubbles can indicate poor path quality. The scattered tissue signals are omnidirectional and return to the ipsilateral transducer assembly without any reflection path.

During the transmission of ultrasound pulses, the portable ultrasound device can periodically recheck the head contact path quality in order to maintain acceptable performance. Ipsilateral path quality can be assessed by transmitting, then waiting for the transmitted echo to return, thereby measuring the audio transmission path quality on a round-trip basis. By assessing path quality on both sides of the head in advance of measurements, microbubble signals can be normalized for comparison between the two sides. Path quality assessment can allow the detection of unusual conditions such as a person with a plate in his or her head, abnormal brain morphologies, severe head injuries resulting in damage to the skull on one side, or any other unusual condition as appropriate to the requirements of given applications. Skull abnormalities can be characterized by a fairly predictable signal reflection occurring approximately 1 cm from the face of the transducer assembly. 1 cm from the face of the transducer assembly can be assumed to be the flesh/bone transition layer, however this distance can be variable based on the type of transducer assembly used, the patient's skin, the ultrasound gel pad used, or any number of other differences in construction as appropriate to the requirements of given applications. The portable ultrasound device can configure the transducer assembly to adapt to the abnormal morphology.

In many embodiments, the portable ultrasound device can detect a change in impedance of the transducer assembly circuit by monitoring the "ring-up" profile of the transducer assembly. The portable ultrasound device can configure a transducer assembly to produce a signal of a predetermined amplitude, which has a repeatable ring-up signature that is a function of its impedance and the circuit driving it. The ring-up pattern can be measured and modifications from the expected pattern can be measured. Deviations from the expected pattern can be caused by the media between the transmission element and the receiving element. In this way, changes of impedance can be measured. A large change in impedance can signify that there is a short to ground through the patient's body. In a variety of embodiments, the portable ultrasound device has a library of ring-up patterns that can be associated with various conditions.

While several methods of checking for path quality have been described above, portable ultrasound devices are not limited to using these methods. Methods for determining path quality can take on any of a number of forms as appropriate to the requirements of specific embodiments. In addition to the tests described above, portable ultrasound devices can perform additional self-check tests to further calibrate the device, and confirm proper working order of the device. Methods for performing self-check tests are described below.

Methods for Performing Self-Check Tests Using a Portable Ultrasound Device

Self-check tests can be performed by portable ultrasound devices in accordance with various embodiments of the invention. Self-check tests can confirm that the portable ultrasound device is functional and ready to perform diagnostic tests on a patient. Self-check tests can calibrate a portable ultrasound device to verify that all components are configured to record and transmit reliable information. Self-check tests can be performed in a variety of ways and in a variety of orders.

Figure 8:
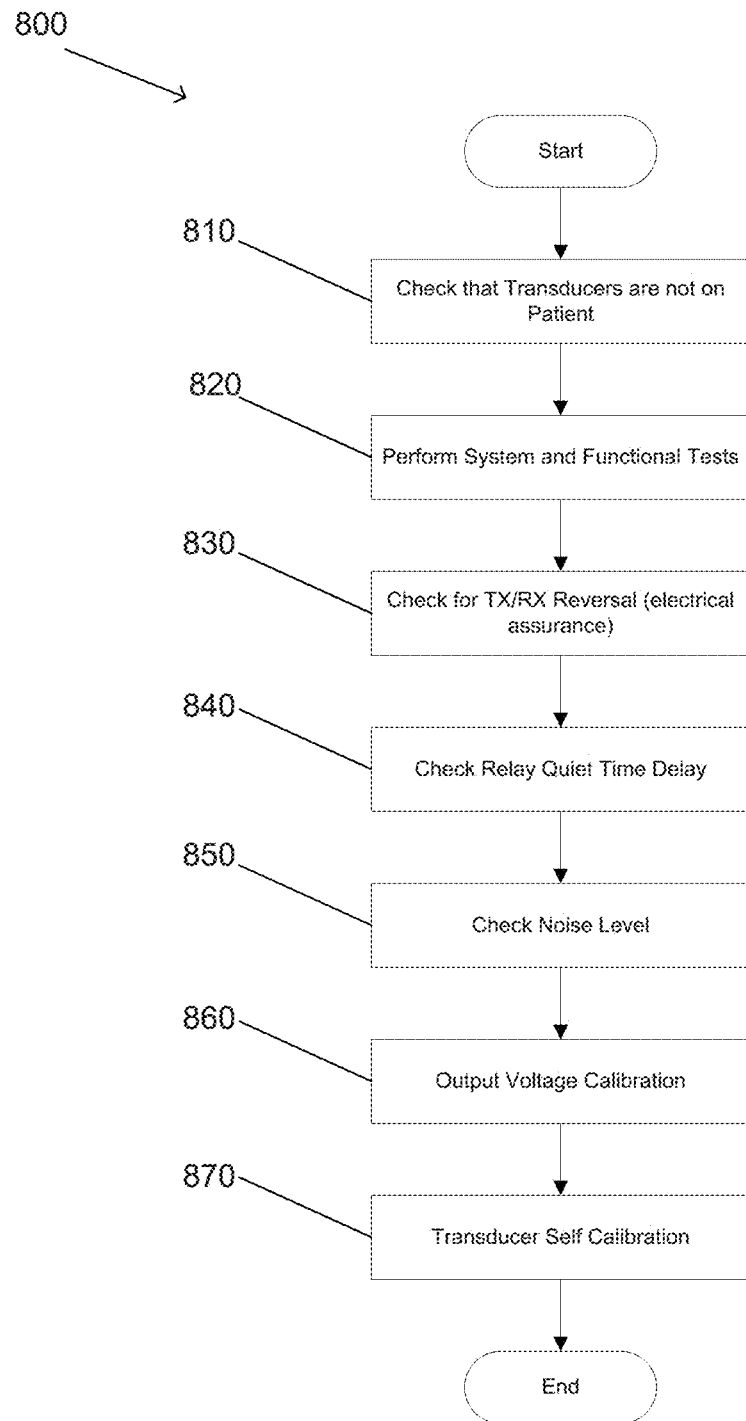
FIG. 8 is a flow chart illustrating a process for performing self-check tests using a portable ultrasound device in accordance with an embodiment of the invention.

A process for performing self-checks using a portable ultrasound device in accordance with an embodiment of the invention is illustrated in FIG. 8. Process 800 includes confirming (810) whether the transducer assemblies are properly positioned on the patient. In many embodiments, checking (810) that the transducer assemblies are not on the patient is done by sending safe test pings from at least one transducer assembly. In numerous embodiments, checking (810) is done manually by a user. While manual checks can be performed, automatic failsafe checks can be performed as well.

Process 800 can include performing (820) system and functional tests. In many embodiments, system and functional tests involve confirming that the transducer assemblies are capable of sending and receiving ultrasound. The portable ultrasound device can also check for proper connections between components to validate that all transducer assembly elements are functioning properly. The portable ultrasound device can also check (830) for transmit/receive (TX/RX) reversal in order to determine electrical assurance. By measuring the transmit voltage achieved at a certain power setting at a transmit element and checking the voltage level obtained at a receive element, the portable ultrasound device can determine if TX/RX reversal may have occurred in either transducer assembly. In many embodiments, TX/RX reversal can be detected by characterizing impedance and/or returned signal signature that occurs in free air when reversal occurs. Reversal can also be detected by calculating impedance based on values returned by digital potentiometers electrically coupled to the ultrasound transducer assemblies. In several embodiments, the portable ultrasound device checks (840) the relay quiet time delay and checks (850) the noise level. In many embodiments, the noise level can be monitored before and after signal generation and measurements to verify that noise levels are not excessively risking improper signal analysis. In some embodiments, the portable ultrasound device uses the results of the noise level checks to estimate the noise power. The output voltage can be calibrated (860) and the transducer assemblies can be calibrated (870). Methods for calibrating transducer assemblies are described below.

Transducer Assembly Integrity and Calibration Tests

In addition to the tests above, portable ultrasound devices can perform system and functional tests can include a variety of calibration tests and integrity checks that can determine whether or not the portable ultrasound device is in working order. Such tests can include, but are not limited to, circuit integrity tests, transducer assembly performance tests, or any other functional test as appropriate to the requirements of given applications.

In many embodiments, short circuit detection is performed. Portable ultrasound devices in accordance with a number of embodiments of the invention can monitor the current output to at least one transducer assembly, and monitor the current returned from the at least one transducer assembly, and turn off the circuit if the current returned is significantly less than the output current as indicative of a short circuit. Further, portable ultrasound devices can determine if there is a fault through the patient based on human impedance. Given that the average range of impedance for a human body has been determined, if there is more electrical load than the transducer applies, but not enough to be caused by a short circuit, then there may be a fault through the body. In the event that there is a short circuit or a fault, portable ultrasound devices can automatically shut down.

In many embodiments, functional tests of the transducer assemblies include making sure that the receive elements are properly functioning. In some embodiments, there is crosstalk between transducer assemblies in free air, which can be used to verify functionality. Minimal signal is expected to be detected on the receive chain during a free air transmit check. The targets for isolation that can be achieved in transducer assemblies can be on the order of 50 dB and receive chain filtering of a 220 kHz signal can add approximately an additional 50 dB of suppression. In order to perform the functional test, a transmitter element can be switched so it is connected to the receiver. The receiver can be at the junction of the receiver and the first high pass filter in the receive chain, and a characterization of the impedance at this connection point can be obtained. Once the characterization of the impedance is obtained, it can be calculated what voltage should be observed when the transmitter attempts to transmit a specified signal at this junction. The voltage obtained can be much lower than that of the transmit element, and can be predictable in order to achieve validation of functionality. Difference in receiver element impedance can be calculated and signal measurement normalization factors can be calculated.

Part to part variations in components can affect measurements taken by ultrasound devices. Component behaviors can be characterized and compiled into profiles. Each component can have an individual profile. Profiles can be stored in the memory of portable ultrasound devices. Profiles can be used in calibration to tune measurement processes. In some embodiments, portable ultrasound devices have a non-volatile memory device used to store profiles. In a variety of embodiments, portable ultrasound devices can automatically detect which profiles should be used based on the attached components. Automatic detection can occur through an exchange of information between components. Automatic detection can occur based on unique resistor values in connection cables. In some embodiments, serial numbers can be used to access appropriate profiles. In numerous embodiments, profiles can be stored remotely and accessed via a network connection.

In many embodiments, portable ultrasound devices can conduct various calibration steps on the transducer. Portable ultrasound devices can detect when gel pads have been connected based on change in electrical load in the transducer. Further, in many embodiments, confirmation that the gel pads have been connected can be achieved by identifying a change in impedance on one transducer assembly, a lack of path quality between the two transducer assemblies, and then a subsequent similar change in impedance of the other transducer assembly. The amplifier section of each transducer assembly that drives the transmission of the transducer assembly can be calibrated in such a way that the desired acoustic output is nearly identical for both sides at each target power level. The portable ultrasound device can measure the output voltage obtained at one or more settings of the transmit circuit, and then determine the optimum voltage setting for each power level such that the two sides have equal output power given the individual impedance of the transducer assemblies. In many embodiments, the portable ultrasound device captures at least one measurement of the signals received by the receive elements while performing the calibrations and/or by the opposite transmit element (if they are in contact with a common media) in order to provide measurements of the overall conversion efficiency for both transducer assemblies, through the transmit element(s) and back through the receive element(s). The received calibration signals can be used to tune the calibration of the transmitter settings, and/or the relative performance of each side.

In a variety of embodiments, a closed-loop test is done where a transmitter element of a transducer assembly is driven and the receiver element is monitored. A connection before the high pass filter of the receive chain to the analog to digital converter can be made so that the signal can be detected prior to the filters. In this way, the calibration of the transducer assemblies can be automated by the portable ultrasound device.

In a number of embodiments, the calibration process includes a first transmit element producing at least one reference burst at a selected transmit output voltage. Each receive element can receive the transmission from the transmit element. Next, the opposite transmit element produces the same reference burst or bursts and each receive element can receive the second set of reference bursts. For each measurement sequence, the peak amplitude can be calculated. The transducer assemblies can be analyzed using the calculated peak amplitudes and a matrix of preset reference values. In other embodiments, calibration can be performed using any of a variety of waveforms and signal processing techniques.

In certain embodiments, calibration includes latency detection. Latency can be measured in a variety of ways. In some embodiments, there is significant part to part variation in transmit latency and/or latency of drug to drug variation in latency of microbubbles. A test ping can be transmitted from one transducer assembly to a second transducer assembly and the time for the signal to travel between the two transducer assemblies can be factored out. The remaining time can indicate the latency due to part to part variation.

In many embodiments, a target amplitude for the transducer assemblies is chosen. The target amplitude can be a preconfigured target amplitude, or a user input target amplitude. The portable ultrasound device can then initiate test transmission of ultrasound at the target amplitude using a transmit element, and monitor the actual amplitude obtained at a receive element. An adjustment factor can be calculated to apply subsequent settings so that the actual amplitude will conform to the test parameters. In a variety of embodiments, one or more digital potentiometers can be electrically coupled to the ultrasound transducer assemblies. The digital potentiometers can be used to tune the ultrasound transducer assemblies to standardize the output level. In this way, self-calibration can allow the portable ultrasound device to compensate for many part-to-part variations and mismatches that are likely to occur throughout the circuitry.

In numerous embodiments, for a period after the transducer assemblies have been set on a patient's head, the acoustic properties of the gel pads can shift. Shifts in the acoustic properties can be caused by a change in temperature as they reach equilibrium with their new environment including the patient's head. Shifts in acoustic properties can also be caused by changes in pressure as they settle. The period until the acoustic properties stop changing enough to significantly impact data collection is called the "stabilization period." In many embodiments, portable ultrasound devices can calculate stabilization periods. Calculating stabilization periods can involve monitoring harmonic responses and measuring how they change over time. In a variety of embodiments, once stability is achieved, diagnostic testing can proceed.

When ultrasound signals are transmitted, there can be a reflection of the original transmission from the skull boundary, as well as unwanted harmonic reflections. Skull boundary reflections can be triggered when there is a large change in velocity as the ultrasound waves enter the skull. Unwanted harmonics can include harmonics that are not relevant to the current testing. For example, under conditions where the transmit frequency is 220 kHz, harmonics of interest may only be 880 kHz, 1,100 kHz, and 1,320 kHz. Other full harmonics and/or half harmonics not of interest can be considered noise. In many embodiments, by measuring the reflected transmission from the skull boundary, the response can be used as a proxy for knowing the amplitude and/or phase angle of unwanted harmonic reflections. Portable ultrasound devices can use the reflected transmission to screen out noise using measured parameters during diagnostic testing.

In numerous embodiments, portable ultrasound devices can determine whether or not components or circuitry has been manipulated, tampered with, or serviced. Portable ultrasound devices can include a system clock chip, and a backup clock chip with a separate power source. The power supply for the backup clock chip can be connected to the opening in the casing of the portable ultrasound device such that electrical flow is halted if the casing is opened. In numerous embodiments, the backup clock chip cannot be accessed without breaking the casing of the portable ultrasound device. When the system is powered on, if there is a discrepancy between the system clock time and the backup clock time, there is an indication that the unit has been manipulated. If there is an indication that the unit has been manipulated, the portable ultrasound device can initiate calibration tests and/or require an authorization code and/or maintenance information to function. The backup clock chip can be resynced to the system clock after authorization has been established.

As one can readily appreciate, a variety of calibration tests and checks can be performed to confirm that the portable ultrasound device is working properly. The ordering of the steps can be modified, and steps can be omitted and/or added as appropriate to the requirements of given applications. Accuracy and precision of measurements taken using portable ultrasound devices can be increased by performing self-check tests to confirm functionality of components, and calibration tests to detect variance in the testing scenario.

Post Natal Brain Damage Diagnosis

In numerous embodiments, portable ultrasound device can be used to detect postnatal brain damage. In many cases, there is no easy way to test whether an infant might suffer from severe brain damage such as intracranial hemorrhage, stroke, intracranial hypertension caused by a tumor, or any other severe brain injury. A transducer assembly can be attached to the infant's head. In many embodiments, the transducer assembly is attached to the anterior fontanelle. The transducer assembly can collect tissue harmonic frequency responses. If there is elevated intracranial pressure, the signal amplitudes can be decreased compared to normal pressure responses. Normal pressure responses can be predetermined and stored in the memory of a portable ultrasound device and/or a server system. Normal pressure responses can be calculated using any of, but not limited to, pulse measurements, blood pressure measurements, temperature, weight, and any other metric as appropriate to the requirements of a given application.

Although the present invention has been described in certain specific aspects, many additional modifications and variations would be apparent to those skilled in the art. In particular, any of the various processes described above can be performed in alternative sequences in order to achieve similar results in a manner that is more appropriate to the requirements of a specific application. It is therefore to be understood that the present invention can be practiced otherwise than specifically described without departing from the scope and spirit of the present invention. Thus, embodiments of the present invention should be considered in all respects as illustrative and not restrictive.

What is claimed is:

1. A system for detecting abnormal blood flow in brains, comprising:
a processor;
a first ultrasound transmitter located on a patient's head in communication with the processor;
a first ultrasound receiver located on the patient's head in communication with the processor;
a memory in communication with the processor, comprising a diagnostics application, where the diagnostics application directs the processor to:
transmit a first ultrasound signal from the first ultrasound transmitter across a patient's brain, where the first ultrasound signal comprises a plurality of ultrasound pulses;
receive the first ultrasound signal using the first ultrasound receiver, where the ultrasound signal is affected during transit by harmonics generated by microbubbles in the blood of the patient stimulated by the first ultrasound signal;
identify a portion of the received first ultrasound signal indicative of abnormal blood flow based on harmonic effects in the received signal;
time-box the first received ultrasound signal such that at least a portion of the patient's brain is overlaid with the first received ultrasound signal; and
detect that an abnormal blood flow event has occurred in a region of the brain within the portion of the patient's brain based on the location of the identified portion of the first received ultrasound signal.

2. The system of claim 1, wherein to identify a portion of the received signal as indicative of abnormal blood flow, the diagnostics application further directs the processor to:
compare a first portion of the first received ultrasound signal corresponding to a first hemisphere of the brain to the portion of the first received ultrasound signal corresponding to a second hemisphere of the brain; and
detect differences in microbubble signal profile between the first hemisphere and the second hemisphere based on the harmonic effects on the first received ultrasound signal.

3. The system of claim 1, wherein the first ultrasound receiver is located on the patient's head ipsilaterally with respect to the first ultrasound transmitter; and
wherein the diagnostics application further directs the processor to:
transmit a second ultrasound signal from a second ultrasound transmitter across the patient's brain, where the second ultrasound transducer is in communication with the processor and is located contralaterally on the patient's head with respect to the first ultrasound transmitter; and
receive the second ultrasound signal using a second ultrasound receiver, where the second ultrasound receiver is located ipsilaterally on the patient's head with respect to the second ultrasound transmitter, where the second ultrasound receiver is in communication with the processor, and where the second ultrasound signal is affected during transit by harmonics generated by microbubbles in the blood of the patient stimulated by the second ultrasound signal.

4. The system of claim 3, wherein the diagnostics application further directs the processor to:
determine the transmit time of ultrasound across the patient's head;
time-box the first received ultrasound signal such that the first time-boxed signal corresponds to a portion of the first received ultrasound signal received during a time period of half of the determined transmit time so that the first time-boxed signal describes a first hemisphere of the brain;
time-box the second received ultrasound signal such that the second time-boxed signal corresponds to the signal received during a time period of half of the determined transmit time so that the second time-boxed signal describes a second hemisphere of the brain; and
compare the first time-boxed signal and the second time-boxed signal for differences in harmonic responses.

5. The system of claim 1, wherein the first ultrasound is located contralaterally on the patient's head with respect to the first ultrasound transmitter; and
wherein the diagnostics application further directs the processor to:
transmit a second ultrasound signal from the second ultrasound transmitter across the patient's brain, where the second ultrasound transmitter is located contralaterally on the patient's head with respect to the first ultrasound transmitter; and
receive the second ultrasound signal using a second ultrasound receiver, where the second ultrasound receiver is located contralaterally on the patient's head with respect to the first ultrasound transmitter, where the second ultrasound receiver is in communication with the processor, and where the second ultrasound signal is affected during transit by harmonics generated by microbubbles in the blood of the patient stimulated by the second ultrasound signal.

6. The system of claim 1, wherein the diagnostics application further directs the processor to locate the position of the detected abnormal blood flow event within the region of the brain.

7. The system of claim 6, wherein the diagnostics application further directs the processor to:
time-box the first received ultrasound signal to reflect spatial segments of the brain; and
determine which spatial segment contains harmonic effects indicating abnormal blood flow events.

8. The system of claim 7, wherein the diagnostics application further directs the processor to:
analyze a first segment of the first received ultrasound signal corresponding to the distance from the first ultrasound transmitter to a predetermined segment distance from the first ultrasound transmitter; and
analyze a set of subsequent segments, where each subsequent segment in the set of subsequent segments sequentially describes the first received ultrasound signal from the first ultrasound transmitter to a distance that is one more predetermined segment distance away from the first ultrasound transmitter than the previous segment.

9. The system of claim 1, wherein the diagnostics application further directs the processor to determine whether the abnormal blood flow event is an ischemia or a hemorrhage based on the first received ultrasound signal.

10. The system of claim 9, wherein the microbubbles generate different harmonic responses depending on the pressure that the microbubbles are subject to; and
wherein the diagnostics application further directs the processor to:
measure the harmonic responses associated with the microbubble harmonic effects;
calculate an intracranial pressure of the patient based on the measured harmonic responses; and
determine a type of abnormal blood flow event based on the intracranial pressure.

11. The system of claim 1, wherein the received first ultrasound signal is further affected by unwanted harmonic noise; and to reduce the effects of the unwanted harmonic noise, the detection application further directs the processor to:
transmit a second ultrasound signal using the first ultrasound transmitter, where the second ultrasound signal is 180 degrees out of phase with the first transmitted ultrasound signal; and
filter the first received ultrasound signal to remove unwanted harmonic noise, where the unwanted harmonic noise is correlated to phase.

12. The system of claim 1, wherein the first received ultrasound signal comprises a first peak and a second peak, where the first received ultrasound signal's first peak and second peak correspond to harmonic effects; and wherein the detection application further directs the processor to:
locate the first received ultrasound signal's first peak by finding a first inflection point in the received first ultrasound signal;
locate the received ultrasound signal's second peak by finding a second inflection point in the first received ultrasound signal; and
match the pattern of the peaks in the first received ultrasound signal to predetermined patterns of peaks representing brains suffering from abnormal blood flow events.

13. The system of claim 12, wherein the detection application further directs the processor to:
transmit a second ultrasound signal using a second ultrasound transmitter, where the second ultrasound transmitter is located on the patient's head contralaterally with respect to the first ultrasound transmitter, and where the second ultrasound transmitter is in communication with the processor;
receive the second ultrasound signal using at least one of the first ultrasound receiver and a second ultrasound receiver, where the second ultrasound receiver is located on the patient's head contralaterally with respect to the first ultrasound receiver, where the second received ultrasound signal comprises a first peak and a second peak, and where the second ultrasound signal's first peak and second peak correspond to harmonic effects;
locate the second received ultrasound signal's first peak by finding a first inflection point in the received first ultrasound signal;
locate the second received ultrasound signal's second peak by finding a second inflection point in the received first ultrasound signal;
calculate the differences between the first received ultrasound signal's peaks with the second received ultrasound signal's peaks; and
detect if an abnormal blood flow event has occurred based on the calculated differences.

14. The system of claim 1, wherein a first ultrasound transducer assembly comprises the first ultrasound transmitter and the first ultrasound receiver.

15. The system of claim 14, wherein the first ultrasound transducer assembly comprises a coaxial dual element ultrasound transducer.

16. A method for detecting abnormal blood flow events, comprising:
transmitting a first ultrasound signal from a first ultrasound transmitter across a patient's brain, where the first ultrasound signal comprises a plurality of ultrasound pulses;
receiving the first ultrasound signal using a first ultrasound receiver, where the ultrasound signal is affected during transit by harmonics generated by microbubbles in the blood of the patient stimulated by the first ultrasound signal;
identifying a portion of the received first ultrasound signal indicative of abnormal blood flow based on harmonic effects in the received signal;
time-boxing the first received ultrasound signal such that at least a portion of the patient's brain is overlaid with the first received ultrasound signal; and
detecting that an abnormal blood flow event has occurred in a region of the brain within the portion of the patient's brain based on the location of the identified portion of the first received ultrasound signal.

17. The method of claim 16, wherein detecting if the abnormal blood flow event has occurred further comprises:
comparing the portion of the first received ultrasound signal corresponding to a first hemisphere of the brain to the portion of the ultrasound signal corresponding to a second hemisphere of the brain; and detecting differences in microbubble signal profile between the first hemisphere and the second hemisphere based on the harmonic effects on the first received ultrasound signal.

18. The method of claim 16, wherein the first ultrasound receiver is located on the patient's head ipsilaterally with respect to the first ultrasound transmitter; and further comprising:

transmitting a second ultrasound signal using a second ultrasound transmitter across the patient's brain, where the second ultrasound transmitter is located on the patient's head contralaterally with respect to the first ultrasound transmitter; and receiving the second ultrasound signal using a second ultrasound receiver, where the second ultrasound receiver is located on the patient's head contralaterally with respect to the first ultrasound transmitter, and where the second ultrasound signal is affected during transit by harmonics generated by microbubbles in the blood of the patient stimulated by the second ultrasound signal; and detecting if the abnormal blood flow event has occurred is further based on the harmonic effects on the second received ultrasound signal.

19. The method of claim 18 further comprising:

determining the transit time of ultrasound across the patient's head;

time-boxing the first received ultrasound signal such that the first time-boxed signal corresponds to the signal received during a time period of half of the determined transmit time so that the first time-boxed signal describes a first hemisphere of the brain;

time-boxing the second received ultrasound signal such that the second time-boxed signal corresponds to the signal received during a time period of half of the determined transmit time so that the second time-boxed signal describes a second hemisphere of the brain; and comparing the first time-boxed signal and the second time-boxed signal for differences in harmonic responses.

20. The method of claim 16, wherein the first ultrasound receiver is located on the patient's head contralaterally with respect to the first ultrasound transmitter; and further comprising:

transmitting a second ultrasound signal from a second ultrasound transmitter across the patient's brain, where the second ultrasound transmitter is located on the patient's head contralaterally with respect to the first ultrasound transmitter;

receiving the second ultrasound signal using a second ultrasound receiver, where the second ultrasound receiver is located on the patient's head ipsilaterally with respect to the first ultrasound transmitter, and where the second ultrasound signal is affected during transit by harmonics generated by microbubbles in the blood of the patient stimulated by the second ultrasound signal; and detecting if the abnormal blood flow event has occurred is further based on the harmonic effects on the second received ultrasound signal.

* * * * *